United States Patent
Ouerfelli et al.

(10) Patent No.: US 11,413,354 B2
(45) Date of Patent: Aug. 16, 2022

(54) N-ACETYLGALACTOSAMINO DENDRON-CLEARING AGENT FOR DOTA-PRETARGETED RADIOIMMUNOTHERAPY

(71) Applicant: MEMORIAL SLOAN KETTERING CANCER CENTER, New York, NY (US)

(72) Inventors: Ouathek Ouerfelli, New York, NY (US); Guangbin Yang, New York, NY (US); Sarah M. Cheal, New York, NY (US); Steve Larson, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 10 days.

(21) Appl. No.: 17/259,663

(22) PCT Filed: Jul. 10, 2019

(86) PCT No.: PCT/US2019/041236
§ 371 (c)(1),
(2) Date: Jan. 12, 2021

(87) PCT Pub. No.: WO2020/014386
PCT Pub. Date: Jan. 16, 2020

(65) Prior Publication Data
US 2021/0330805 A1    Oct. 28, 2021

Related U.S. Application Data

(60) Provisional application No. 62/697,956, filed on Jul. 13, 2018.

(51) Int. Cl.
| | | |
|---|---|---|
| A61K 47/68 | (2017.01) | |
| A61K 51/04 | (2006.01) | |
| A61P 35/00 | (2006.01) | |
| A61K 51/10 | (2006.01) | |

(52) U.S. Cl.
CPC ...... *A61K 47/6893* (2017.08); *A61K 51/0482* (2013.01); *A61K 51/1045* (2013.01); *A61K 51/1048* (2013.01); *A61K 51/1054* (2013.01); *A61K 51/1063* (2013.01); *A61K 51/1066* (2013.01); *A61K 51/1072* (2013.01); *A61K 51/1093* (2013.01); *A61P 35/00* (2018.01)

(58) Field of Classification Search
None
See application file for complete search history.

(56) References Cited

U.S. PATENT DOCUMENTS

| | | |
|---|---|---|
| 6,982,324 B1 | 1/2006 | Lu et al. |
| 2002/0015705 A1 | 2/2002 | Theodore et al. |
| 2010/0284927 A1 | 11/2010 | Lu et al. |

OTHER PUBLICATIONS

International Search Report and Written Opinion on PCT/US2019/041236 dated Oct. 1, 2019 (11 pages).
Barney Yoo et al: "N Acetylgalactosamino Dendrons as Clearing Agents to Enhance Liver Targeting of Model Antibody-Fusion Protein", Bioconjugate Chemistry, vol. 24, No. 12, Dec. 18, 2013 (Dec. 18, 2013), pp. 2088-2103, XP055224623, ISSN: 1043-1802, DOI: 10.1021/bc400333m.
Cheal Sarah M et al: "Theranostic pretargeted radioimmunotherapy of colorectal cancer xenografts in mice using picomolar affinity 86Y-or 177Lu-DOTA-Bn binding scFv C825/GPA33 IgG bispecific immunoconjugates", European Journal of Nuclear Medicine and Molecular Imaging, vol. 43, No. 5, Nov. 24, 2015 (Nov. 24, 2015), pp. 925-937, XP035871090, ISSN: 1619-7070, DOI: 10.1007/S00259-015-3254-8.
Damian J. Green et al: "Comparative Analysis of Bispecific Antibody and Streptavidin-Targeted Radioimmunotherapy for B-cell Cancers", Cancer Research, vol. 76, No. 22, Sep. 2, 2016 (Sep. 2, 2016), pp. 6669-6679, XP055590462, ISSN: 0008-5472, DOI: 10.1158/0008-5472.CAN-16-0571.
Green Damian J. et al: "A Novel Bispecific CD38 Antibody Eradicates Multiple Myeloma in a Mouse Model Following Yttrium-90-DOTA Capture", BLOOD, vol. 126, No. 23, Dec. 3, 2015 (Dec. 3, 2015), p. 118, XP086645010, ISSN: 0006-4971, DOI: 10.1182/BLOOD.V126.23.118.118.
Kenoyer Aimee L. et al: "Pre-Targeted Radioimmunotherapy Employing a Recombinant Bispecific Antibody Using a Murine Xenograft Model of Human Leukemia", BLOOD, vol. 124, No. 21, Nov. 14, 2014 (Nov. 14, 2014), p. 37 49, XP086744824, ISSN: 0006-4971, DOI: 10.1182/BLOOD.V124.21.3749.3749.
Orozco Johnnie J. et al: "Novel Bispecific Antibody Targeting CD45 and 90Y-DOTA Is Effective Therapy for Acute Myeloid Leukemia in Preclinical Murine Models", BLOOD, vol. 130, Dec. 8, 2017 (Dec. 8, 2017), p. 1355, XP086629435 ISSN: 0006-4971, DOI:10.1182/BLOOD.V130.SUPPL_1.1355.1355.
Park Steven I et al: "Conventional and pretargeted radioimmunotherapy using bismuth-213 to target and treat non-Hodgkin lymphomas expressing CD20: a preclinical model toward optimal consolidation therapy to eradicate minimal residual disease", Blood, vol. 116, No. 20, Nov. 18, 2010 (Nov. 18, 2010), pp. 4231-4239, XP086511520, ISSN: 0006-4971, DOI: 10.1182/BLOOD-2010-05-282327.
Yazaki Paul J et al: "A series of anti-CEA/anti-DOTA bispecific antibody formats evaluated for pretargeting: comparison of tumor uptake and blood clearance", Protein Engineering, Design and Selection, vol. 26, No. 3, Mar. 2013 (Mar. 2013), pp. 187-193, XP002792685, ISSN: 1741-0134, DOI: 10.1093/PROTEIN/GZS096.
Yoo Barney et al: "Glycodendron Clearing Agents for Pretargeting Radioimmunotherapy", Molecular Imaging & BIOLOGY, vol. 14, Sep. 7, 2012 (Sep. 7, 2012), pp. 998-2092, XP055903049, ISSN: 1536-1632, DOI: 10.1007/s11307-012-0598-3.
Yukang Lin et al: "A Genetically Engineered Anti-CD45 Single-Chain Antibody-Streptavidin Fusion Protein for Pretargeted Radioimmunotherapy of Hematologic Malignancies", Cancer Research, vol. 66, No. 7, Apr. 2006 (Apr. 2005), pp. 3884-3892, XP055521262, ISSN: 0008-5472, DOI: 10.1158/0008-5472.CAN-05-3443.

*Primary Examiner* — Jennifer Lamberski
(74) *Attorney, Agent, or Firm* — Foley & Lardner LLP

(57) ABSTRACT

The present disclosure provides compositions and methods for the treatment of cancer. Specifically, the compositions of the present technology include novel clearing agents that may be used in pretargeted radioimmunotherapy.

20 Claims, 12 Drawing Sheets

Figure 2

| Dose of CCA-16-DOTA-$Y^{3+}$ | n | Blood (%ID/g) | Tumor (%ID/g) | Tumor/Blood |
|---|---|---|---|---|
| 0 μg vehicle | 4 | 11.9 ± 0.36 | 34.7 ± 4.04 | 2.9 ± 0.4 |
| 2.5 μg/0.276 nmol | 4 | 11.1 ± 1.15 | 32.5 ± 1.76 | 2.9 ± 0.3 |
| 5 μg/0.552 nmol | 4 | 9.47 ± 0.28*** | 41.2 ± 3.55 | 4.4 ± 0.4 |
| 10 μg/1.10 nmol | 4 | 6.42 ± 1.25** | 31.5 ± 6.34 | 4.9 ± 1.4 |
| 15 μg/1.65 nmol | 4 | 1.27 ± 0.21*** | 33.3 ± 4.42 | 26.3 ± 5.5 |
| 20 μg/2.21 nmol | 4 | 0.46 ± 0.13*** | 27.2 ± 5.17 | 59.2 ± 20.0 |
| 25 μg/2.76 nmol | 3 | 0.40 ± 0.18*** | 30.8 ± 5.07 | 76.4 ± 36.2 |
| | | | | |
| Dextran-CA 62.5 μg/0.125 nmol dextran/7.625 nmol (Y)DOTA | 4 | 0.45 ± 0.09*** | 34.6 ± 4.50 | 77.3 ± 19.2 |

\*\*\**P* <0.001 compared with vehicle
\*\**P* <0.01 compared with vehicle
\**P* <0.05 compared with vehicle
CA = clearing agent

Figure 3

| Dose of CCA-16-DOTA-Y$^{3+}$ | n | Blood (%ID/g) | Tumor (%ID/g) | Tumor/Blood |
|---|---|---|---|---|
| 25 µg | 4 | 0.60 ± 0.04 | 18.9 ± 2.23 | 31.3 ± 4.3 |
| 30 µg | 3 | 0.62 ± 0.15 | 15.4 ± 1.78 | 24.7 ± 6.4 |
| 35 µg | 3 | 0.34 ± 0.03** | 17.0 ± 1.82 | 50.1 ± 7.2 |
| 40 µg | 3 | 0.28 ± 0.03** | 13.8 ± 1.16 | 49.3 ± 7.4 |

Figure 4

| Organ | 0 µg vehicle (n = 4) 24 h p.i. | 25 µg Dendron-CA (n = 3) 24 h p.i. | 62.5 µg Dextran-CA (n = 4) 24 h p.i. |
|---|---|---|---|
| Blood | 11.89 ± 0.36 | 0.40 ± 0.18 | 0.45 ± 0.09 |
| SW1222 tumor | 34.69 ± 4.04 | 30.80 ± 5.07 | 34.60 ± 4.50 |
| Heart | 3.93 ± 0.26 | 0.16 ± 0.07 | 0.10 ± 0.05 |
| Lungs | 3.18 ± 0.46 | 0.39 ± 0.06 | 0.51 ± 0.07 |
| Liver | 5.31 ± 0.80 | 0.31 ± 0.11 | 0.51 ± 0.09 |
| Spleen | 3.42 ± 0.47 | 0.10 ± 0.07 | 0.52 ± 0.17 |
| Stomach | 1.17 ± 0.14 | 0.02 ± 0.01 | 0.01 ± 0.00 |
| Small Intestine | 1.34 ± 0.11 | 0.07 ± 0.02 | 0.06 ± 0.02 |
| Large Intestine | 0.97 ± 0.21 | 0.13 ± 0.02 | 0.15 ± 0.01 |
| Kidneys | 2.86 ± 0.81 | 0.69 ± 0.14 | 0.63 ± 0.09 |
| Muscle | 0.97 ± 0.36 | 0.00 ± 0.00 | 0.07 ± 0.05 |
| Bone | 1.93 ± 0.14 | 0.00 ± 0.00 | 0.00 ± 0.00 |
| *Tumor-to-tissue ratios* | | | |
| Blood | 2.9 ± 0.4 | 76.4 ± 36.2 | 77.3 ± 19.2 |
| Heart | 8.8 ± 1.2 | 189 ± 91.2 | 364 ± 212 |
| Lungs | 10.9 ± 2.0 | 79.7 ± 17.4 | 67.8 ± 12.5 |
| Liver | 6.5 ± 1.2 | 99.4 ± 38.0 | 67.5 ± 15.1 |
| Spleen | 10.1 ± 1.8 | 298 ± 220 | 66.5 ± 23.4 |
| Stomach | 29.6 ± 4.9 | 1320 ± 435 | 3460 ± 1482 |
| Small Intestine | 25.9 ± 3.7 | 440.0 ± 120.3 | 602 ± 225 |
| Large Intestine | 35.8 ± 8.9 | 236.9 ± 47.9 | 231 ± 34.3 |
| Kidneys | 12.1 ± 2.2 | 44.9 ± 12.0 | 54.7 ± 10.3 |
| Muscle | 35.9 ± 7.9 | | 494 ± 355 |
| Bone | 20.3 ± 2.6 | | |

Figure 6(A)

| Organ | Pretargeted [$^{111}$In]1 ($n = 4$) 172 pmol/1.67 MBq [45 $\mu$Ci] 24 h p.i. | Pretargeted [$^{111}$In]1 ($n = 1$) 790 pmol/7.67 MBq [207 $\mu$Ci] 24 h p.i. |
|---|---|---|
| Blood | 0.76 ± 0.19 | 0.16 |
| SW1222 tumor | 13.19 ± 1.94 | 6.70 |
| Heart | 0.28 ± 0.04 | 0.09 |
| Lungs | 0.40 ± 0.07 | 0.17 |
| Liver | 0.47 ± 0.10 | 0.22 |
| Spleen | 0.29 ± 0.06 | 0.10 |
| Stomach | 0.09 ± 0.03 | 0.03 |
| Small Intestine | 0.12 ± 0.02 | 0.06 |
| Large Intestine | 0.19 ± 0.08 | 0.06 |
| Kidneys | 1.02 ± 0.19 | 0.65 |
| Muscle | 0.12 ± 0.02 | 0.04 |
| Bone | 0.16 ± 0.03 | 0.05 |
| *Tumor-to-tissue ratios* | | |
| Blood | 17.3 ± 4.4 | 41.1 |
| Heart | 47.5 ± 12.1 | 75.3 |
| Lungs | 33.4 ± 8.5 | 40.5 |
| Liver | 28.4 ± 7.2 | 31.2 |
| Spleen | 45.1 ± 11.4 | 65.8 |
| Stomach | 155.1 ± 39.8 | 229 |
| Small Intestine | 107.6 ± 27.5 | 110 |
| Large Intestine | 70.3 ± 18.9 | 119 |
| Kidneys | 12.9 ± 3.3 | 10 |
| Muscle | 112.2 ± 28.5 | 162 |
| Bone | 85.1 ± 21.7 | 127 |

Figure 6(B)

| Organ | Pretargeted [$^{225}$Ac]1 (n = 3) 182 pmol/1.85 kBq [50 nCi] | Pretargeted [$^{111}$In]1 (n = 4) 172 pmol/1.67 MBq [45 µCi] | $p$-value |
|---|---|---|---|
| Blood | 0.94 ± 0.26[a] | 0.76 ± 0.19 | 0.385 |
| SW1222 Tumor | 16.71 ± 2.95 | 13.19 ± 1.94 | 0.475 |
| Heart | 0.28 ± 0.28 | 0.28 ± 0.04 | 0.242 |
| Lungs | 0.70 ± 0.67 | 0.40 ± 0.07 | 0.202 |
| Liver | 1.40 ± 0.82 | 0.47 ± 0.10 | 0.066 |
| Spleen | 0.54 ± 0.93 | 0.29 ± 0.06 | 0.256 |
| Stomach | 0.07 ± 0.08 | 0.09 ± 0.03 | 0.448 |
| Small Intestine | 0.16 ± 0.18 | 0.12 ± 0.02 | 0.305 |
| Large Intestine | 0.11 ± 0.12 | 0.19 ± 0.08 | 0.264 |
| Kidneys | 1.08 ± 0.55 | 1.02 ± 0.19 | 0.374 |
| Muscle | 0.13 ± 0.23 | 0.12 ± 0.02 | 0.378 |
| Bone | [b] | 0.16 ± 0.03 | |

Figure 9

| Tissue | $^{177}$Lu-activity at 1 h p.i. (%ID/g) | $^{177}$Lu-activity at 4 h p.i. (%ID/g) | $^{177}$Lu-activity at 24 h p.i. (%ID/g) | $^{177}$Lu-activity at 48 h p.i. (%ID/g) |
|---|---|---|---|---|
| Blood | 1.93 ± 0.17 | 1.99 ± 0.47 | 1.27 ± 0.45 | 0.39 ± 0.10 |
| Tumor | 24.22 ± 3.50 | 26.87 ± 4.53 | 27.40 ± 4.17 | 18.24 ± 2.89 |
| Heart | 0.94 ± 0.22 | 0.81 ± 0.13 | 0.51 ± 0.17 | 0.26 ± 0.16 |
| Lung | 1.43 ± 0.23 | 1.40 ± 0.30 | 0.97 ± 0.33 | 0.53 ± 0.24 |
| Liver | 1.31 ± 0.17 | 0.90 ± 0.19 | 0.75 ± 0.20 | 0.48 ± 0.09 |
| Spleen | 0.61 ± 0.08 | 0.64 ± 0.18 | 0.47 ± 0.12 | 0.29 ± 0.07 |
| Stomach | 0.73 ± 1.21 | 0.12 ± 0.04 | 0.13 ± 0.04 | 0.06 ± 0.03 |
| Small Intestine | 0.87 ± 0.51 | 0.23 ± 0.04 | 0.19 ± 0.04 | 0.08 ± 0.01 |
| Large Intestine | 0.11 ± 0.02 | 0.83 ± 0.13 | 0.24 ± 0.02 | 0.16 ± 0.01 |
| Kidneys | 1.31 ± 0.11 | 1.35 ± 0.21 | 1.00 ± 0.20 | 0.70 ± 0.12 |
| Muscle | 0.65 ± 0.24 | 0.56 ± 0.28 | 0.22 ± 0.08 | 0.13 ± 0.02 |
| Bone | 0.56 ± 0.16 | 0.24 ± 0.05 | 0.25 ± 0.07 | 0.12 ± 0.03 |

Figure 11

| Tissue | Absorbed dose (cGy/MBq) | Therapeutic index |
|---|---|---|
| Blood | 11.7 | 40 |
| Tumor | 468.4 | --- |
| Heart | 2.66 | 176 |
| Lung | 10.7 | 44 |
| Liver | 9.97 | 47 |
| Spleen | 5.49 | 85 |
| Stomach | 0.86 | 545 |
| Small Intestine | 1.16 | 404 |
| Large Intestine | 1.87 | 250 |
| Kidneys | 13.3 | 35 |
| Muscle | 3.73 | 126 |
| Bone | 3.68 | 127 |

N-ACETYLGALACTOSAMINO DENDRON-CLEARING AGENT FOR DOTA-PRETARGETED RADIOIMMUNOTHERAPY

CROSS-REFERENCE TO RELATED PATENT APPLICATIONS

This application is a US National Stage Application under 35 U.S.C. § 371 of PCT Patent Application No. PCT/US2019/041236, filed on Jul. 10, 2019, which claims the benefit of and priority to U.S. Provisional Appl. No. 62/697,956, filed Jul. 13, 2018, the disclosure of each of which is incorporated by reference herein in its entirety.

STATEMENT OF GOVERNMENT SUPPORT

This invention was made with government support under CA086438 awarded by the National Institutes of Health. The government has certain rights in the invention.

TECHNICAL FIELD

The present technology relates generally to compositions including novel N-acetylgalactosamino dendron-clearing agents and methods of using the same in pretargeted radioimmunotherapy.

BACKGROUND

The following description of the background of the present technology is provided simply as an aid in understanding the present technology and is not admitted to describe or constitute prior art to the present technology.

Radiolabeled agents have been used as delivery vehicles of ionizing radiation to specific disease sites for over 50 years (Larson S M. *Cancer* 67:1253-1260 (1991); Britton K E. *Nucl Med Commun.* 18:992-1007 (1997)). A large number of molecules have been considered for targeted delivery of radioisotopes, including radiolabeled antibodies, antibody fragments, alterative scaffolds, and small molecules (Tolmachev V, et al. *Cancer Res.* 67:2773-2782 (2007); Birchler M T, et al., *Otolaryngol Head Neck Surg.* 136:543-548 (2007); Reubi J C, Maecke H R. *J Nucl Med.* 49:1735-1738 (2008)). Using antibodies to target poisons to tumors, e.g., radioimmunotherapy (RIT) with directly conjugated antibodies, has been challenging due in part to suboptimal tumor dose and therapeutic index (TI). Further, because of normal tissue bystander toxicity, dose escalation is not feasible and therefore such therapy results in limited anti-tumor effect. Moreover, antibodies exhibit long half-lives in the blood resulting in low tumor-to-background ratios. Antibody fragments and other smaller binding scaffolds exhibit faster blood clearance, but result in high kidney and/or liver uptake. Radiolabeled small molecule ligands generally exhibit more rapid blood clearance and lower background compared to antibodies and antibody fragments, but usually result in poor specificity due to relatively low affinities for the desired target.

In pretargeted radioimmunotherapy (PRIT), a nonradioactive bifunctional antibody with specificity for both a tumor antigen and a small molecule hapten is administered and allowed to localize to the tumor(s). After sufficient blood clearance of the antibody, a radiolabeled small molecule is administered and is captured by the pretargeted antibody. However, many small peptide and metal chelate haptens used in PRIT systems exhibit significant whole-body retention, which results in unwanted background activity that limits signal-to-background ratios for imaging and contributes to nonspecific radiation that limits the maximum tolerated dose for therapy applications (Orcutt el al., *Mol Imaging Biol* 13:215-221 (2011)).

Thus, there is a need for novel molecules that permit (a) efficient pretargeted radioimmunotherapy of solid tumors in vivo and (b) rapid clearance of radiolabeled small molecules from non-tumor tissue.

SUMMARY OF THE PRESENT TECHNOLOGY

In an aspect, the present technology provides a compound that is

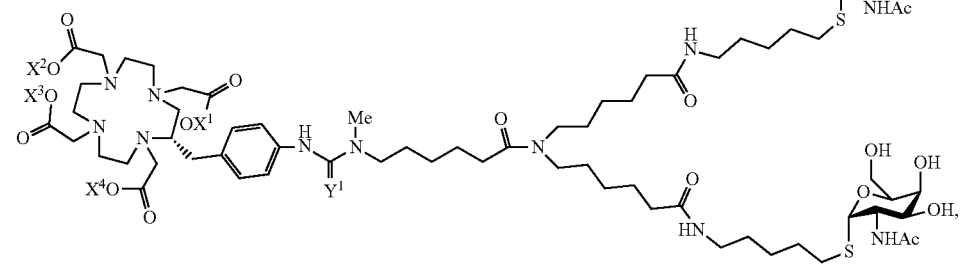

-continued
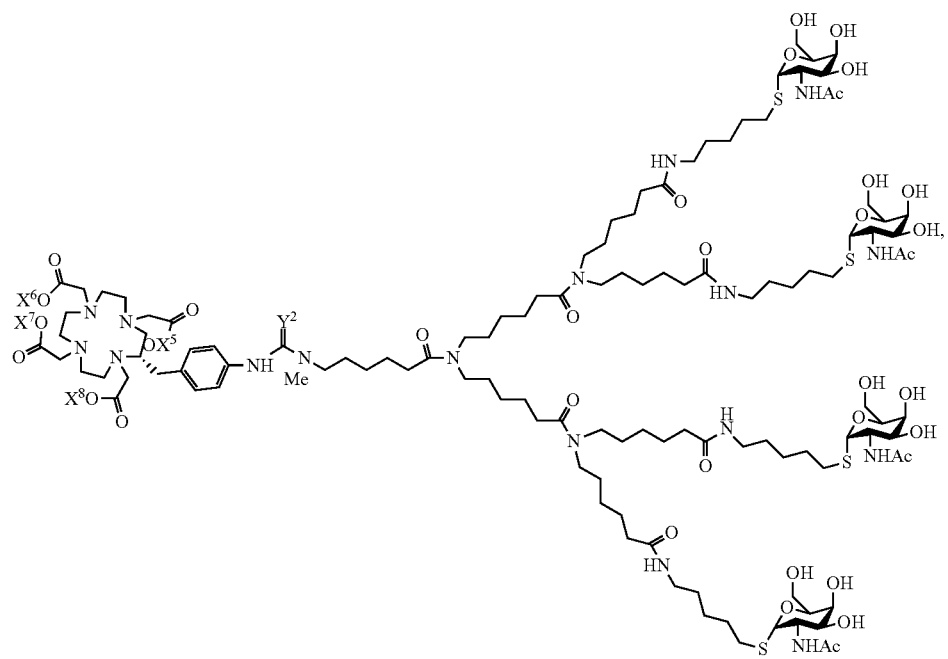

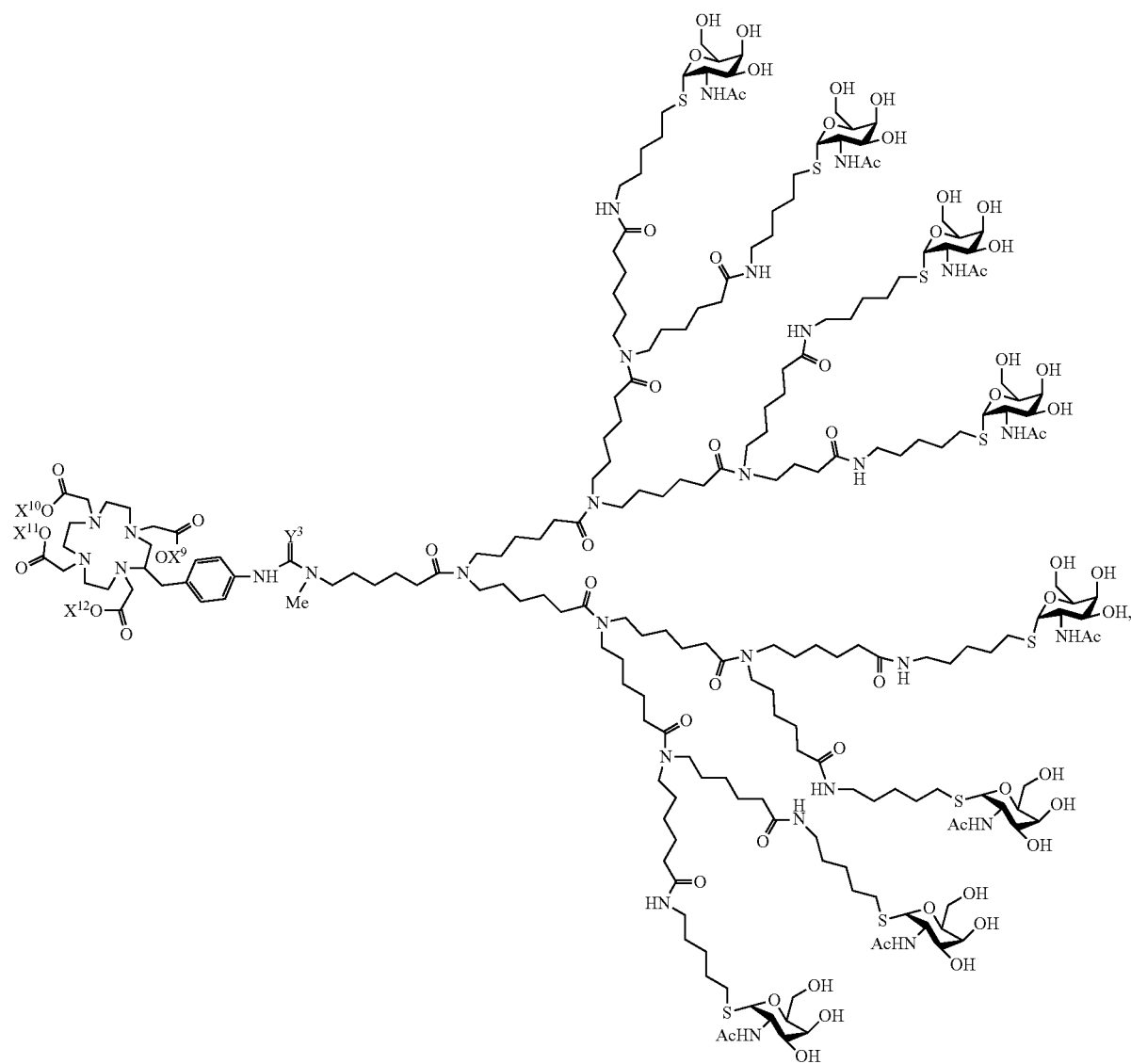

-continued
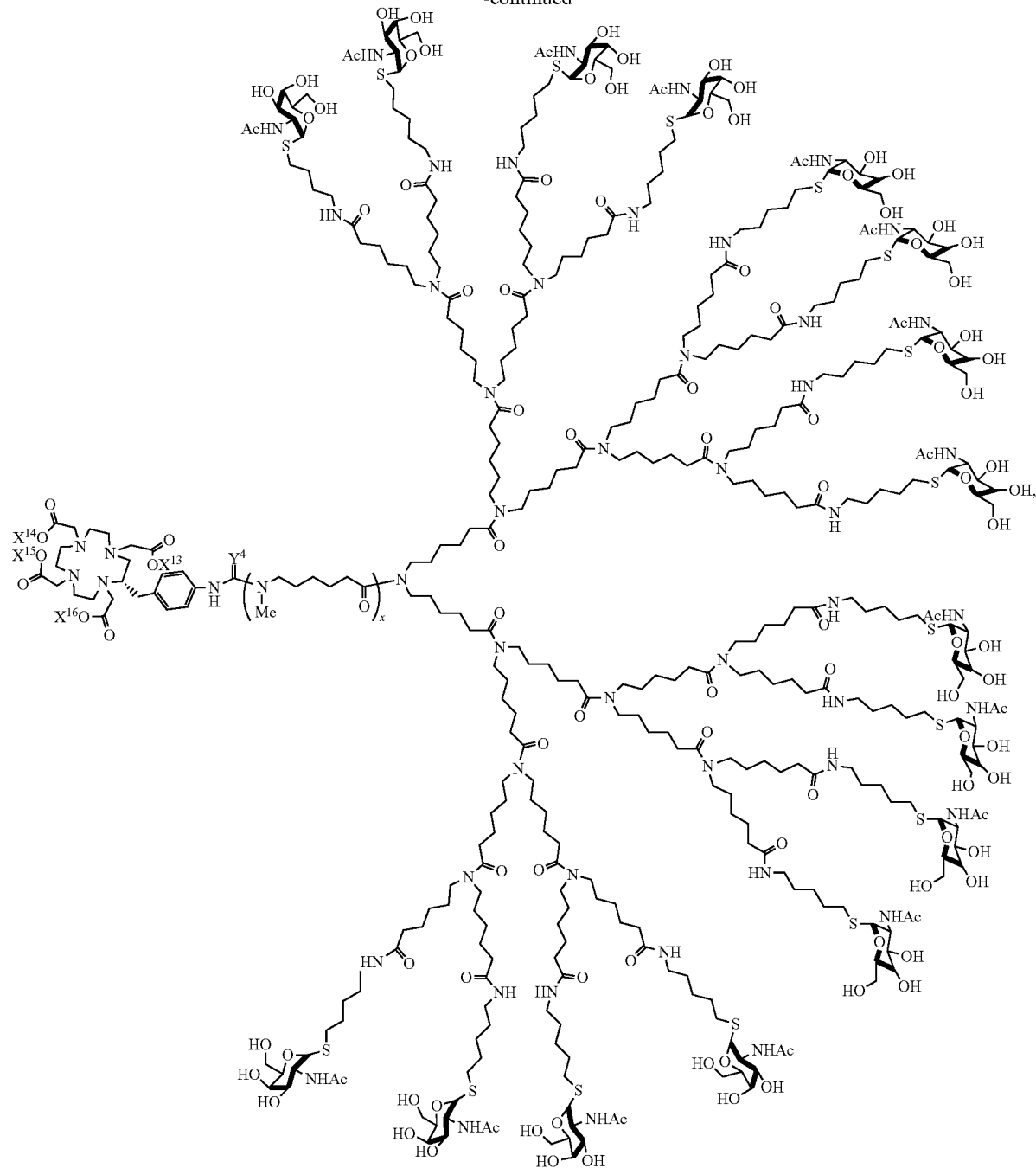

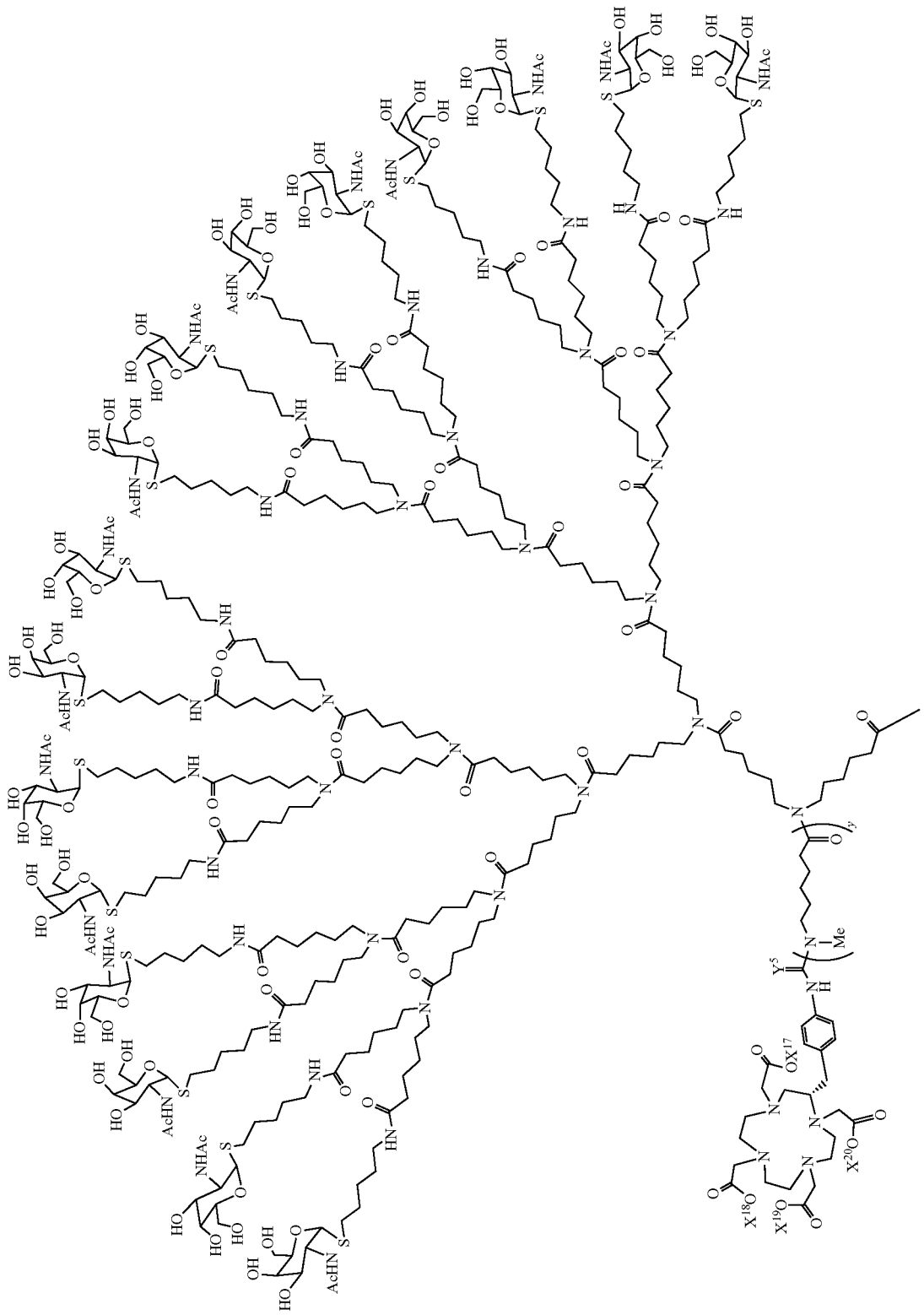

-continued
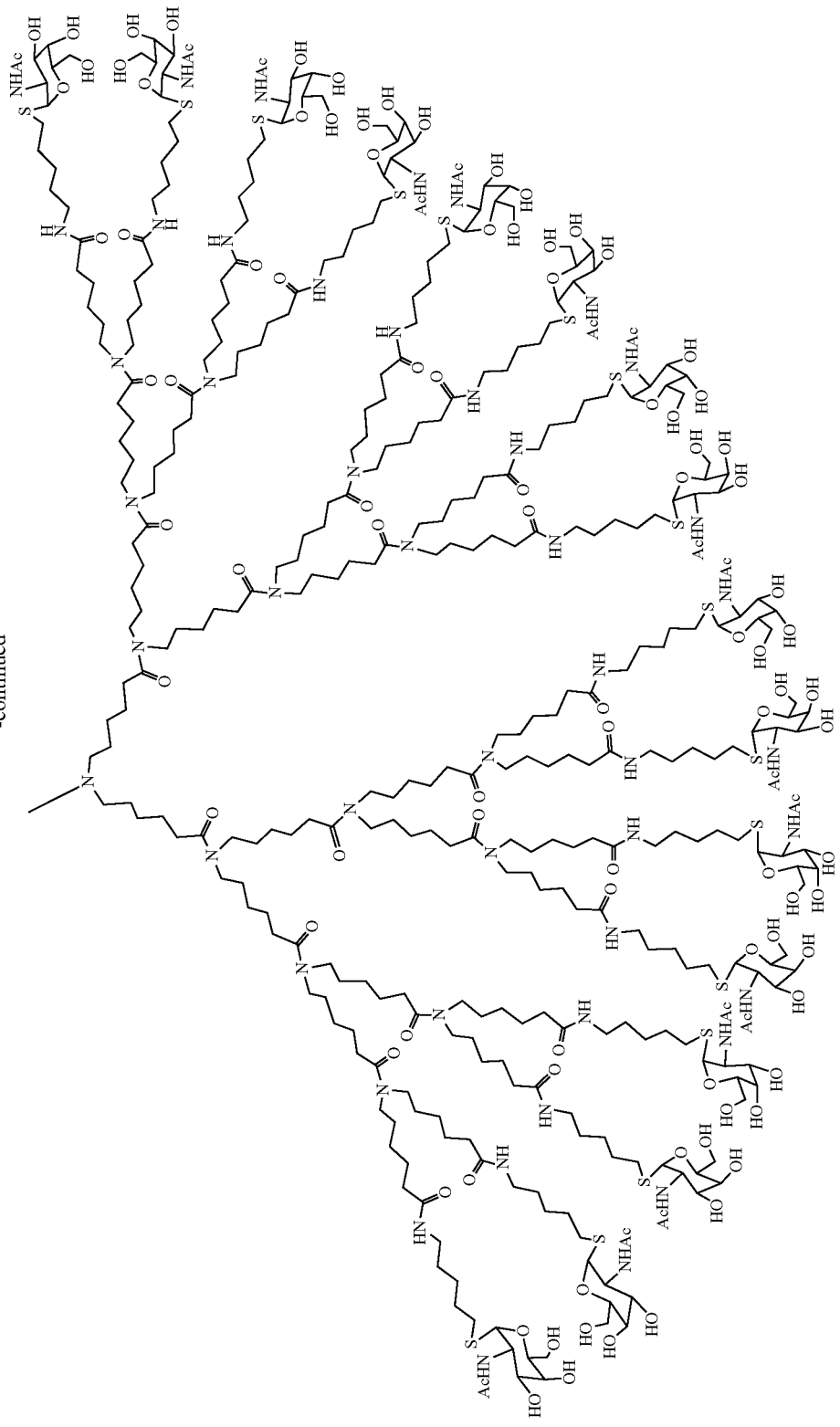

or a pharmaceutically acceptable salt and/or solvate thereof, where $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, and $X^{20}$ are each independently H or a lone pair of electrons (i.e. providing an oxygen anion); $Y^1$, $Y^2$, $Y^3$, $Y^4$, and $Y^5$ are each independently O or S; x is 1, 2, or 3; and y is 1, 2, 3, or 4.

In any embodiment herein, the compound may be a clearing agent that is

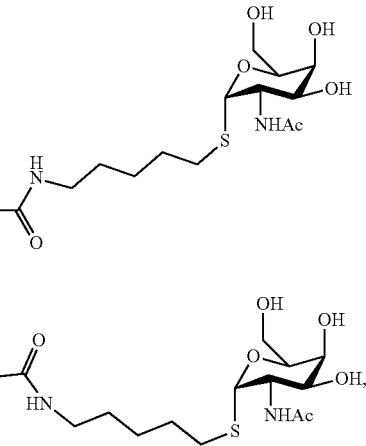

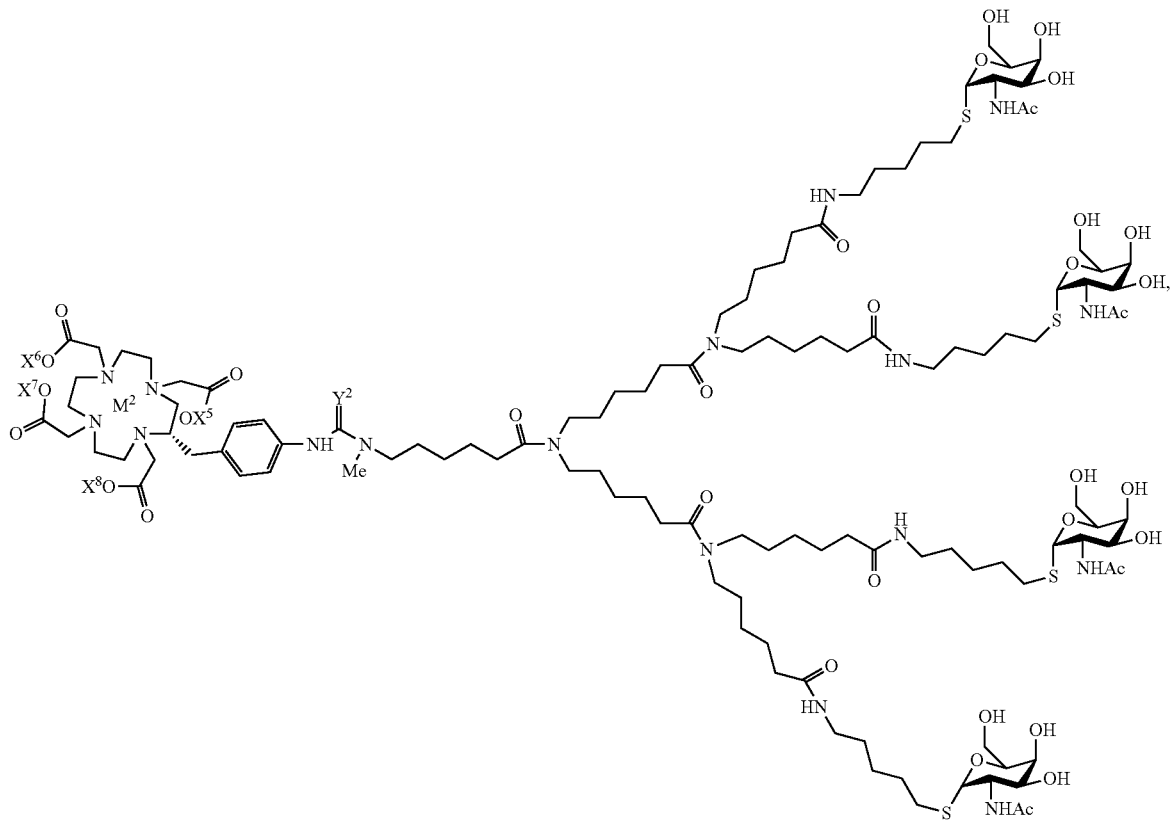

-continued
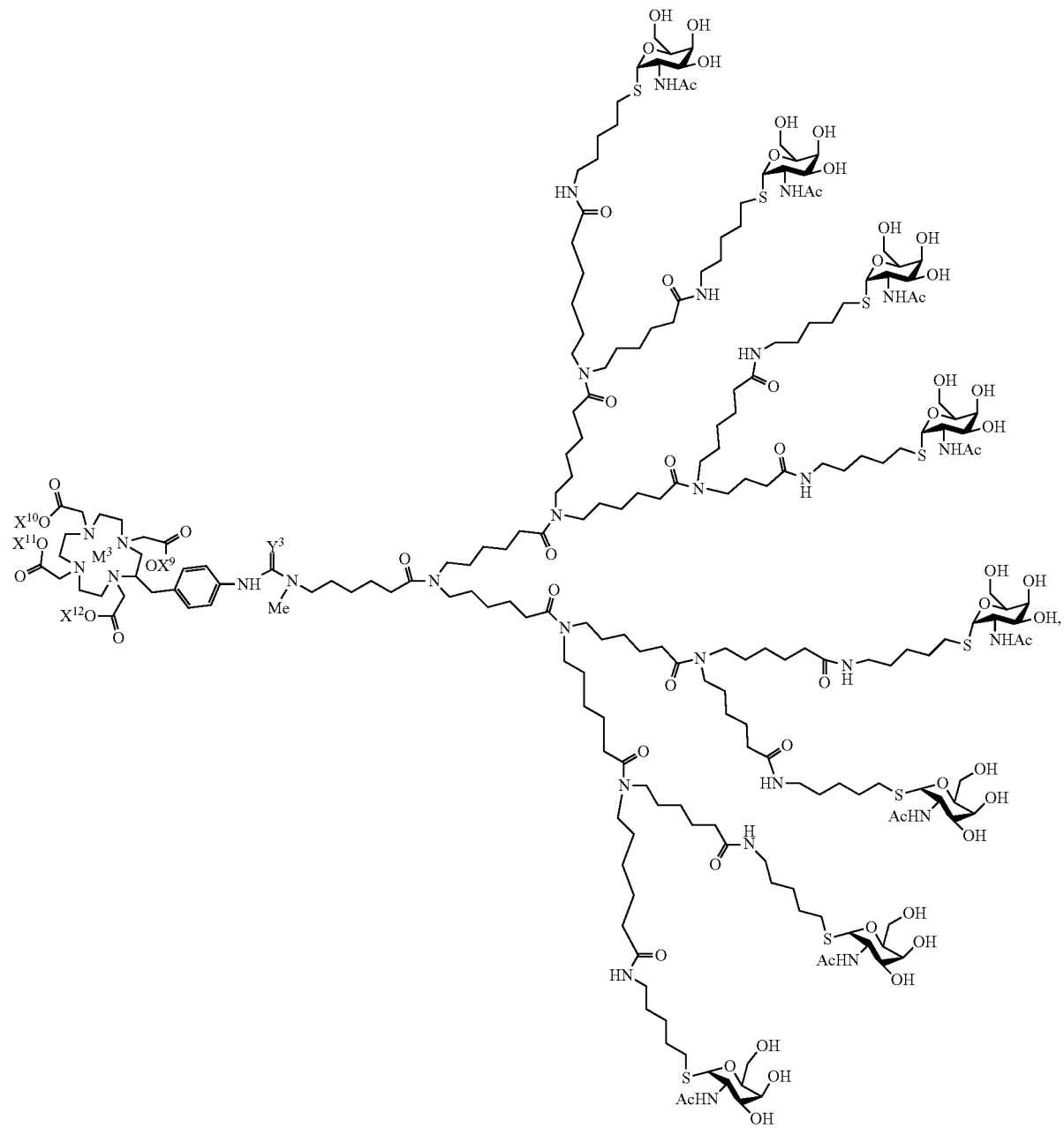

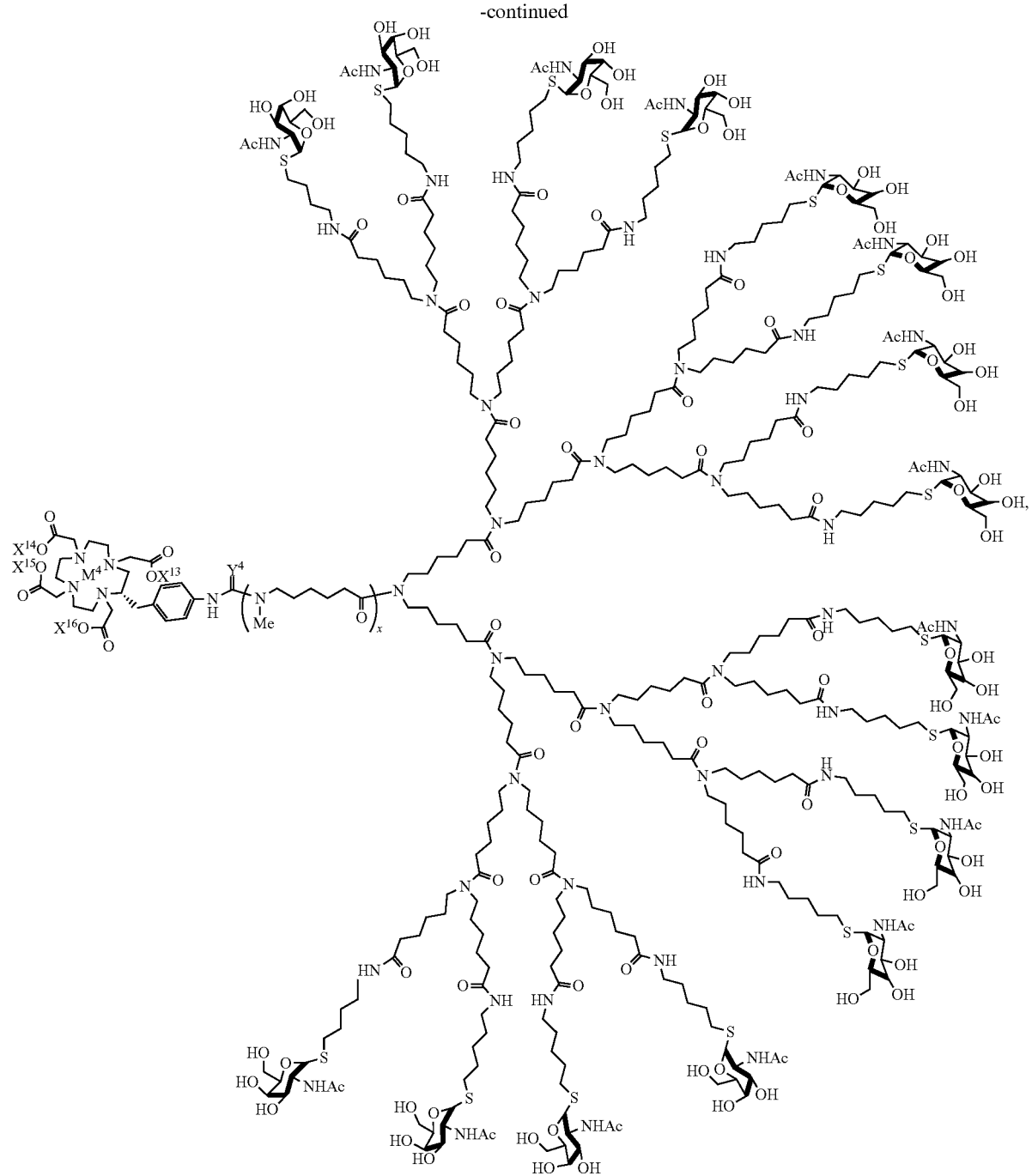

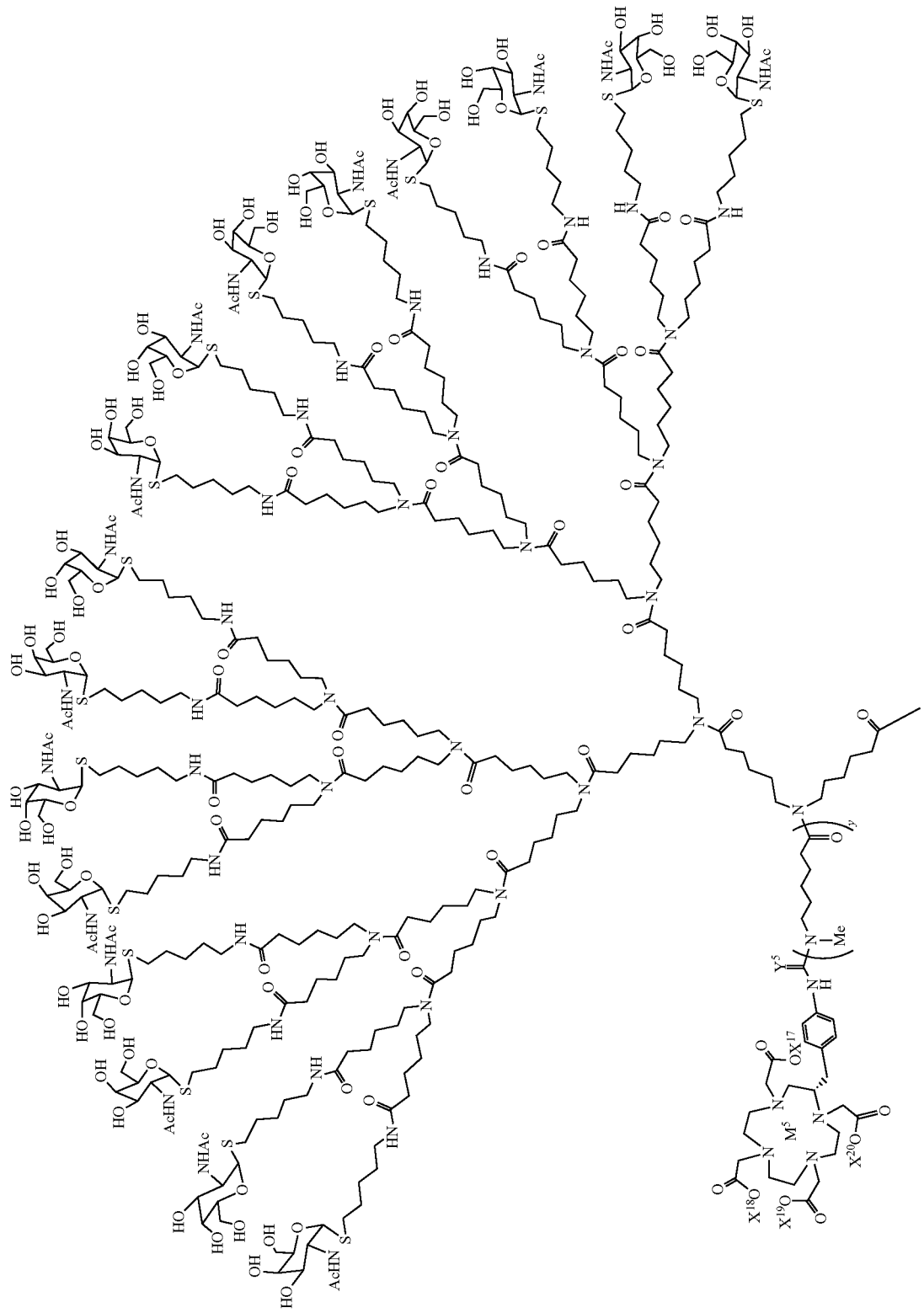

-continued
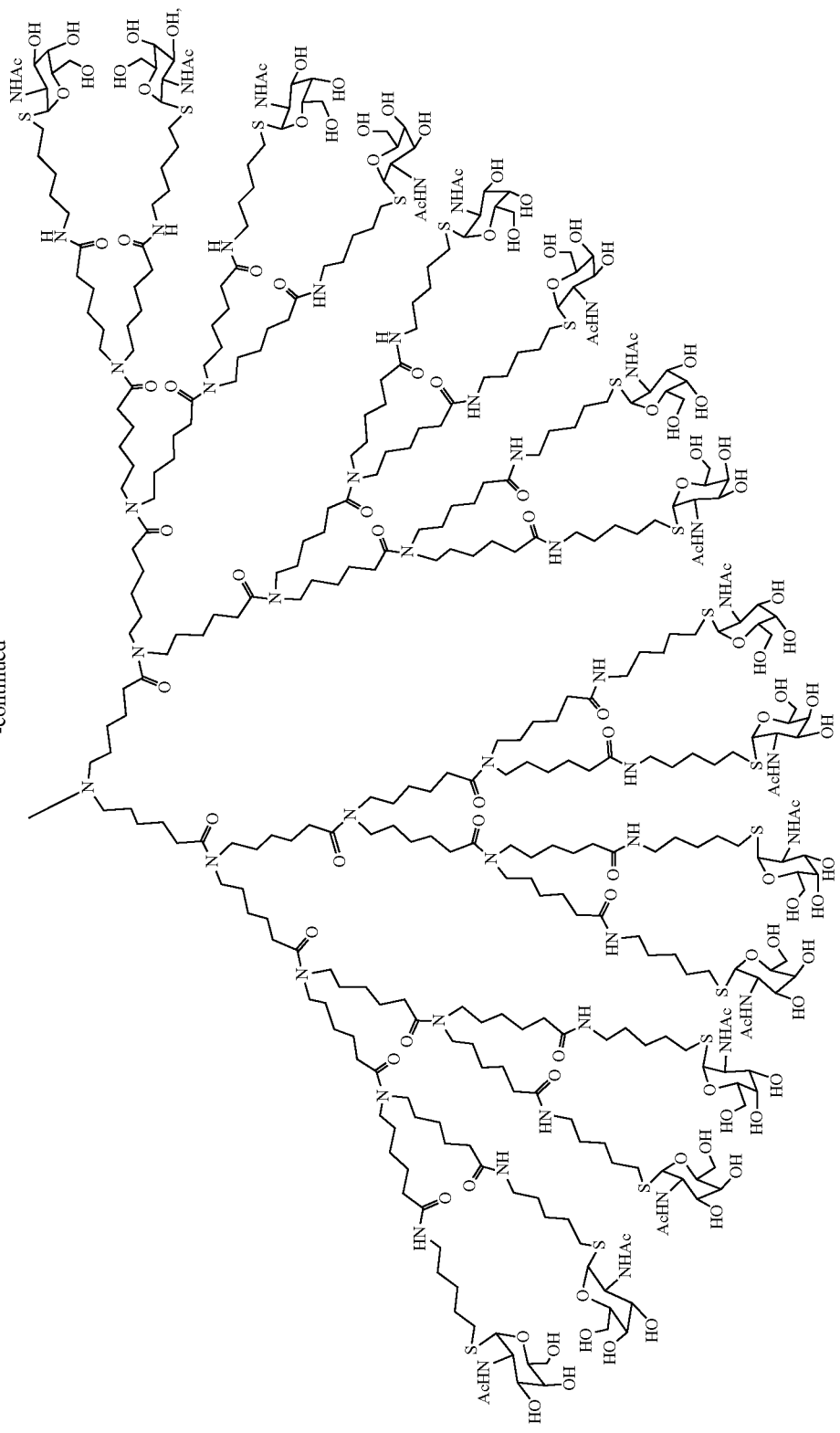

or a pharmaceutically acceptable salt and/or solvate thereof, wherein $M^1$, $M^2$, $M^3$, $M^4$, and $M^5$ are each independently $Lu^{3+}$, $Sc^{3+}$, $Ga^{3+}$, $Y^{3+}$, $In^{3+}$, $La^{3+}$, $Ce^{3+}$, $Eu^{3+}$, $Tb^{3+}$, or $Gd^{3+}$; $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, and $X^{20}$ are each independently H or a lone pair of electrons (i.e. providing an oxygen anion); Y, $Y^2$, $Y^3$, $Y^4$, and $Y^5$ are each independently O or S; x is 1, 2, or 3; and y is 1, 2, 3, or 4.

In any embodiment herein, it may be that $M^1$, $M^2$, $M^3$, $M^4$, and $M^5$ are each independently not a radionuclide. In any embodiment herein, it may be that $Y^1$, $Y^2$, $Y^3$, $Y^4$ and $Y^5$ are each independently S. In any embodiment herein, it may be that x is 1 or 2. In any embodiment herein, it may be that y is 2 or 3.

In a related aspect, a composition is provided that includes one or more of any embodiment of a compound as described above along with a pharmaceutically acceptable carrier.

In another aspect, the present disclosure provides a method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; (b) administering an effective amount of a clearing agent of the present technology to the subject; and (c) administering an effective amount of a radiolabeled DOTA hapten to the subject, wherein the DOTA hapten is configured to form a complex with the anti-DOTA bispecific antibody.

In another aspect, the present disclosure provides a method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; (b) administering an effective amount of a clearing agent of the present technology to the subject; and (c) administering an effective amount of a radiolabeled DOTA hapten to the subject, wherein the DOTA hapten is configured to form a complex with the anti-DOTA bispecific antibody. The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

Additionally or alternatively, in some embodiments of the methods disclosed herein, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

Additionally or alternatively, in some embodiments of the methods disclosed herein, the anti-DOTA bispecific antibody, the clearing agent, and/or the radiolabeled DOTA hapten is administered intravenously, intramuscularly, intraarterially, intrathecally, intracapsularly, intraorbitally, intradermally, intraperitoneally, transtracheally, subcutaneously, intracerebroventricularly, orally or intranasally.

Additionally or alternatively, in some embodiments of the methods disclosed herein, the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer. The brain cancer may be a pituitary adenoma, a meningioma, a neuroblastoma, or a craniopharyngioma.

Additionally or alternatively, in some embodiments of the methods disclosed herein, the radiolabeled DOTA hapten comprises one or more of Proteus-DOTA, S-2-(R-aminobenzyl)-1,4,7,10-tetraazacyclododecane tetra-acetic acid (DOTA-Bn), DOTA-Bn-biotin, BAD (((S)-2-(4-(2-bromo)-acetamido)-benzyl)-DOTA), NBD ((S)-2-(4-nitrobenzyl)-DOTA), DOTA-RGD, DOTA-PEG-E(c(RGDyK))$_2$, DOTA-8-AOC-BBN, p-N02-Bn-DOTA, DOTA-PESIN, DOTA-biotin-sarcosine (DOTA-biotin), 1,4,7,10-tetraazacyclododecane-1,4,7,10-tetraacetic acid mono (N-hydroxysuccinimide ester) (DOTA-NHS), or DOTATyr-LysDOTA. The radiolabeled DOTA hapten may be labelled with a radionuclide selected from the group consisting of $^{213}Bi$, $^{211}At$, $^{225}Ac$, $^{152}Dy$, $^{212}Bi$, $223Ra$, $^{219}Rn$, $^{215}Po$, $^{211}Bi$, $^{221}Fr$, $^{217}At$, $^{255}Fm$, $^{86}Y$, $^{90}Y$, $^{89}Sr$, $^{165}Dy$, $^{186}Re$, $^{188}Re$, $^{177}Lu$, $^{67}Cu$, $^{111}In$, $^{67}Ga$, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, $^{203}Pb$, $^{68}Ga$, $^{227}Th$, and $^{64}Cu$.

Additionally or alternatively, in some embodiments of the methods disclosed herein, the radioactive levels emitted by the radiolabeled DOTA hapten-anti-DOTA bispecific antibody complex are detected between 4 to 24 hours after the radiolabeled DOTA hapten is administered. The radioactive levels emitted by the complex may be expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, J Nucl Med. 45(9):1431-4 (2004). The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1. Additionally or alternatively, in some embodiments of the methods disclosed herein, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Also disclosed herein are kits containing components suitable for treating cancer in a patient. In one aspect, the kits comprise a clearing agent of the present technology and instructions for use. The kits of the present technology may further comprise at least one anti-DOTA BsAb and/or a DOTA hapten that is optionally labeled with one or more radionuclides. Examples of suitable radionuclides include but are not limited to $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Pt, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, and $^{64}$Cu. Additionally or alternatively, in some embodiments, the at least one anti-DOTA BsAb binds to a tumor antigen target selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), 0-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, PIGF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

BRIEF DESCRIPTION OF THE DRAWINGS

FIG. 2 shows the tumor pretargeting results achieved with CCA-16-DOTA-Y$^{3+}$, a clearing agent of the present technology.

FIG. 3 shows the dose-dependent effects of CCA-16-DOTA-Y$^{3+}$ on tumor uptake. **P<0.01 compared with the 25 µg group.

FIG. 4 shows a comparison of the tumor pretargeting results achieved with an embodiment of a clearing agent of the present technology compared with no clearing agent (vehicle) as well as with a 500kD dextran-DOTA hapten conjugate clearing agent.

FIG. 6(A) shows the tumor pretargeting results achieved in animals injected with 172 pmol/1.67 MBq [45 µCi] of [$^{111}$In] Proteus-DOTA (n=4) or 790 pmol/7.66 MBq [207 µCi] of [$^{111}$In] Proteus-DOTA (n=1).

FIG. 6(B) shows a statistical comparison of [$^{225}$Ac] Proteus-DOTA and [$^{111}$In]Proteus-DOTA pretargeting with anti-GPA33-DOTA-PRIT.

FIG. 9 shows the $^{177}$Lu activity in tumor and various normal tissues determined using a biodistribution assay following PRIT with huA33-C825 (0.25 mg/mouse) and dendron-clearing agent CCA-16-DOTA-Y$^{3+}$ (25 µg; 2.76 nmol) and 3.7 MBq (20 pmol) of $^{177}$Lu-aminobenzylDOTA ([$^{177}$Lu]LuDOTA-Bn). n=5 animals/group; data is presented as % ID/g, average±1 SD.

FIG. 11 shows the absorbed doses for pretargeting of [$^{177}$Lu]LuDOTA-Bn anti-GPA33-DOTA-PRIT with dendron-clearing agent CCA-16-DOTA-Y$^{3+}$ in nude mice carrying s.c. GPA33(+) SW1222 tumors. The therapeutic index was defined as estimated tumor/normal tissues absorbed dose ratio.

DETAILED DESCRIPTION

Figure 1:
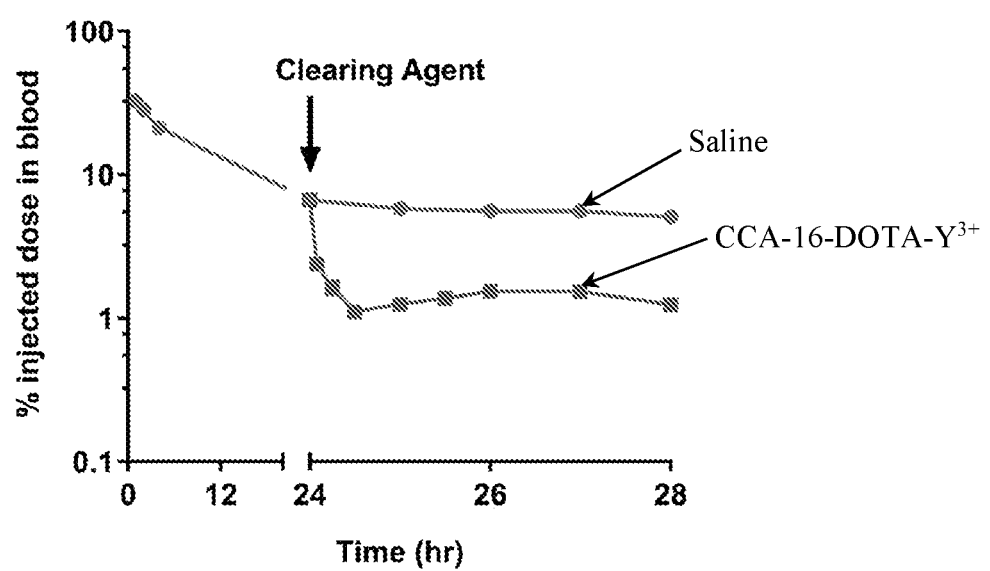
FIG. 1 shows the effect of the clearing agent disclosed herein on circulating $^{131}$I-BsAb in vivo. Athymic normal (tumor-free) mice were intraveneously injected a t=0 with $^{131}$I-BsAb (19-21 µCi; 250 µg, 1.19 nmol), followed with either vehicle (saline) or dendron-clearing agent (25 µg; 2.76 nmol) at t=24 hours. Serial blood sampling was conducted at various time points from t=1-28 hours. Data is presented as average±standard error of the mean.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series Methods in Enzymology (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) Nucleic Acid Hybridization; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

Clearing agents (CA) are a class of compounds designed to rapidly remove targeting biomolecules from circulation during pretargeting of radioisotopes to tumor-antigens. Dextran-based clearing agents are generally used for high-therapeutic index DOTA-based pretargeted radioimmunotherapy (DOTA PRIT). Although highly effective as a clearing agent scaffold, dextrans present dosing challenges due to their inherent polydispersity and kinetics of enzymatic degradation in vivo.

The DOTA-PRIT platform disclosed herein entails a three-step pretargeting strategy including the administration of (1) an IgG-single chain variable fragment (scFv) bispecific antibody construct (IgG-scFv) comprising antibody sequences with high affinity for an anti-tumor antigen antibody (the IgG-portion) and an anti-DOTA-hapten single chain variable fragment scFv (e.g., "C825"), (2) a clearing agent of the present technology to rapidly reduce circulating BsAb after sufficient time is given for the BsAb to accumulate at an antigen-positive tumor, and (3) a radiolabeled DOTA hapten composition (e.g., $^{177}$Lu-DOTA-Bn).

The compositions of the present technology include novel N-acetylgalactosamino dendron-clearing agents that are useful in PRIT (e.g., alpha-particle radioimmunotherapy). The clearing agent compositions disclosed herein exhibit enhanced blood clearance of DOTA-PRIT radiolabeled bispecific antibody (BsAb) and improve therapeutic index (TI) during DOTA-PRIT. For example, within 5 minutes of administration of a single dose of an excess dendron-clearing agent of the present technology (molar ratio of injected $^{131}$I-BsAb to CA of 1:2.3), the $^{131}$I-activity dropped in blood by 64% from baseline of 6.7% ID/g to 2.4% ID/g. DOTA-PRIT studies in a mouse xenograft model of human colorectal cancer showed CA-dose dependent tumor-to-blood uptake ratios of $^{177}$Lu-DOTA-Bn at 24 hours post injection of $^{177}$Lu-activity (e.g., average tumor-to-blood ratios were 2.9, 26, and 59 for 0 µg (vehicle), 15 µg, or 20 µg of dendron-CA, respectively). A 25 µg dose of dendron-CA resulted in an average tumor-to-blood ratio of 76, almost identical to previously optimized dosing with dextran-CA (average tumor-to-blood ratio of 77). Collectively, these results suggest that the dendron-clearing agent of the present technology is a suitable for high TI DOTA-PRIT.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes "intact immunoglobulins") and "antigen binding fragments" specifically bind to a molecule of interest (or a group of highly similar molecules of interest) to the substantial exclusion of binding to other molecules (for example, antibodies and antibody fragments that have a binding constant for the molecule of interest that is about $10^3$ M$^1$ times greater, about $10^4$ M$^{-1}$ times greater or about $10^5$ M$^{-1}$ times greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, 3$^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy (VH) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a target protein (e.g., GPA33) or molecule (e.g., DOTA or a DOTA hapten) will have a specific $V_H$ region and $V_L$ region sequence, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Examples of antibodies include monoclonal antibodies, polyclonal antibodies, humanized antibodies, chimeric antibodies, recombinant antibodies, multispecific antibodies, bispecific antibodies, and antibody fragments. An antibody specifically binds to an antigen.

A "bispecific antibody" is an antibody that can bind simultaneously to two different antigens. Bispecific antibodies (BsAb) and bispecific antibody fragments (BsFab) may have at least one arm that specifically binds to, for example, a tumor-associated antigen (e.g., GPA33) and at least one other arm that specifically binds to a targetable conjugate that bears a therapeutic or diagnostic agent (e.g., a DOTA hapten associated with a radionuclide). A variety of different bi-specific antibody structures are known in the art. In some embodiments, each binding moiety in a bispecific antibody comprises a $V_H$ and/or $V_L$ region from different monoclonal antibodies. In some embodiments, the bispecific antibody comprises an immunoglobulin molecule having $V_H$ and/or $V_L$ regions that contain CDRs from a first monoclonal antibody, and an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and 30 Hollinger et al., *Proc. Natl. Acad. Sci. USA*, 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain Fv (scFv)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

As used herein, the terms "intact antibody" or "intact immunoglobulin" mean an antibody or immunoglobulin that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, an "antigen" refers to a molecule to which an antibody can selectively bind. The target antigen may be a protein (e.g., an antigenic peptide), carbohydrate, nucleic acid, lipid, hapten, or other naturally occurring or synthetic compound. An antigen may also be administered to an animal subject to generate an immune response in the subject.

As used herein, the term "antigen binding fragment" refers to a fragment of a whole immunoglobulin structure which possesses a part of a polypeptide responsible for binding to an antigen. Examples of the antigen binding fragment useful in the present technology include scFv, (scFv)$_2$, scFvFc, Fab, Fab' and F(ab')$_2$, diabodies; linear antibodies; single-chain antibody molecules; and multispecific antibodies formed from antibody fragments.

By "binding affinity" is meant the strength of the total noncovalent interactions between a single binding site of a molecule (e.g., an antibody) and its binding partner (e.g., an antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, a "clearing agent" is an agent that binds to excess bifunctional antibody that is present in the blood compartment of a subject to facilitate rapid clearance via kidneys. The use of the clearing agent prior to administration of a DOTA-based radiotherapeutic facilitates better tumor-to-background ratios in PRIT systems.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" of a composition, is a quantity sufficient to achieve a desired prophylactic or therapeutic effect, e.g., an amount which results in the decrease in the symptoms associated with a disease that is being treated, e.g., the diseases or medical conditions associated with a target polypeptide (e.g., breast cancer, colorectal cancer, brain cancer etc.). The amount of a composition of the present technology administered to the subject will depend on the degree, type and severity of the disease and on the characteristics of the individual, such as general health, age, sex, body weight and tolerance to drugs. The skilled artisan will be able to determine appropriate dosages depending on these and other factors. The compositions of the present technology can also be administered in combination with one or more additional therapeutic compounds.

As used herein, the term "epitope" means an antigenic determinant capable of specific binding to an antibody. Epitopes usually consist of chemically active surface groupings of molecules and usually have specific three dimensional structural characteristics, as well as specific charge characteristics.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" refers to a molecule (e.g., an antibody) which recognizes and binds another molecule (e.g., an antigen), but does not substantially recognize and bind other molecules. The terms "specific binding," "specifically binds to," or is "specific for" a particular molecule (e.g., an antigen, or an epitope on an antigen), as used herein, can be exhibited, for example, by a molecule having a $K_d$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M.

As used herein, the terms "subject," "individual," or "patient" are used interchangeably and refer to an individual organism, a vertebrate, a mammal, or a human. In certain embodiments, the individual, patient or subject is a human.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. By "treating a cancer" is meant that the symptoms associated with the cancer are, e.g., alleviated, reduced, cured, or placed in a state of remission.

It is also to be appreciated that the various modes of treatment of diseases as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Use of Clearing Agents in Pretargeted Radioimmunotherapy (PRIT)

The therapeutic index (TI) of radioimmunotherapy (RIT) should be maximized for effective treatment of solid tumors (Larson S M et al., *Nature Reviews Cancer* 15: 347-60 (2015)). RIT with radiolabeled-IgG antibodies suffers from low TI due to the slow pharmacokinetics of the IgG carrier, and thus are often ineffective at tolerable doses.

An alternative is to use a pretargeting approach to RIT (PRIT). During PRIT, the slow antibody-mediated tumor-targeting step is separated from the administration of the radioactivity. Pre-targeting is a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a carrier that has more favorable pharmacokinetics (e.g., a low-molecular weight compound with rapid renal clearance and low normal tissue uptake and whole-body clearance (Orcutt K D et al., *Molecular imaging and biology* 13: 215-21 (2011) such as a DOTA-hapten), and the dose to normal tissue is minimized while targeting the tumor. To target the radioactivity to tumors, circulating therapeutic agent (e.g., DOTA-hapten) is captured by intra-tumorally localized BsAb or is otherwise efficiently cleared via the renal route.

Clearing agents can rapidly decrease the concentration of circulating biomolecule by forming large complexes in circulation that are recognized by the reticuloendothelial system (RES) or, using the appropriate glycohaptens, target hepatic asialoglycoprotein receptors (ASPGR) (Rossin R et al., *Journal Nuclear Medicine* 54:1989-95 (2013)). The TI of DOTA-PRIT is highly variable based on clearing agent dosing, as circulating BsAb retains the capacity to bind a radiolabeled DOTA hapten. To maximize tumor targeting of the radiolabeled DOTA hapten, a saturating dose of BsAb is generally used so as to ensure the greatest concentration of anti-DOTA-antibody domains for binding subsequently administered radiolabeled DOTA hapten. This step presents the challenge of removing excess circulating unbound BsAb prior to administration of cytotoxic radiolabeled DOTA hapten in order to maximize TI. While long time intervals could be used to allow for endogenous clearance of the BsAb, this may impact the binding capacity of the BsAb for the radiohapten at the tumor, as the BsAb could be degraded and/or internalized, depending on the molecular pharmacology of the BsAb-antigen complex.

A 500kD dextran-DOTA hapten conjugate (Orcutt K D et al., *Molecular Cancer Therapeutics* 11: 1365-72 (2012)) has been previously used for DOTA-based pretargeting of carcinoembryonic antigen. The dextran-CA was designed to bind to the anti-DOTA(M)-scFv domains of circulating BsAb via a DOTA(Y) moiety displayed on the dextran scaffold, and remove the unbound BsAb from the blood via recognition and catabolism by the reticuloendothelial system (RES). On account of its large size, the binding of the dextran-CA to tumor-associated BsAb is restricted due to poor intra-tumoral extravasation Although highly effective, the use of a dextran-CA has drawbacks. As a naturally occurring glucose polymer, the dextran scaffold is inherently polydisperse, thus presenting challenges related to reproducible batch-to-batch manufacture and in vivo use. Also, enzymatic degradation by RES dextran-1,6-glucosidase could lead to the introduction of hapten-fragments thereof into the circulation, which can compete with radiohapten for binding by tumor-BsAb. Similar issues were also seen with albumin-based CA during clinical streptavidin-biotin PRIT (Knox S J et al., *Clinical Cancer Research* 6: 406-14 (2000); Breitz H B et al., *Journal Nuclear Medicine* 41: 131-40 (2000)).

Compositions of the Present Technology

In an aspect, the present technology provides a compound that is

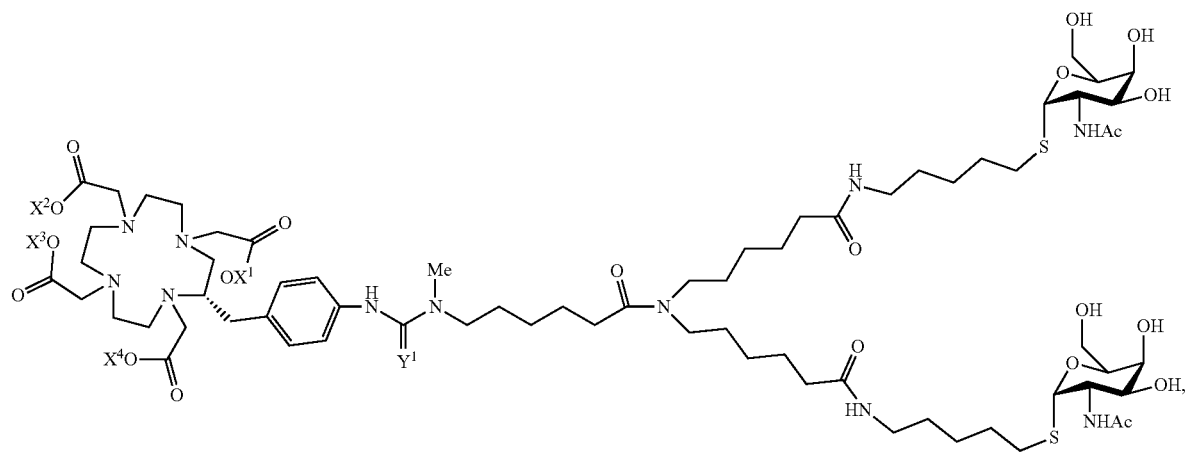

-continued
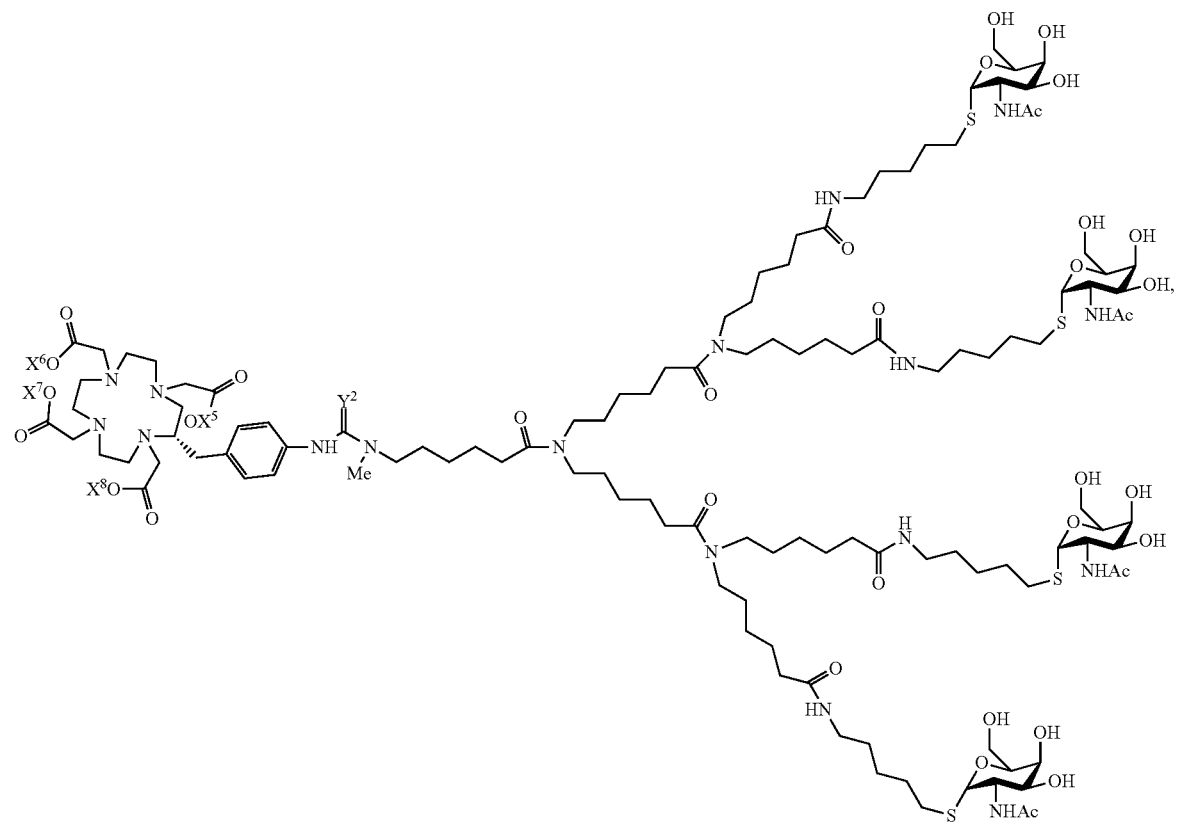

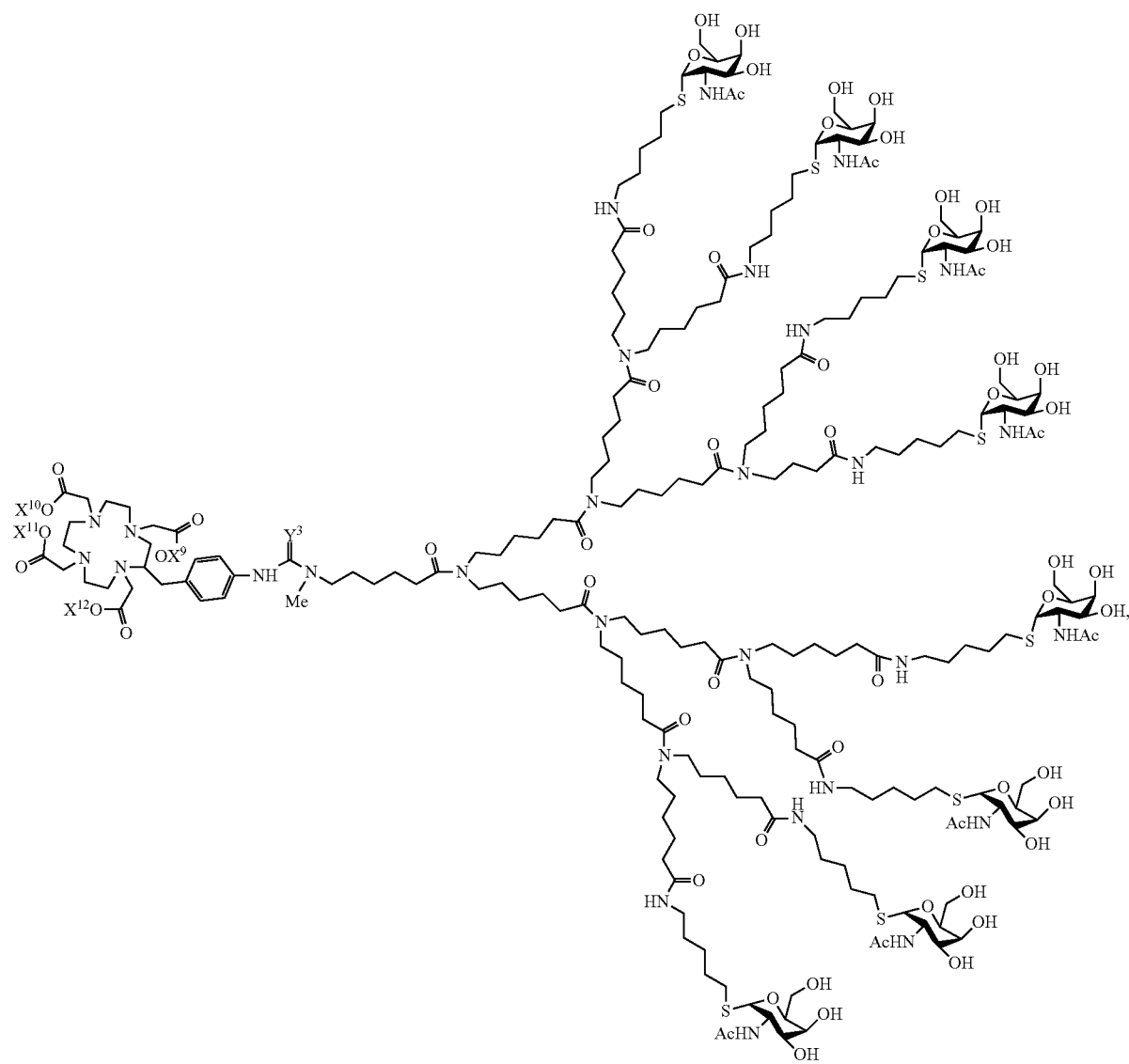

-continued
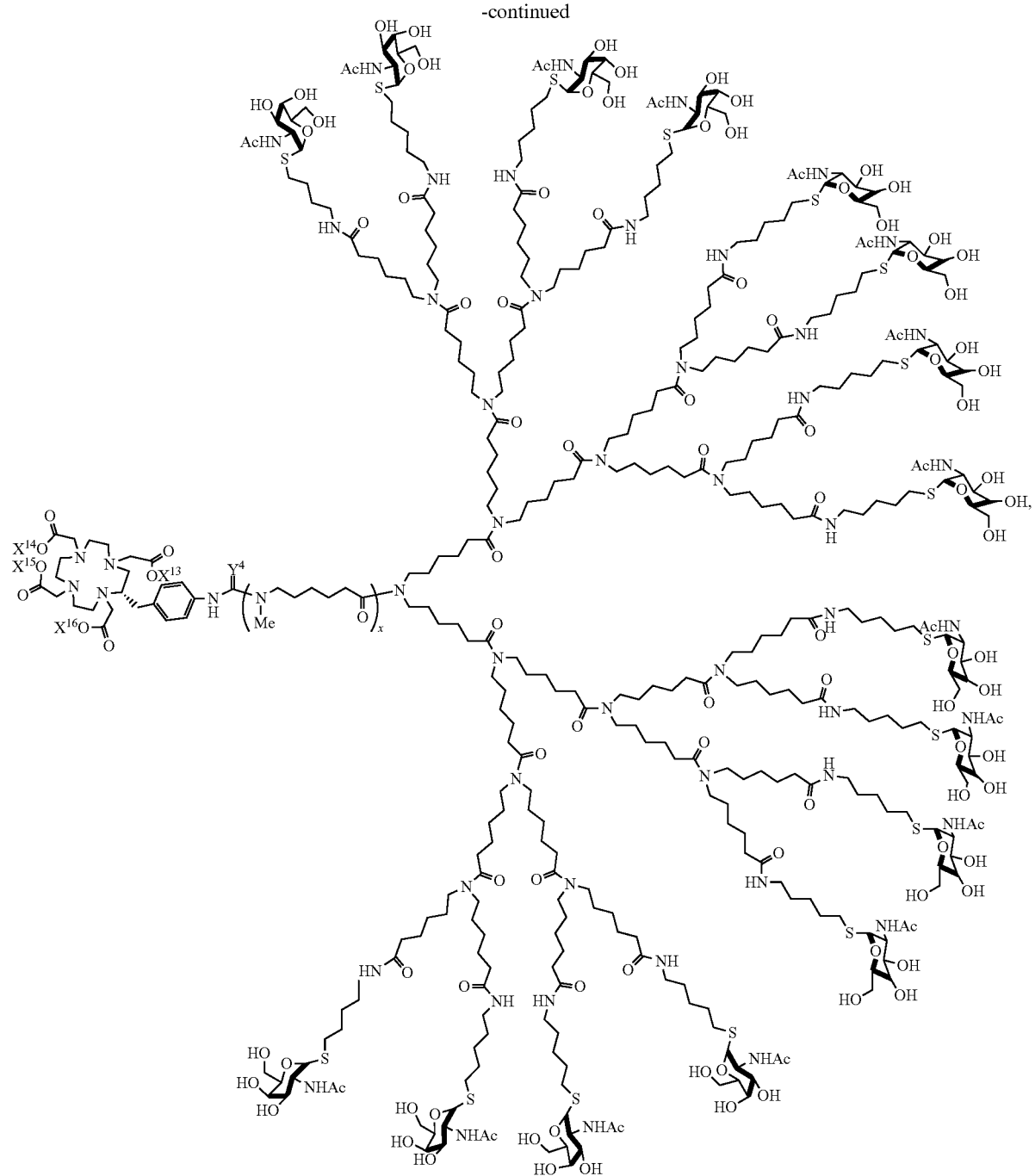

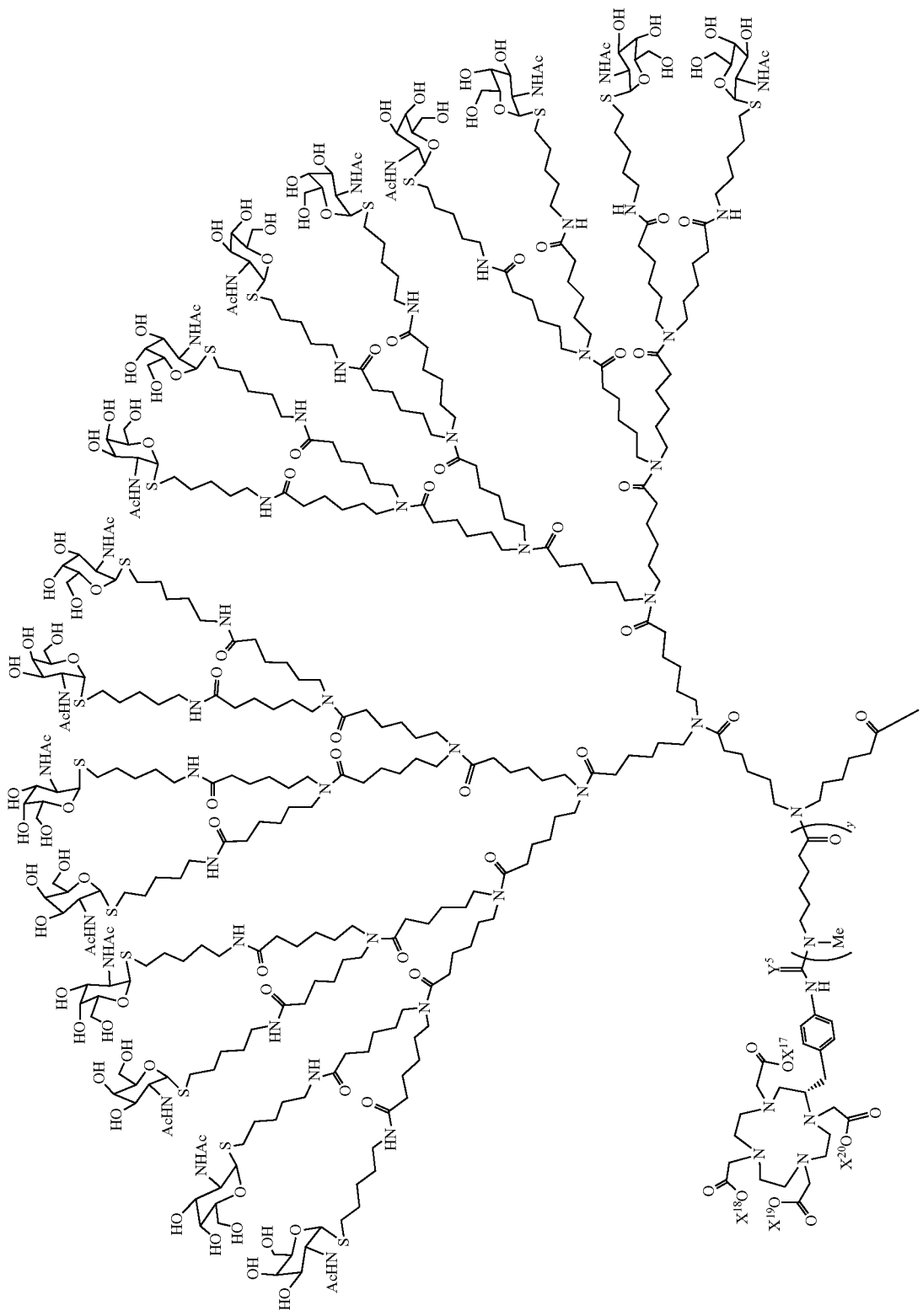

-continued
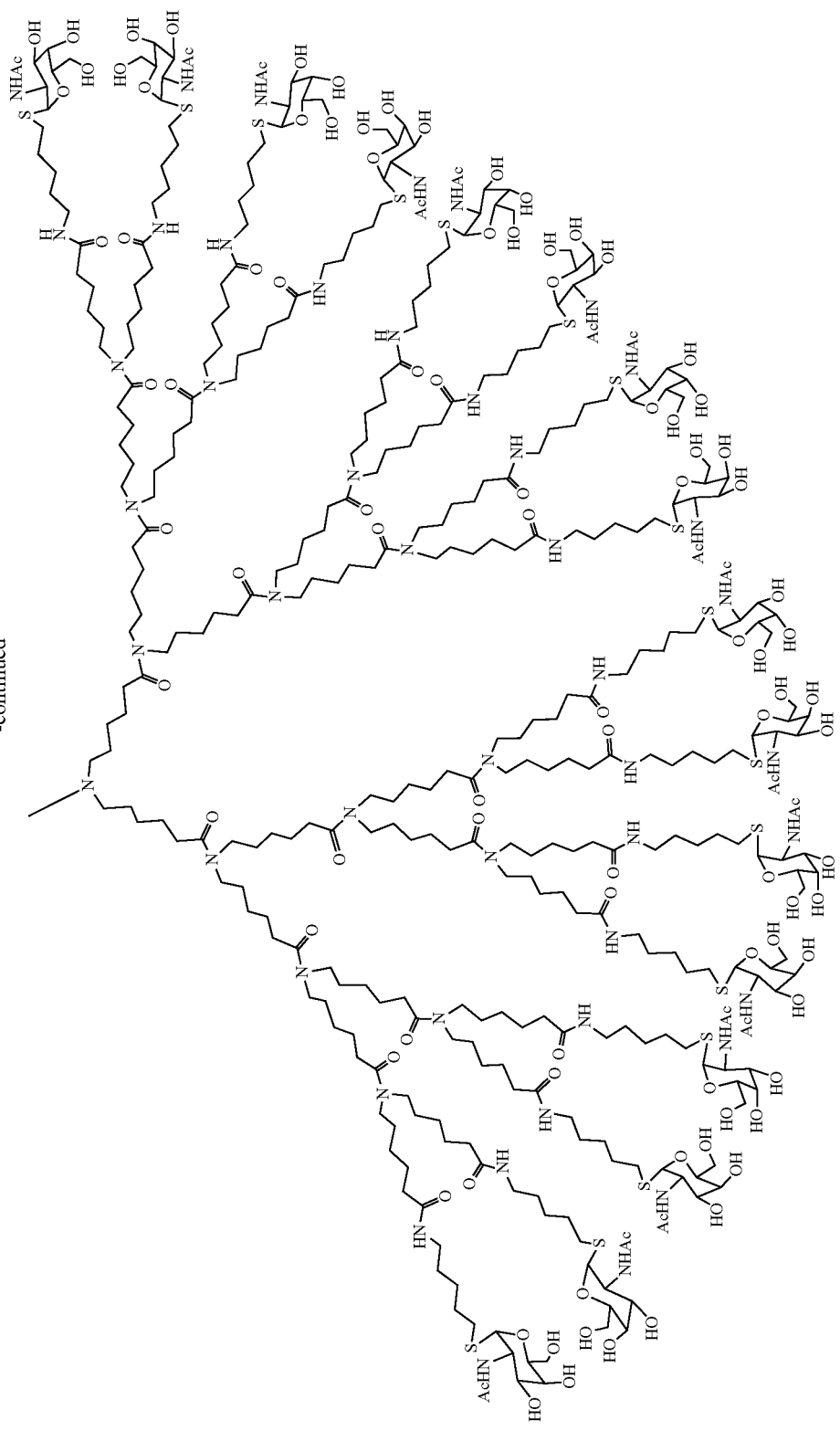

or a pharmaceutically acceptable salt and/or solvate thereof, where $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, and $X^{20}$ are each independently H or a lone pair of electrons (i.e. providing an oxygen anion); $Y^1$, $Y^2$, $Y^3$, $Y^4$, and $Y^5$ are each independently O or S; x is 1, 2, or 3; and y is 1, 2, 3, or 4.

In any embodiment herein, the compound may be a clearing agent (also referred to herein as a "dendron-clearing agent" of the present technology, a "dendron CA" of the present technology, or the like) that is

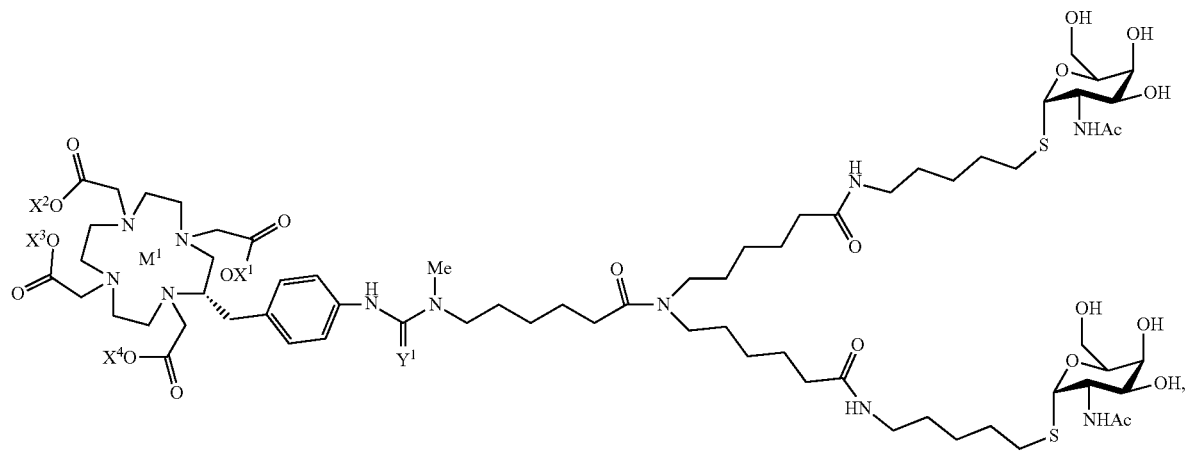

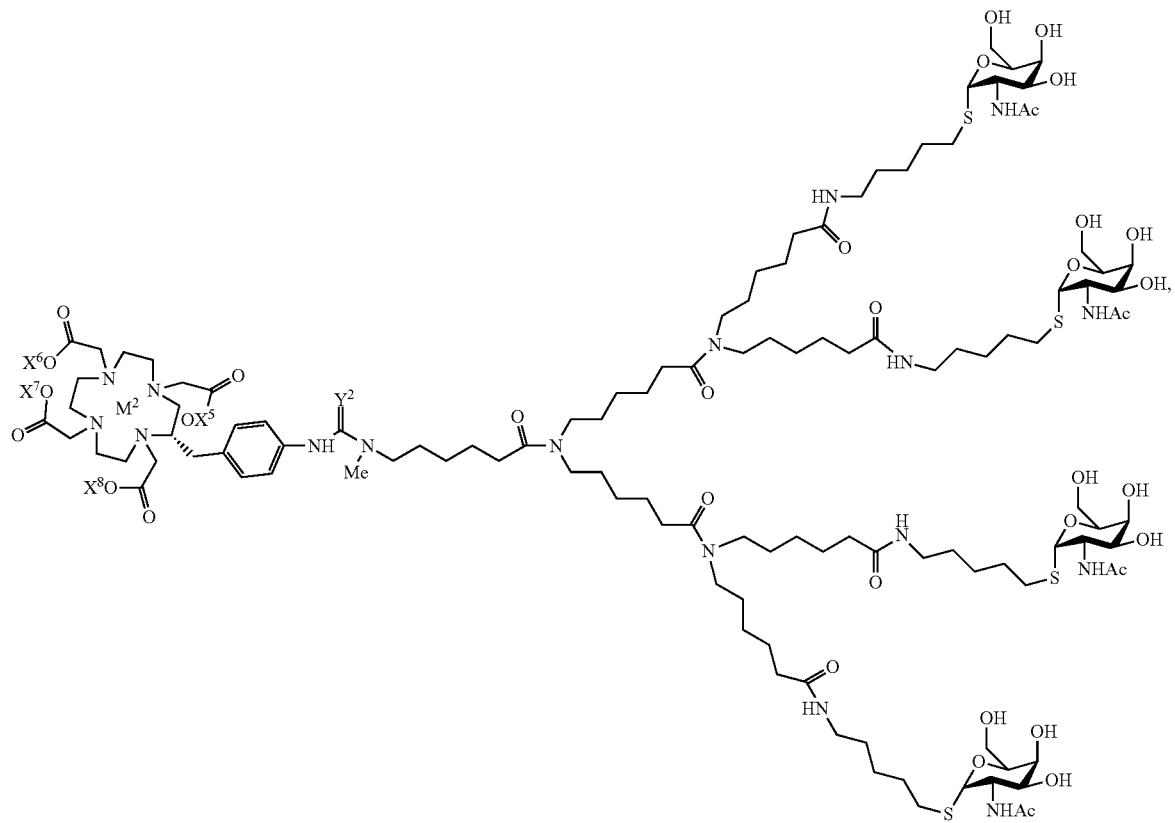

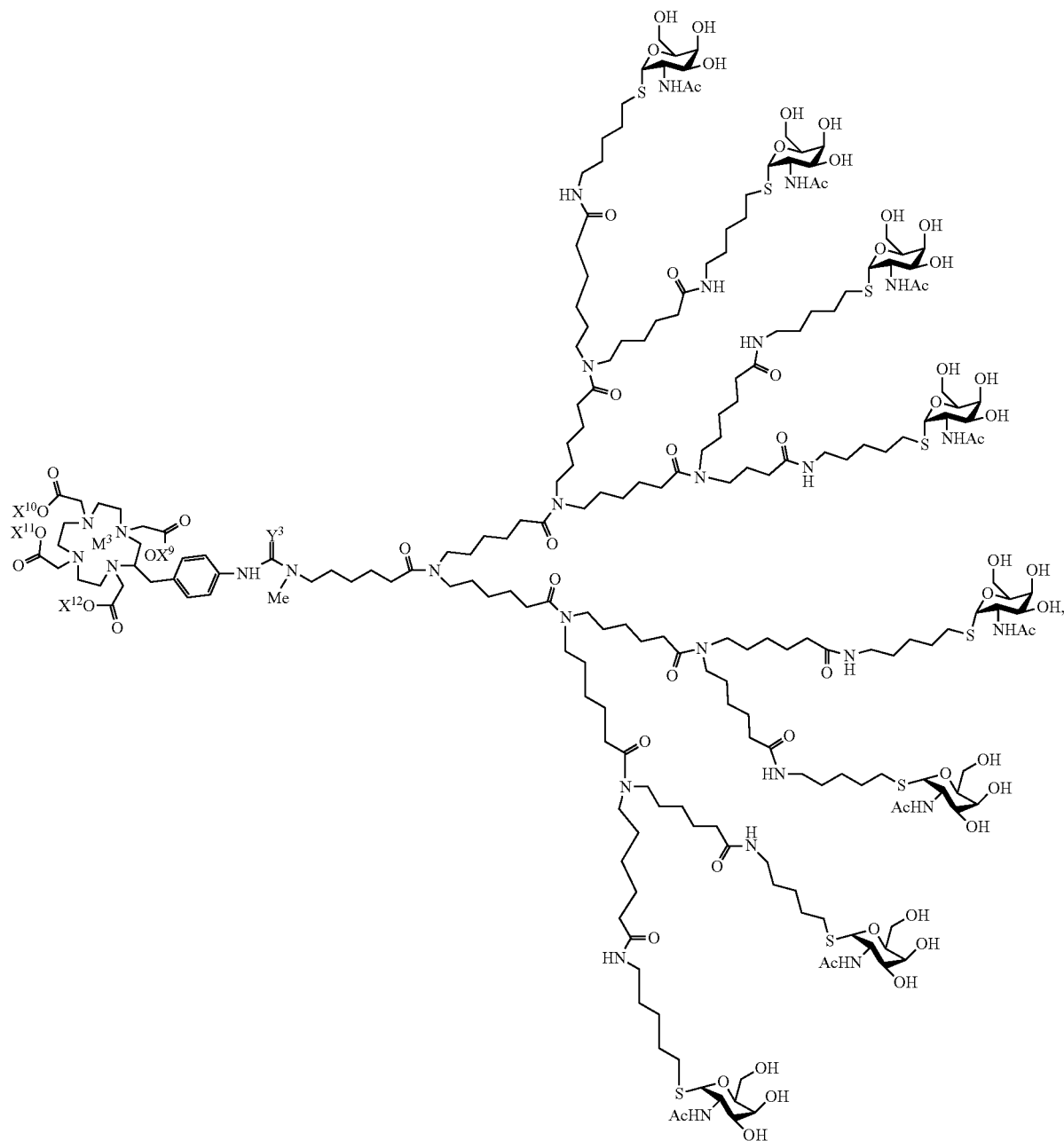

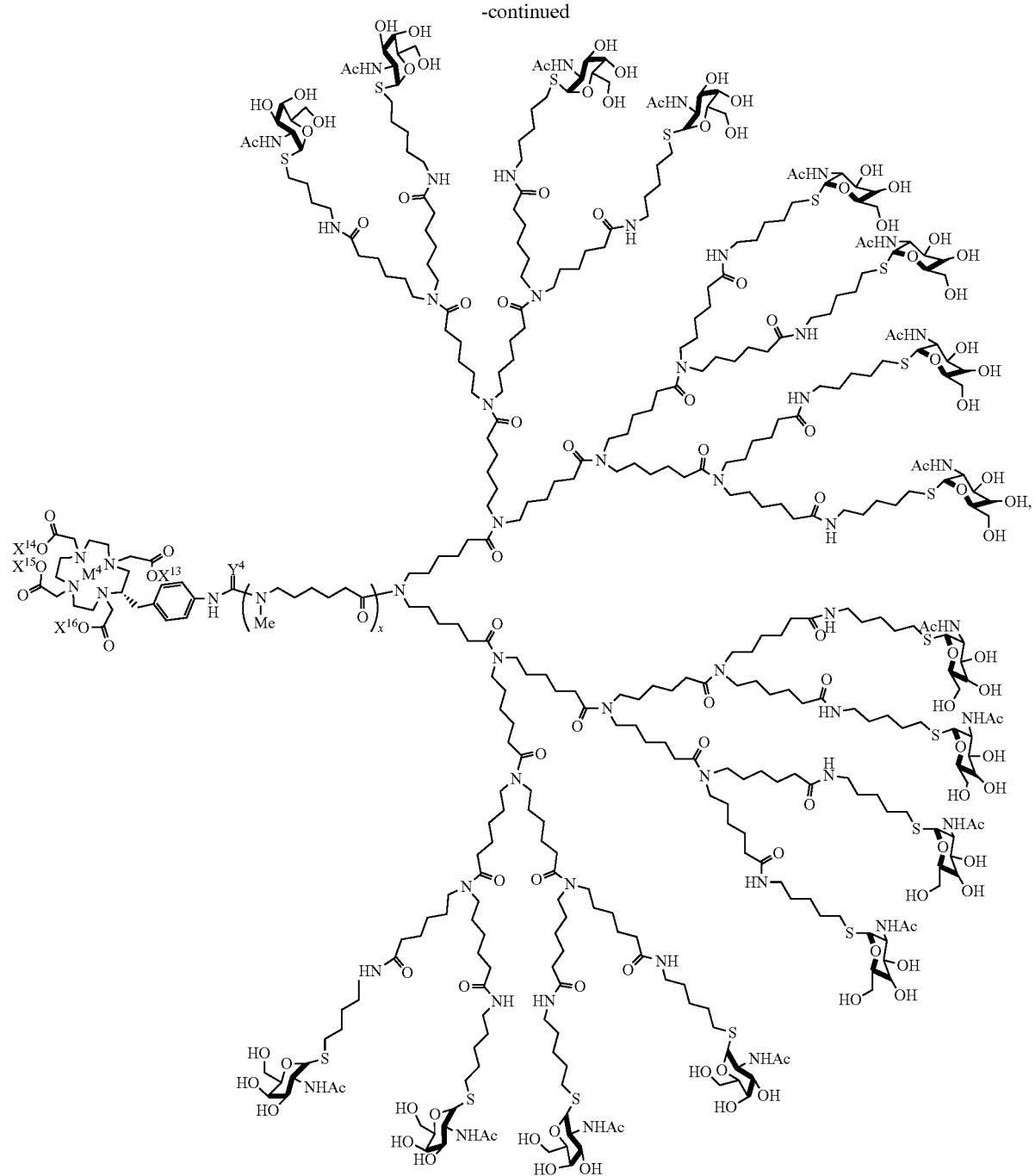

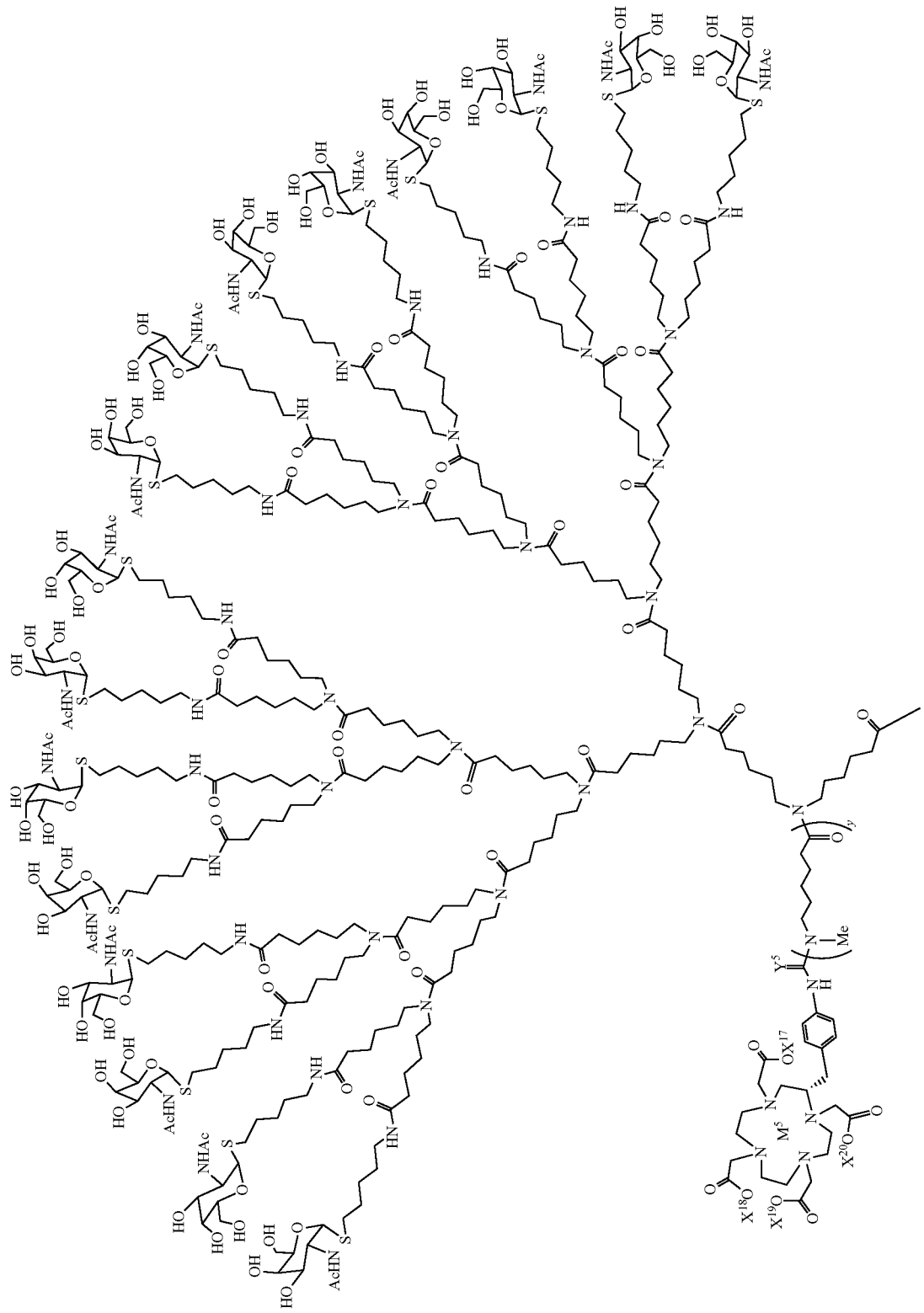

-continued
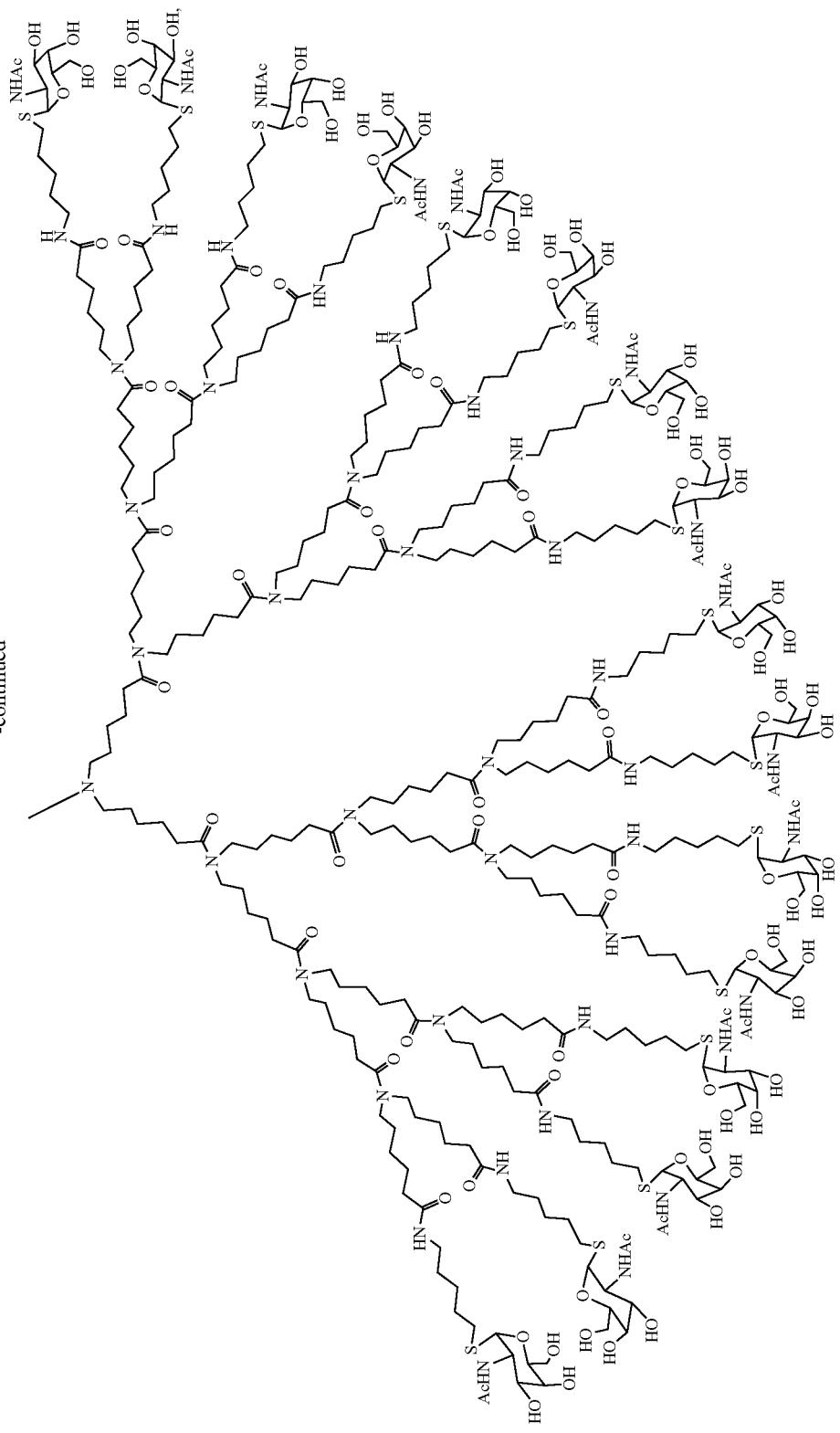

or a pharmaceutically acceptable salt and/or solvate thereof, wherein $M^1$, $M^2$, $M^3$, $M^4$, and $M^5$ are each independently $Lu^{3+}$, $Sc^{3+}$, $Ga^{3+}$, $Y^{3+}$, $In^{3+}$, $La^{3+}$, $Ce^{3+}$, $Eu^{3+}$, $Tb^{3+}$, or $Gd^{3+}$; $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, and $X^{20}$ are each independently H or a lone pair of electrons (i.e. providing an oxygen anion); $Y^1$, $Y^2$, $Y^3$, $Y^4$, and $Y^5$ are each independently O or S; x is 1, 2, or 3; and y is 1, 2, 3, or 4.

In any embodiment herein, it may be that $M^1$, $M^2$, $M^3$, $M^4$, and $M^5$ are each independently not a radionuclide. In any embodiment herein, it may be that $Y^1$, $Y^2$, $Y^3$, $Y^4$ and $Y^5$ are each independently S. In any embodiment herein, it may be that x is 1 or 2. In any embodiment herein, it may be that y is 2 or 3.

In a related aspect, a composition is provided that includes one or more of any embodiment of a compound as described above along with a pharmaceutically acceptable carrier (collectively, such carriers, excipients, fillers, etc., will be referred to as "pharmaceutically acceptable carriers" unless a more specific term is used). The compositions may be used in the methods and imagings described herein. The instant present technology also provides pharmaceutical compositions and medicaments that includes one or more of any embodiment of a compound as described above and a pharmaceutically acceptable carrier. Such pharmaceutical compositions may be packaged in unit dosage form. The pharmaceutical compositions and medicaments may be prepared by mixing one or more compounds of the present technology, pharmaceutically acceptable salts thereof, and/or solvates thereof, with pharmaceutically acceptable carriers, excipients, binders, diluents or the like. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, or rectal administration. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. An isotonic solution will be understood as isotonic with the subject. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Therapeutic Methods of the Present Technology

In one aspect, the present disclosure provides a method for increasing tumor sensitivity to radiation therapy in a subject diagnosed with cancer comprising (a) administering an effective amount of an anti-DOTA bispecific antibody to the subject, wherein the anti-DOTA bispecific antibody is configured to localize to a tumor expressing a tumor antigen target; (b) administering an effective amount of a clearing agent of the present technology to the subject; and (c) administering an effective amount of a radiolabeled DOTA hapten to the subject, wherein the DOTA hapten is configured to form a complex with the anti-DOTA bispecific antibody.

In another aspect, the present disclosure provides a method for treating cancer in a subject in need thereof comprising (a) administering an effective amount of an anti-DOTA bispecific antibody to the subject, wherein the anti-DOTA bispecific antibody is configured to localize to a tumor expressing a tumor antigen target; (b) administering an effective amount of a clearing agent of the present technology to the subject; and (c) administering an effective amount of a radiolabeled DOTA hapten to the subject, wherein the DOTA hapten is configured to form a complex with the anti-DOTA bispecific antibody. The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, *vinca* alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

Additionally or alternatively, in some embodiments of the methods disclosed herein, the radioactive levels emitted by the radiolabeled DOTA hapten-anti-DOTA bispecific antibody complex are detected between 4 to 24 hours after the radiolabeled DOTA hapten is administered. The radioactive levels emitted by the complex may be expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1. Additionally or alternatively, in some embodiments of the methods disclosed herein, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Additionally or alternatively, in some embodiments of the methods disclosed herein, the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM.

Additionally or alternatively, in some embodiments of the methods disclosed herein, the anti-DOTA bispecific antibody, the clearing agent, and/or the radiolabeled DOTA hapten is administered intravenously, intramuscularly, intraarterially, intrathecally, intracapsularly, intraorbitally, intradermally, intraperitoneally, transtracheally, subcutaneously, intracerebroventricularly, orally or intranasally.

Additionally or alternatively, in some embodiments of the methods disclosed herein, the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer. The brain cancer may be a pituitary adenoma, a meningioma, a neuroblastoma, or a craniopharyngioma.

Additionally or alternatively, in some embodiments of the methods disclosed herein, the radiolabeled DOTA hapten comprises one or more of Proteus-DOTA, S-2-(R-aminobenzyl)-1,4,7,10-tetraazacyclododecane tetra-acetic acid (DOTA-Bn), DOTA-Bn-biotin, BAD (((S)-2-(4-(2-bromo)-acetamido)-benzyl)-DOTA), NBD ((S)-2-(4-nitrobenzyl)-DOTA), DOTA-RGD, DOTA-PEG-E(c(RGDyK))$_2$, DOTA-8-AOC-BBN, p-N02-Bn-DOTA, DOTA-PESIN, DOTA-biotin-sarcosine (DOTA-biotin), 1,4,7,10-tetraazacyclododecane-1,4,7,10-tetraacetic acid mono (N-hydroxysuccinimide ester) (DOTA-NHS), or DOTATyr-LysDOTA. Alternatively, any radiolabeled DOTA hapten known in the art may be employed in the methods disclosed herein. The radiolabeled DOTA hapten may be labelled with a radionuclide selected from the group consisting of $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{22}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$n, $^{67}$Ga $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, and $^{64}$Cu.

In any of the above embodiments of the methods disclosed herein, the subject is human. The anti-DOTA bispecific antibody is administered under conditions and for a period of time (e.g., according to a dosing regimen) sufficient for it to saturate tumor cells and any unbound anti-DOTA bispecific antibody is removed from the blood stream after administration of the anti-DOTA bispecific antibody. In some embodiments, the radiolabeled DOTA hapten is administered after a time period that may be sufficient to permit clearance of unbound anti-DOTA bispecific antibody.

Additionally or alternatively, in some embodiments of the methods disclosed herein, the clearing agent and the radiolabeled DOTA hapten are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody (optionally so that relevant tumor cells are saturated); (ii) administration of a clearing agent of the present technology and a radiolabeled DOTA hapten and; (iii) optional additional administration of the radiolabeled DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

The radiolabeled DOTA hapten may be administered at any time between 1 minute to 4 or more days following administration of the anti-DOTA bispecific antibody. For example, in some embodiments, the radiolabeled DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled DOTA hapten may be administered at any time after 4 or more days following administration of the anti-DOTA bispecific antibody.

Additionally or alternatively, in some embodiments of the methods disclosed herein, the radiolabeled DOTA hapten may be administered at any time between 1 minute to 4 or more days following administration of the clearing agent. For example, in some embodiments, the radiolabeled DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the clearing agent. Alternatively, the radiolabeled DOTA hapten may be administered at any time after 4 or more days following administration of the clearing agent.

Kits

The present technology provides kits containing components suitable for treating cancer in a patient. In one aspect, the kits comprise a clearing agent of the present technology, and instructions for use. The kits may further comprise at least one anti-DOTA BsAb. In some embodiments, the at least one anti-DOTA BsAb binds to a tumor antigen target selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), 0-catenin, EBNA (Epstein-Barr Virus nuclear antigen) 1-6, p53, lung resistance protein (LRP) Bcl-2, prostate specific antigen (PSA), and Ki-67. Additionally or alternatively, in some embodiments, the at least one anti-DOTA BsAb binds to a tumor antigen target selected from the group consisting of CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, and EpCAM. The at least one anti-DOTA BsAb may be provided in the form of a prefilled syringe or autoinjection pen containing a sterile, liquid formulation or lyophilized preparation of the antibody (e.g., Kivitz et al., *Clin. Ther.* 28:1619-29 (2006)).

Additionally or alternatively, in some embodiments, the kits further comprise a DOTA hapten that is optionally labeled with one or more radionuclides. Examples of DOTA haptens include but are not limited to Proteus-DOTA, S-2-(R-aminobenzyl)-1,4,7,10-tetraazacyclododecane tetra-acetic acid (DOTA-Bn), DOTA-Bn-biotin, BAD (((S)-2-(4-(2-bromo)-acetamido)-benzyl)-DOTA), NBD ((S)-2-(4-nitrobenzyl)-DOTA), DOTA-RGD, DOTA-PEG-E(c (RGDyK))$_2$, DOTA-8-AOC-BBN, p-N02-Bn-DOTA, DOTA-PESIN, DOTA-biotin-sarcosine (DOTA-biotin), 1,4,7,10-tetraazacyclododecane-1,4,7,10-tetraacetic acid mono (N-hydroxysuccinimide ester) (DOTA-NHS), DOTATyr-LysDOTA and the like. Additionally or alternatively, in some embodiments of the kits of the present technology, the one or more radionuclides are selected from among $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Additionally or alternatively, in certain embodiments, the one or more radionuclides are selected from the group consisting of $^{86}$Y, $^{90}$Y, $^{89}$S, $^{165}$Dy, $^{186}$Re, $^{188}$Re, $^{177}$Lu, $^{67}$Cu, $^{111}$In, $^{67}$Ga $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga $^{227}$Th, and $^{64}$Cu.

If the kit components are not formulated for oral administration, a device capable of delivering the kit components through some other route may be included. Examples of such devices include syringes (for parenteral administration) or inhalation devices.

The kit components may be packaged together or separated into two or more containers. In some embodiments, the containers may be vials that contain sterile, lyophilized formulations of a clearing agent disclosed herein, a DOTA hapten and/or an anti-DOTA BsAb composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers.

EXAMPLES

Example 1: Exemplary Synthesis of Compounds of Present Technology

General. DOTA-Bn-isothiocyanate (p-SCN-Bn-DOTA) was purchased from Macrocyclics, Inc. (Plano, Tex.) and Amine-PEG4-DOTA was purchased from CheMatech (Dijon, France). Optima™ grade hydrochloric acid was purchased from Thermo Fisher Scientific (Waltham, Mass.). Chelex-100 resin, 200-400 mesh was purchased from Bio-Rad Laboratories (Hercules, Calif.). PD-10 gel-filtration size-exclusion columns (containing 8.3 mL of Sephadex™ G-25 resin/column) were purchased from GE Healthcare Life Sciences (Pittsburgh, Pa.). All other reagents and synthesis-grade chemicals were purchased from Sigma-Aldrich (St. Louis, Mo.) and used without further purification. All solvents used for HPLC analysis (HPLC grade) and compound purification were also purchased from Thermo Fisher Scientific (Waltham, Mass.). All buffers and solutions were prepared using ultrapure water (18 MΩ-cm resistivity).

All liquid chromatography mass spectrometry (LC/MS) data was obtained using a Waters Autopure system (Milford, Mass.) comprising the following instrumentation: 2767 Sample Manager, 2545 Binary Gradient Module, System Fluidics Organizer, 2424 Evaporative Light Scattering Detector, 2998 Photodiode Array Detector, 3100 Mass Detector. HPLC solvents (solvent A, 0.05% TFA in water; solvent B, 0.05% TFA in acetonitrile) were filtered prior to use. The analytical method was 5-25% solvent B in 10 min, 1.2 mL/min flow rate. Analytical columns: Waters XBridge BEH300 (Milford, Mass.), C4, 3.5 µm, 4.6×50 mm and C18, 4 µm, 4.6×50 mm. Preparative method: 5-25% solvent B in 30 min, 20 mL/min flow rate. Preparative column: Waters XBridge Prep (Milford, Mass.) C18, 4 µm, Optimum Bed Density, 19×150 mm.

All NMR data were obtained with either a Bruker AV500 or AV600 instruments (Bruker, Billerica, Mass.) at ambient temperature. The following abbreviations were used: singlet (s), broad singlet (bs), doublet (d), triplet (t), quartet (q), pentet (p), doublet of a doublet (dd), multiplet (m).

All experiments involving molecules with high metal complexing capacity such as DOTA were conducted in glassware that was pre-washed with metal-free HCl, rinsed with high purity water (e.g., glass-distilled water), and oven dried. Chromatography was carried out on manually packed glass columns to avoid loading the complexing agent with metal leached or extracted from metal column walls. The reverse phase purifications were carried out on clean, metal-free glass columns which were packed manually with loose C-18 silica gel. The water content in the final complexes was not measured.

CCA-16-methyl ester-NHBoc (illustrated below) and 5-((tert-butoxycarbonyl)amino)pentyl-2-acetamido-2-deoxy-1-thio-3,4,6-tri-O-acetyl-α-D-galactopyranoside ("Mono-peracetyl-sugar-NHBoc") were prepared according to similar methods and protocols as described in Yoo, B. et al. "N-Acetylgalactosamino Dendrons as Clearing Agents to Enhance Liver Targeting of Model Antibody-Fusion Protein," Bioconjugate Chem. 2013, 24, 2088-2103 (and accompanying Supporting Information) and in Cheal, S. M. et al. "Evaluation of Glycodendron and Synthetically Modified Dextran Clearing Agents for Multistep Targeting of Radioisotopes for Molecular Imaging and Radioimmunotherapy," Mol. Pharmaceutics 2014, 11, 400-16 (and accompanying Supporting Information), each of which is herein incorporated by reference. Relevant characterization data for CCA-16-methyl ester-NHBoc and Mono-peracetyl-sugar-NHBoc is provided below.

CCA-16-methyl ester-NHBoc:

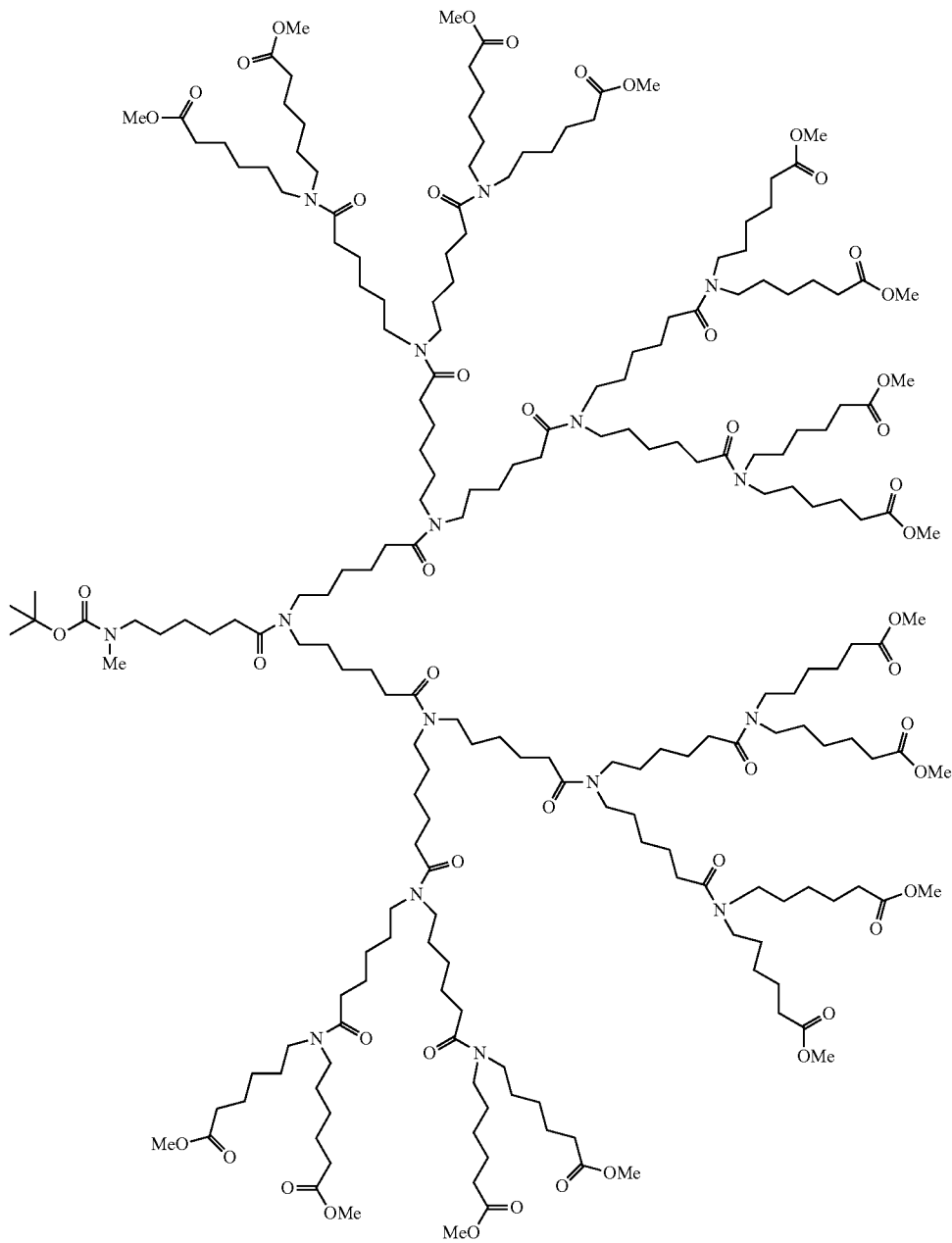

¹H NMR (600 MHz, D₂O) δ: 3.68, 3.66 (2s, 48H, OCH₃), 3.30-3.26 (m, 32H), 3.22-3.19 (m, 32H), 2.83 (bs, NCH₃), 2.35-2.25 (m, 64H), 1.69-1.51 (m, 128H), 1.44 (s, 9H, C(CH₃)₃), 1.34-1.29 (m, 64H). ¹³C NMR (125 MHz, D₂O) δ: 174.10, 173.87, 172.10, 51.57, 51.48, 47.86, 47.79, 45.78, 45.70, 33.95, 33.84, 33.83, 33.05, 32.89, 29.21, 28.90, 28.50, 27.70, 27.48, 27.46, 26.99, 26.84, 26.55, 26.42, 25.23, 25.13, 24.68, 24.64.
Mono-peracetyl-sugar-NHBoc (5-((tert-butoxycarbonyl)amino)pentyl-2-acetamido-2-deoxy-1-thio-3,4,6-tri-O-acetyl-α-D-galactopyranoside): ¹H NMR (600 MHz, D₂O) δ: 5.57 (d, 1H, J=7.4 Hz), 5.49 (d, 1H, J=4.4 Hz), 5.38 (d, 1H, J=2.4 Hz), 5.05 (dd, 1H, J=2.4 Hz, J=7.4 Hz), 4.80-4.74 (m, 1H), 4.58 (bs, 1H), 4.54 (t, 1H, J=5.4 Hz), 4.13 (dd, 1H, J=9.6 Hz, J=5.4 Hz), 4.09 (dd, 1H, J=9.6 Hz, J=5.4 Hz), 3.14-3.08 (m, 2H), 2.66-2.55 (m, 2H), 2.16, 2.05, 2.01, 1.98 (4s, 12H, COCH₃), 1.67-1.61 (m, 2H), 1.44 (s, 9H, C(CH₃)₃), 1.41-1.38 (m, 2H). ¹³C NMR (125 MHz, D₂O) δ: 171.00, 170.39, 170.28, 170.15, 155.98, 84.93, 68.54, 67.34, 67.24, 61.83, 48.33, 40.38, 30.97, 29.62, 29.28, 28.43, 25.94, 23.34, 20.75, 20.71.
Exemplary Synthesis
CCA-16-Acid:
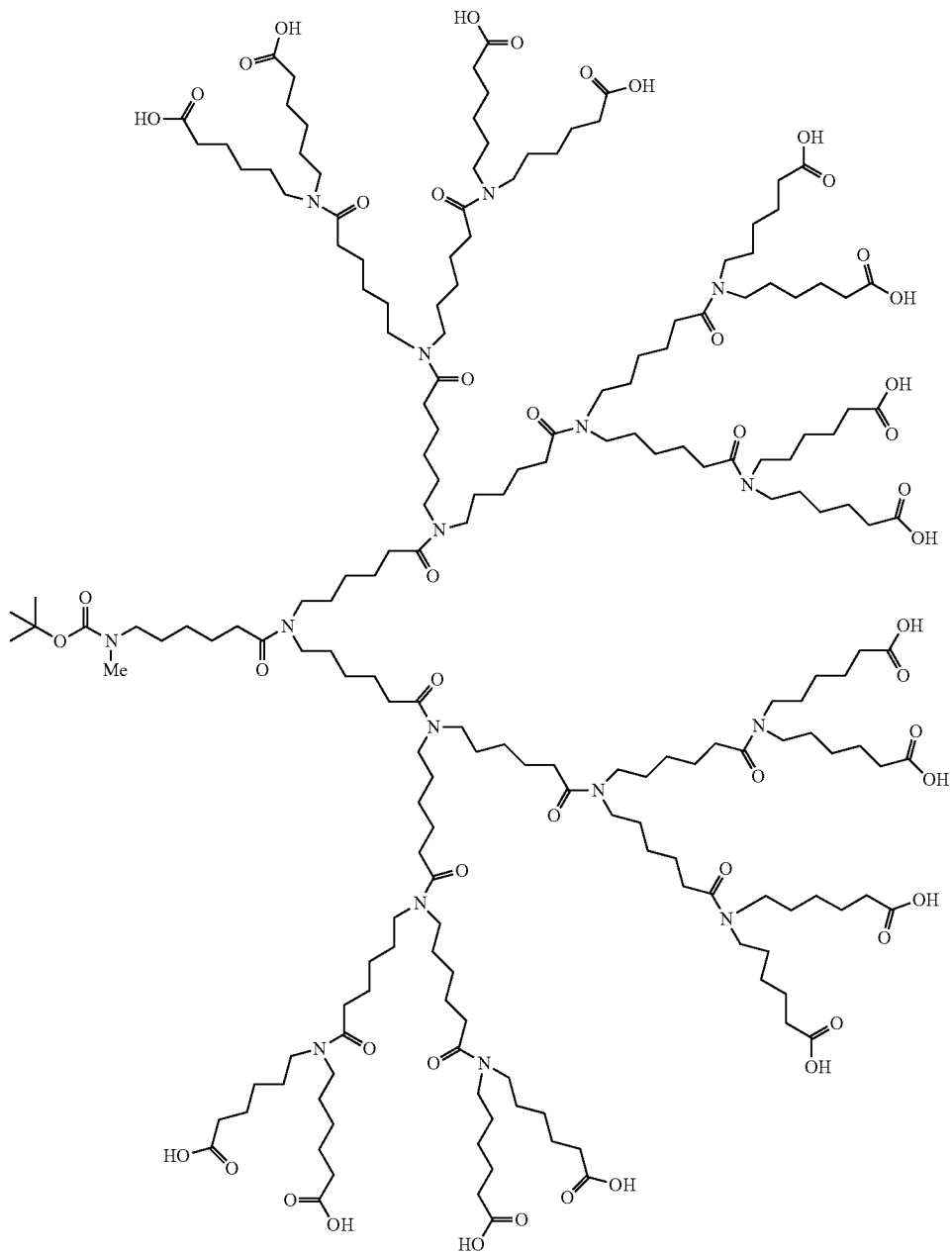

CCA-16-methyl ester-NHBoc (2.1 g, 0.54 mmol) in MeOH (60 mL) was added NaOH (10 N, 16 mL) and water (16 mL). The resulting mixture was stirred at RT for 1 h. PH was then adjusted to 5.0 with 2.0 N HCl and solution was loaded into a separatory funnel. Extraction with DCM/t-Butanol (3/1, v/v), 150 mL×5, and the combined organic layers were briefly dried over $Na_2SO_4$. After filtration over a bed of celite, the filtrate was evaporated under reduced pressure, and the residue was further dried over high vacuum for 2 h to provide 2.0 g of a colorless thick oil. The product was of sufficient purity to be directly submitted to the next step.

CCA-16-Sugar-NHBoc.

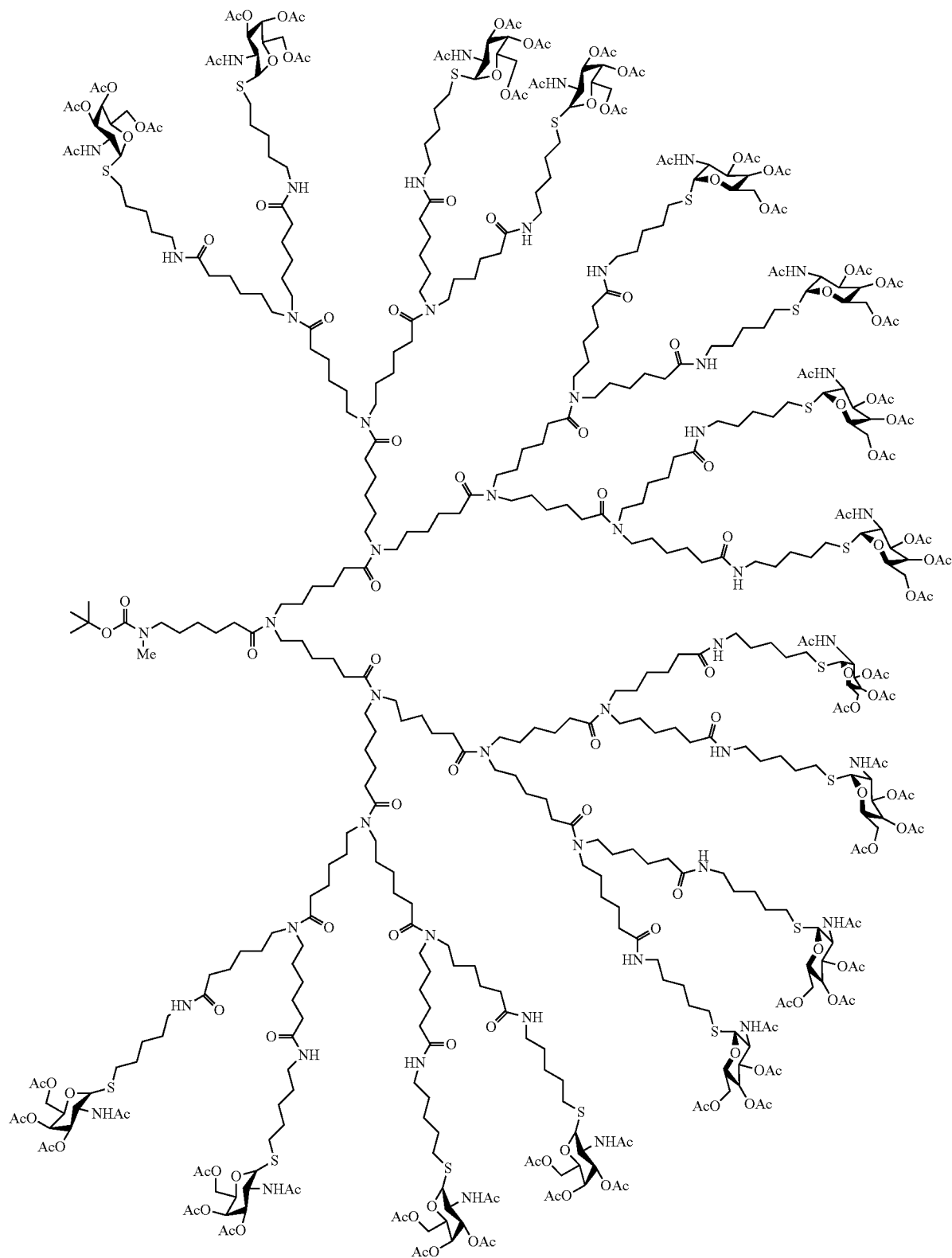

CCA-16-acid (2.0 g, 0.54 mmol) was diluted in DMF (80 mL) before treatment with HATU (4.0 g, 10.5 mmol) and 5-amino-1-pentyl-α-thio tetraacetylgalactosamine (5.6 g, 9.9 mmol). The resulting mixture was stirred at RT for 20 min, before DIPEA (8.0 mL) was added. After 1 h, DCM (200 mL) was added, and the reaction mixture was washed with water (2×100 mL). The organic layer was then briefly dried over Na$_2$SO$_4$, filtered over a bed of celite, and the filtrate was concentrated under vacuum. Purification by flash column chromatography using the gradient 0% to 15% MeOH in DCM (v/v) afforded CCA-16-sugar-NHBoc, 4.9 g, 85% yield. $^1$H NMR (600 MHz, D$_2$O) δ: 7.95 (bs, 12H, NH), 5.64-5.61 (m, 16H), 5.47-5.46 (d, 16H, J=2.8 Hz), 5.06 (dd, 16H, J=11.8 Hz), 4.64-4.60 (m, 32H), 4.18-4.12 (m, 32H), 3.35 (m, 32H), 3.21-3.19 (m, 36H), 3.02, 2.88 (2s, 3H, NCH$_3$), 2.86-2.84 (bs, 4H), 2.70-2.61 (m, 32H), 2.41-2.38 (m, 36H), 2.24 (m, 32H), 2.21, 2.06, 1.98, 1.97 (4s, 192H, COCH$_3$), 1.69-1.64 (m, 128H, 1.59-1.53 (m, 70H), 1.48 (s, 9H, OC(CH$_3$), 1.48-1.46 (m, 32), 1.40-1.33 (m, 70H). $^{13}$C NMR (125 MHz, D$_2$O) δ: 174.60, 174.38, 174.30, 173.41, 172.23, 172.14, 170.66, 170.34, 84.07, 68.23, 67.23, 66.80, 61.78, 53.46, 45.67, 39.01, 38.88, 35.73, 35.63, 35.58, 32.59, 32.51, 30.03, 29.06, 28.66, 28.54, 27.57, 27.08, 26.37, 26.28, 26.22, 26.10, 25.83, 25.45, 25.36, 25.18, 25.10, 21.26, 21.22, 19.44, 19.37, 19.24.

CCA-16-peracetyl-α-thiogalactosamine-NH$_2$.TFA:

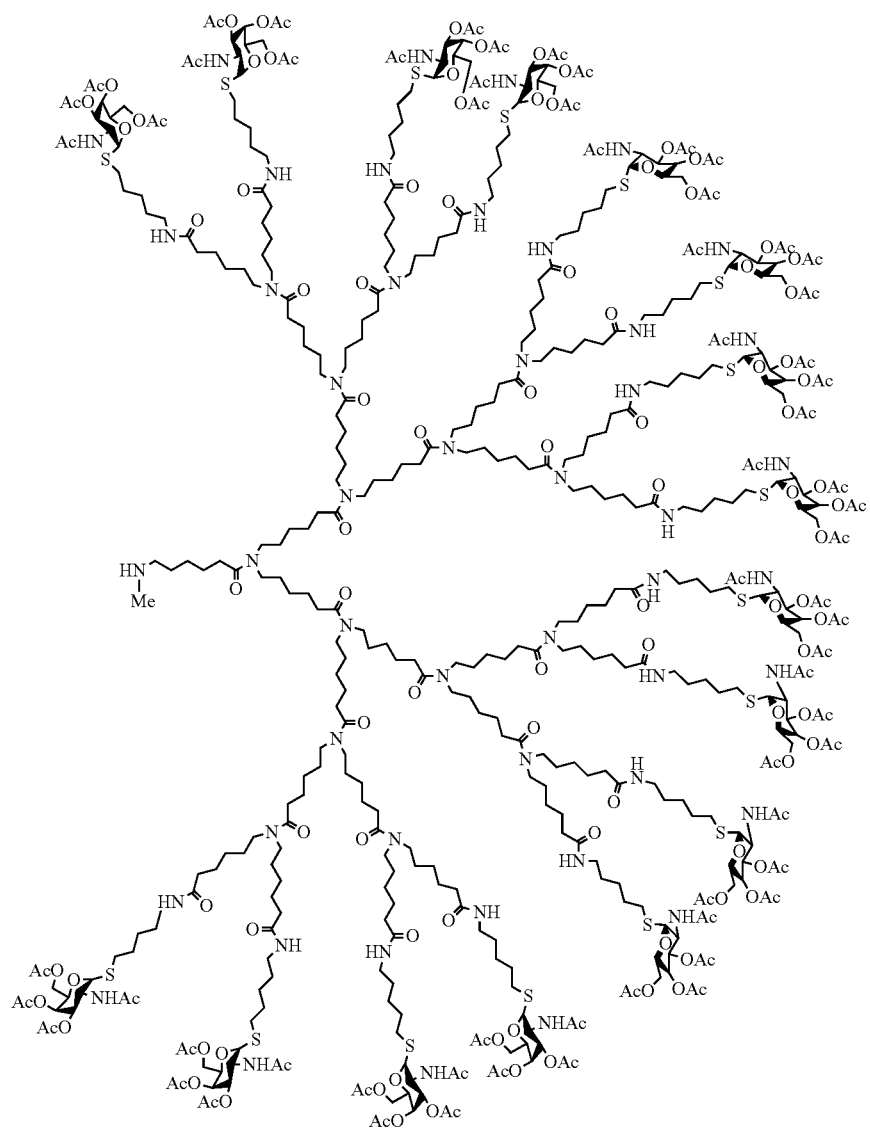

20 mg CCA-16-peracetyl-α-thiogalactosamine-NHBoc (1.9 µmol) in 0.8 mL 20% TFA in dichloromethane (v/v) was stirred at RT for 60 min, then the mixture was evaporated under reduced pressure to remove TFA and DCM. Reaction evolution was monitored by LCMS, was run on an Autopure System (Waters) using C4 (Xbridge, Waters, 4.6×50 mm) using the gradient 5-95% (v/v) acetonitrile in water containing 0.05% TFA over 10 min. Detection was insured by concomitant Mass Spec, Diode Array, and Evaporative Light Scattering detections. The residue (20 mg) was further dried overnight under high vacuum and was used directly in the next step.

CCA-16-peracetyl-α-thiogalactosamine-NHCSNMe-Bn-DOTA:

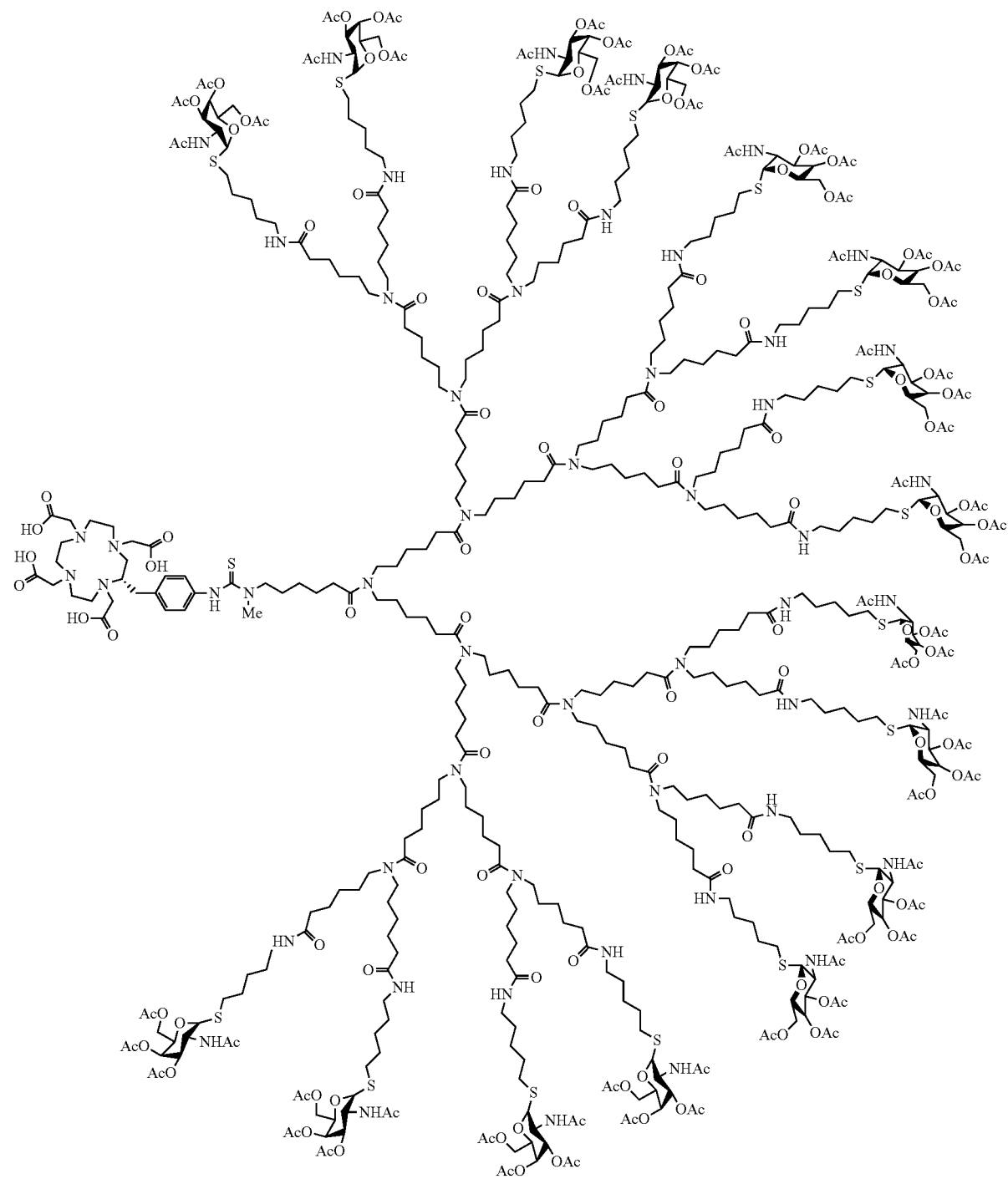

The crude ammonium salt (CCA-16-peracetyl-α-thiogalactosamine-NH₂.TFA) and P-SCN-Bn-DOTA (2.5 mg, 3.8 pmol, 2 eq) was dissolved in DMF (0.3 mL) and Et₃N (6 μmL) was added. The resulting homogeneous mixture was stirred at RT for 4 h, and the volatiles were removed under high vacuum at room temperature to give a foam of sufficient purity for use in the next step. LCMS assessment was run on the same system as described in the previous step but instead using an XBridge C18 column (4.6×150 mm) and using the gradient 40-95% (v/v) acetonitrile in water containing 0.05% TFA.

CCA-16-α-thio-peracetyl galactosamine-DOTA-Y³⁺:

The crude material from the previous step; CCA-16-peracetyl-α-thiogalactosamine-NHICSNMe-Bn-DOTA was added to a solution of YCl₃.6H₂O (6 mg) in 0.05 M HCl (0.2 mL) and 0.5 M NH₄OAc (0.2 mL). The mixture was shaken for 4 h. Attempts to purify by TIPLC at this stage were not successful. However, analytical monitoring showed the reaction to be complete with reasonable purity. LCMS was run on an XBridge C18 column using the gradient system 5-95% (v/v) acetonitrile in water (both containing 0.05% TFA) over 10 min. The residue was submitted into the next and final step. ESI-MS (m/z): [M+6H]⁶⁺ calc. 1,847.55, obs. 1,847.86

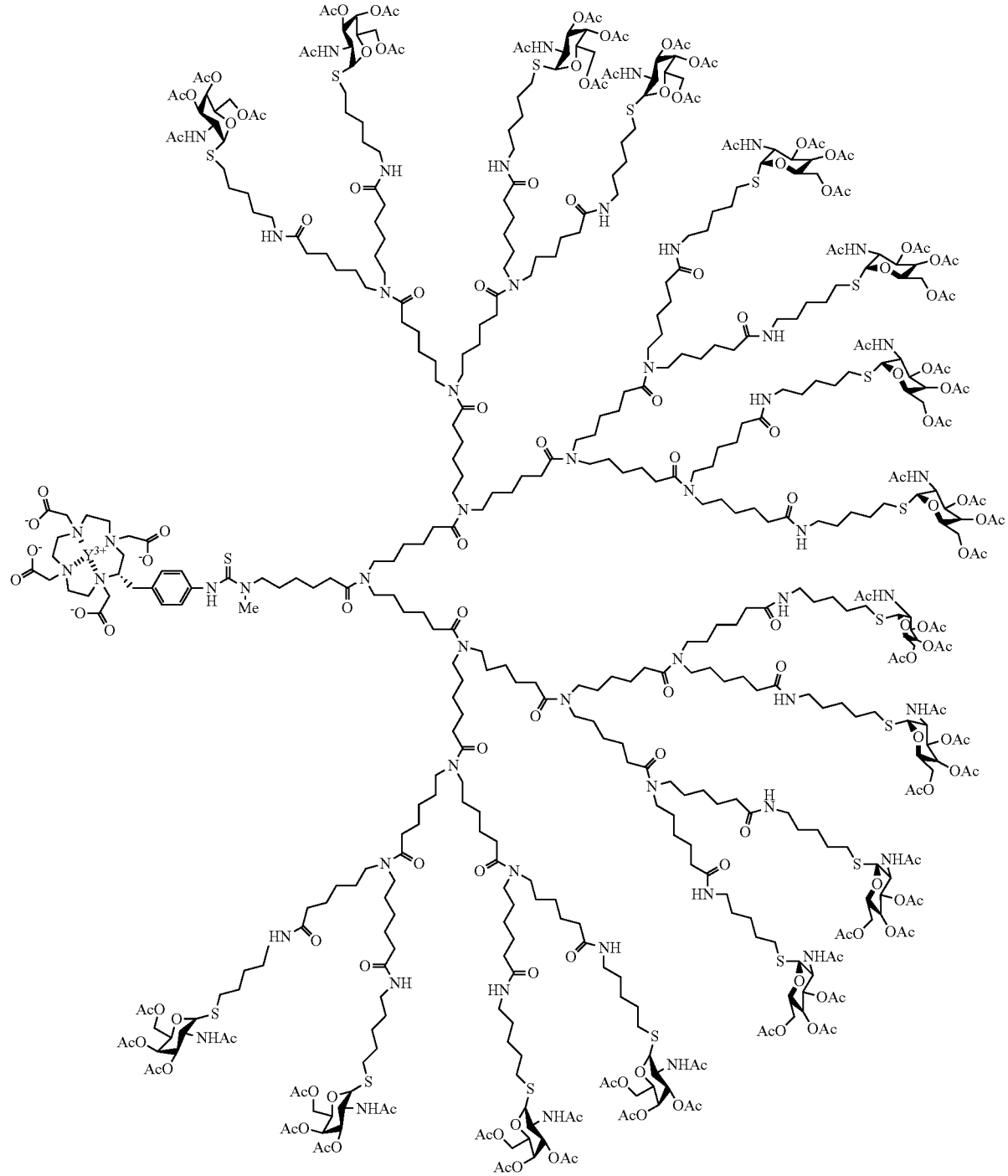

CCA-16-DOTA-Y³⁺:

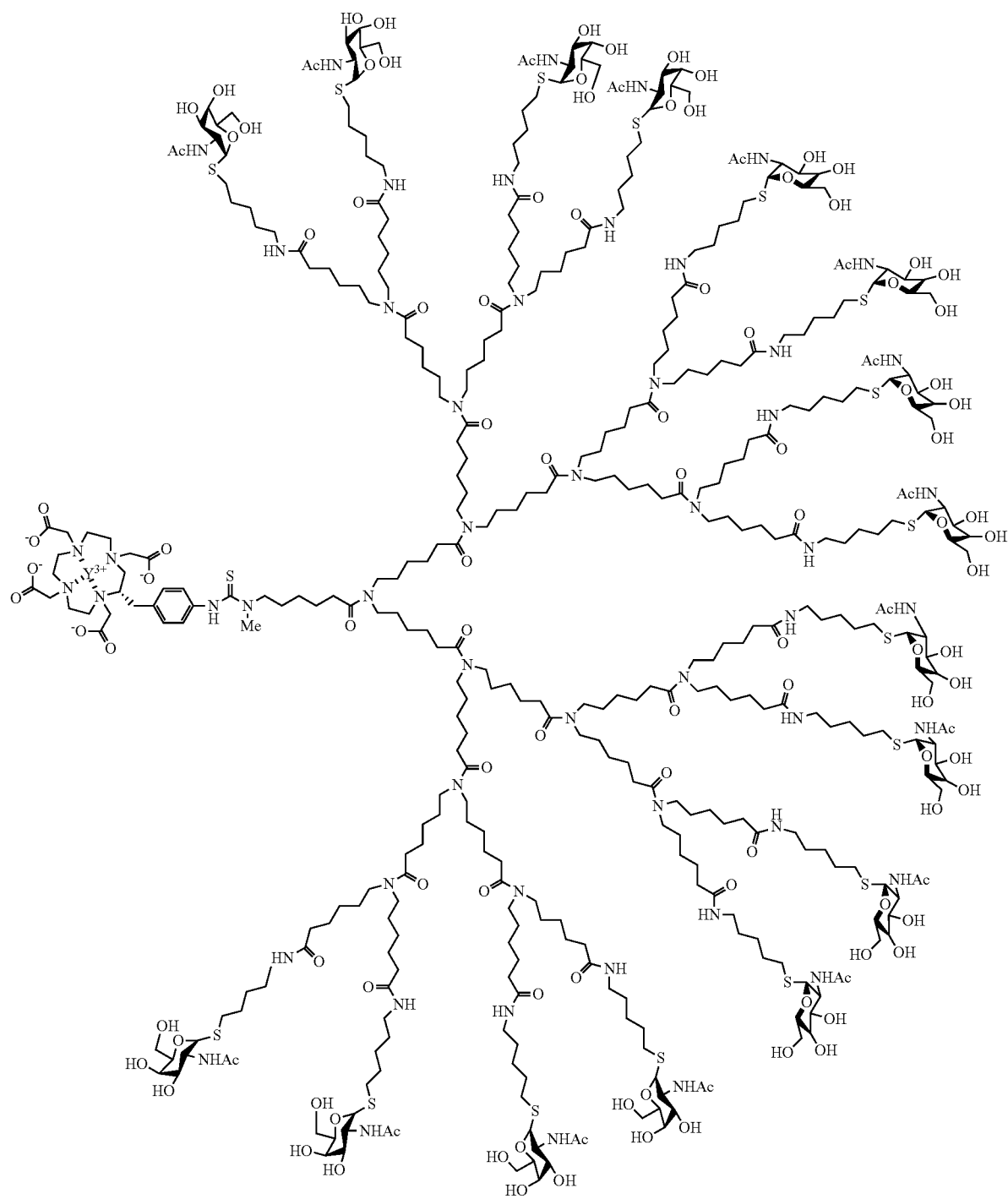

The crude CCA-16-α-thio-peracetyl galactosamine-DOTA-Y$^{3+}$ was dissolved in MeOH (0.5 mL) and a degassed NaOH (0.2 N, 400 μL) was added to the solution. After 30 min, the reaction mixture was evaporated to dryness and taken up in minimum water and loaded onto HPLC (XBridge C18, 20-70% (v/v) gradient of acetonitrile in water (both containing 0.05% TFA), 10 min). The appropriate fractions were pooled together and lyophilized to afford a total of 22 mg of the target compound as a white foam, with an overall yield of 64% starting from CCA-16-methyl ester-NHBoc. $^1$H NMR (600 MHz, D$_2$O) δ: 7.21-7.24 (m, 4H, Ph), 5.43 (d, 16H, J=5.2 Hz, H$_{sugar}$-1), 4.27 (dd, 16H, J=5.2 Hz, J=11.2 Hz, H$_{sugar}$-2), 4.17-4.14 (m, 16H, H$_{sugar}$-5), 3.96 (d, 16H, J=2.7 Hz, H$_{sugar}$-4), 3.75 (dd, 16H, J=2.7 Hz, J=11.2 Hz, H$_{sugar}$-3), 3.68 (d, 32H, J=6.0 Hz, H$_{sugar}$-6), 3.23 (bs, 64H), 3.15-3.08 (m, 36H), 3.00 and 2.85 (2s, 3H, NCH$_3$), 2.58-2.47 (m, 34H), 2.30 (bs, 32H), 2.16-2.13 (m, 34H), 1.96 (s, 48H, NHCOCH3), 1.55-1.30 (m, 198H), 1.23-1.15 (m, 102H). $^{13}$C NMR (125 MHz, D$_2$O) δ: 175.94, 174.24, 163.04, 162.81, 117.31, 115.38, 83.84, 71.62, 68.46, 67.77, 61.07, 50.29, 48.22, 45.86, 39.19, 35.78, 32.74, 30.26, 28.77, 28.24, 27.13, 26.90, 26.22, 25.86, 25.80, 25.51, 25.39, 22.09. ESI-MS (m/z): $[M+5H]^{5+}$ calc. 1,812.2, obs. 1,813.1; $[M+6H]^{6+}$ calc. 1,510.3, obs. 1,511.2.

Example 2: Exemplary Experimental Materials and Methods for Biological Studies

Materials. The anti-GPA33 DOTA-PRIT BsAb (huA33-C825) was prepared as described previously in WO2016/130539. The GPA33(+) human colorectal cancer cell line SW1222 was obtained from the Ludwig Institute for Cancer Immunotherapy (New York, N.Y.) and was maintained in Minimal Essential Medium supplemented with 10% heat-inactivated fetal calf serum, 2.0 mM glutamine, 100 units/mL penicillin, and 100 μg/mL streptomycin.

Radioiodination of BsAb. $^{131}$I was received from Nordion (Ottowa, ON, Canada). Precoated iodogen tubes was obtained from Thermo Fisher Scientific (Waltham, Mass.). Pre-packed Sephadex G-25 columns (PD10 columns) were obtained from GE Healthcare Life Sciences (Pittsburgh, Pa.). Aliquots of the anti-GPA33 BsAb were radioiodinated according to the IODO-GEN method (Salacinski P R et al., Analytical biochemistry 117: 136-46 (1981); Harlow E, Lane D. USING ANTIBODIES: A LABORATORY MANUAL. Cold Spring Harbor, N.Y. (1999)) followed by gel-filtration purification using commercial pre-packed PD10 columns (consisting of Sephadex G-25 resin). The radiochemical purity was determined to be >98% using size-exclusion high pressure liquid chromatography coupled with radiodetection. Briefly, to prepare $^{131}$I-huA33-C825, 100 μg was mixed with 80 μL of 0.2 M sodium phosphate pH 7.4 in a pre-coated iodogen tube. Next, 400 μCi of $^{131}$I was added. After 5 minutes at room temperature, the reaction was transferred to a new tube containing 50 μL of iodogen-stop buffer [10 mg/mL of tyrosine (saturated), 10% glycerol, 0.1% xylene cylanol in PBS] and purified using a PD10 column that was pre-equilibrated and eluted with saline+1% (w/v) BSA added.

Animal models. Female athymic nude mice (6-8 weeks old) were obtained from Harlan (Indianapolis, Ind.) or Envigo (Huntingdon, United Kingdom). Mice were allowed to acclimate for a minimum of 1 week. To determine the effect of dendron-clearing agent CCA-16-DOTA-$Y^{3+}$ on blood clearance of $^{131}$I-BsAb, normal (non-tumored) mice were used. For DOTA-PRIT biodistribution experiments, groups of mice bearing subcutaneous (s.c.) SW1222 human colorectal cancer xenografts were used. To establish SW1222 tumors, mice were inoculated with $5.0\times10^6$ cells in a 200 μL cell suspension of a 1:1 mixture of media with reconstituted basement membrane (BD Matrigel, Collaborative Biomedical Products Inc., Bedford, Mass.) on lower flank via s.c. injection, and established tumors (100-300 mm3) were observed within 7-10 days.

Blood Clearance of $^{131}$I-BsAb. The antibody tracer was prepared for injection by mixing the $^{131}$I-BsAb with additional carrier antibody to achieve 250 μg (1.19 nmol) per dose. All blood sampling and injections were performed via the tail vein. Normal mice (n=15) were intraveneously administered at t=0 with 250 μg (1.19 nmol)$^{131}$I-BsAb and with either: vehicle (saline; n=3) or 25 μg of clearing agent (formulated in 250 μL of saline; n=12) at t=24 h. For vehicle, blood was sampled (30-40 μL; n=3/point) at t=1, 2, 3, 4, 24, 25, 26, 27, and 28 h. For clearing agent, blood was sampled (30-40 μL; n=3/point) at t=1, 2, 3, 4, 24, 24.1 (5 min p.i. CA), 24.3 (15 min p.i. CA), 24.5, 25, 26, 27, and 28 h. Radioactivity concentrations were determined for each sample by counting in a gamma counter (PerkinElmer Life Sciences Wallac Wizard 3). Count rates were background- and decay-corrected, converted to activities using a system calibration factor specific for the isotope, normalized to the administered activity, and expressed as percent injected dose/g (ID/g). Percent changes in blood activity from baseline (i.e., just prior to clearing agent injection; y1) at time intervals post injection of clearing agent (y2) were calculated using the formula ((y2−y1)/y1)*100.

Dendron Clearing Agent CCA-16-DOTA-$Y^{3+}$ Dose Optimization during DOTA-PRIT. Groups of tumor bearing mice (n=4/group) were injected with BsAb (250 μg, 1.19 nmol; t=−28 h) followed by varying amounts of CCA-16-DOTA-$Y^{3+}$ (0-25 μg; 0-2.76 nmol; t=−4 h). An additional group of tumored-animals were given dextran-clearing agent (62.5 μg; 0.125 nmol; 7.625 nmol (Y)DOTA) in place of the dendron-clearing agent CCA-16-DOTA-$Y^{3+}$ for comparison. Four hours after clearing agent administration, the mice were injected with $^{177}$Lu-DOTA-Bn (150-167 μCi; 30-33 pmol). Mice were sacrificed 48 h post-injection of $^{177}$Lu-activity, organs were removed for assay of radioactivity concentrations as described above. These organs included blood, tumor, heart, liver, spleen, stomach, small intestine, large intestine, kidney, muscle, bone, and tail (site of injection). Tumor-to-non-tumor ratios of percent injected dose/g were also calculated.

Figure 8:
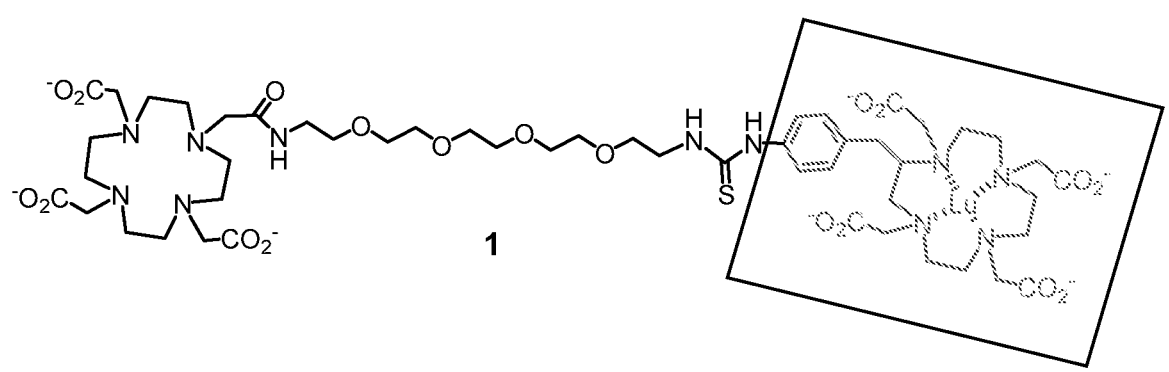
FIG. 8 shows the structure of Proteus-DOTA (chemical formula: $C_{50}H_{80}LuN_{11}O_{19}S^{3-}$; exact mass: 1345.48; molecular weight: 1346.28). The boxed portion of the molecule is a non-radioactive benzyl-DOTA (Lu) hapten that is recognized by the anti-DOTA-hapten antibody single chain variable fragment C825 at a $K_d$=10 pM. The empty three-arm DOTA portion of the molecule can accommodate a variety of radiometals relevant to therapy and/or imaging including $^{225}$Ac, $^{68}$Ga, and $^{64}$Cu.

Preparation of [$^{111}$In]Proteus-DOTA. FIG. 8 shows the structure of Proteus-DOTA (chemical formula: $C_{50}H_{80}LuN_{11}O_{19}S^{3+}$; exact mass: 1345.48; molecular weight: 1346.28). See also Int'l Appl. No. PCT/US18/40911 filed Jul. 5, 2018, incorporated herein by reference. For DOTA-PRIT studies, [$^{111}$In]Proteus-DOTA was prepared from [$^{111}$In]indium chloride (153 MBq [4.14 mCi]) and 1 μL of 10 mg/mL Proteus-DOTA (10 μg; 7.42 nmoles). The [$^{111}$In] Proteus-DOTA yield was 44% and the final Specific Activity (SA) was 7178 GBq/g [194 Ci/g] or 9.67 E6 GBq/mol [2.61 E5 Ci/mol]. Prior to administration into mice, the [$^{111}$In]Proteus-DOTA was purified using a Strata™-X cartridge (33 μm Polymeric Reversed Phase C-18 30 mg/l mL #8B-S100-TAK, Phenomenex© Inc., Torrance, Calif. USA) and the radiochemical purity was verified to be >98% either using an in vitro binding assay with excess BsAb or by analytical reverse-phase HPLC coupled with radiodetection.

Statistical Analysis. Differences between means were determined using the unpaired Student's t-tests.

SPECT/CT imaging. For SPECT/CT imaging and biodistribution studies following in vivo targeting with anti-GPA33-DOTA-PRIT+[$^{111}$In]Proteus-DOTA, SW1222 tumor-bearing mice that had received injections of huA33-C825 BsAb and CCA-16-DOTA-$Y^{3+}$; 25 μg; 2.76 nmol) were injected with 172 pmol/1.67 MBq [45 μCi] of [$^{111}$In]1 (n=4) or 790 pmol/7.66 MBq [207 μCi] of [$^{111}$In]1 (n=1). The following day, the single mouse given the larger administered activity of [$^{111}$In] Proteus-DOTA was imaged by SPECT/CT at 20 h p.i., and all animals were sacrificed at 24 h p.i. for biodistribution.

Example 3: The Clearing Agents of the Present Technology Enhance Blood Clearance of Radiolabeled Bispecific Antibody (BsAb) In Vivo Evaluation of Blood Clearance of $^{131}$I-BsAb ($^{131}$I-huA33-C825). In vivo experiments were conducted using normal (tumor-free) nude mice to evaluate the effect of a single dose of excess dendron-CA of the present technology on blood clearance of $^{131}$I-BsAb.

Initially, groups of animals were injected with 250 μg of $^{131}$I-BsAb, a BsAb dose previously optimized for DOTA-PRIT. Twenty fours hours later, mice were injected with the dendron-CA of the present technology (25 μg, 2.76 nmol) or vehicle control. Serial blood collection was performed at various times up to 4 hours post-injection of CA (or 28 hours post-injection of $^{131}$I-BsAb), and the $^{131}$I-activity concentration was determined in each sample by assay in gamma counter.

As shown in below in FIG. 1, there was initially no significant differences in blood $^{131}$I-activity at baseline (24 h post injection) between the CA and vehicle groups. The CA was effective in decreasing circulating $^{131}$I-BsAb, as the average blood activity concentration significantly dropped by 64% at 5 minutes post injection from 6.7% ID/g to 2.4% ID/g. At 1 hour post injection of CA or vehicle, the average blood activity was 5.8 (−13%) or 1.3% ID/g (−81%), respectively.

These results demonstrate that the clearing agents of the present technology are useful in methods for increasing tumor sensitivity to radiation therapy and/or treating cancer in a subject in need thereof.

Example 4: The Clearing Agents of the Present Technology are Useful for DOTA PRIT Methods The tumor pretargeting results achieved with different doses of CCA-16-DOTA-Y$^{3+}$ are shown in FIG. 2. A 5-25 µg dose of dendron-CA led to average tumor $^{177}$Lu-DOTA-Bn uptakes of 27-41% ID/g at 24 h post-injection $^{177}$Lu-activity, which were comparable to the tumor $^{177}$Lu-DOTA-Bn uptakes observed with the dextran CA and vehicle groups (~35% ID/g). A 25 µg dose of dendron-CA (CCA-16-DOTA-Y$^{3+}$) led to a tumor uptake:blood ratio that was comparable to that observed with a 62.5 µg dose of dextran CA. The effects of the N-acetylgalactosamino dendron-clearing agent CCA-16-DOTA-Y$^{3+}$ on tumor uptake were dose-dependent. See FIG. 3. Moreover, FIG. 4 shows a comparison of the tumor pretargeting results achieved with the clearing agent of the present technology compared with no clearing agent (vehicle) as well as the 500kD dextran-DOTA hapten conjugate clearing agent (i.e., the dextran-CA). The tumor uptake:normal tissue ratios achieved with CCA-16-DOTA-Y$^{3+}$ were comparable to that observed with dextran CA.

In order to demonstrate that [$^{225}$Ac]Proteus-DOTA could be used in combination with DOTA-PRIT for efficient tumor targeting in vivo, a group of nude mice bearing GPA33-expressing SW1222 xenografts was injected i.v. with the BsAb huA33-C825 (250 µg; 1.19 nmol) 28 h prior and i.v. with a clearing agent (62.5 µg; 0.125 nmol dextran; 7.625 nmol (Y)DOTA) 4 h prior to administration of [$^{225}$Ac]Proteus-DOTA (182 pmol, 1.85 kBq [50 nCi]). These mice were sacrificed 24 h p.i. of [$^{225}$Ac]Proteus-DOTA for biodistribution assay. This study was also repeated with [$^{111}$In]Proteus-DOTA (172 pmol/1.67 MBq [45 µCi] of [$^{111}$In]Proteus-DOTA (n=4) or 790 pmol/7.66 MBq [207 µCi] of [$^{111}$In]Proteus-DOTA (n=1) using CCA-16-DOTA-Y$^{3+}$ (25 µg; 2.76 nmol)). The following day, the single mouse given the larger administered activity of [$^{111}$In]Proteus-DOTA was imaged by SPECT/CT at 20 h p.i., and all animals were sacrificed at 24 h p.i. for biodistribution.

Figure 5A:
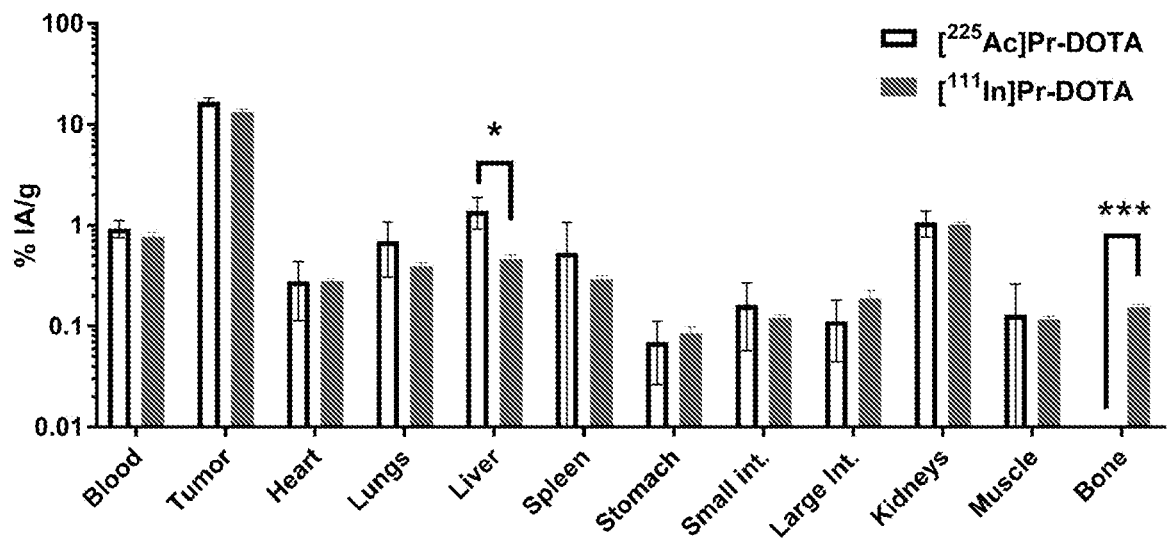
FIG. 5(A) shows a comparison of the biodistribution of tracer pretargeted [$^{225}$Ac]Proteus-DOTA (n=3) or [$^{111}$In] Proteus-DOTA (n=5) in groups of SW1222 tumor-bearing athymic nude mice at 24 h p.i. Following intravenous (via the lateral tail vein) injections of huA33-C825 antibody (0.25 mg, 1.19 nmol), clearing agent, and radiolabeled DOTA-haptens, the animals were euthanized 24 h later for organ collection and assay of radioactivity. *P<0.05, ***P<0.001. Data is presented as mean±SEM.
Figure 5B:
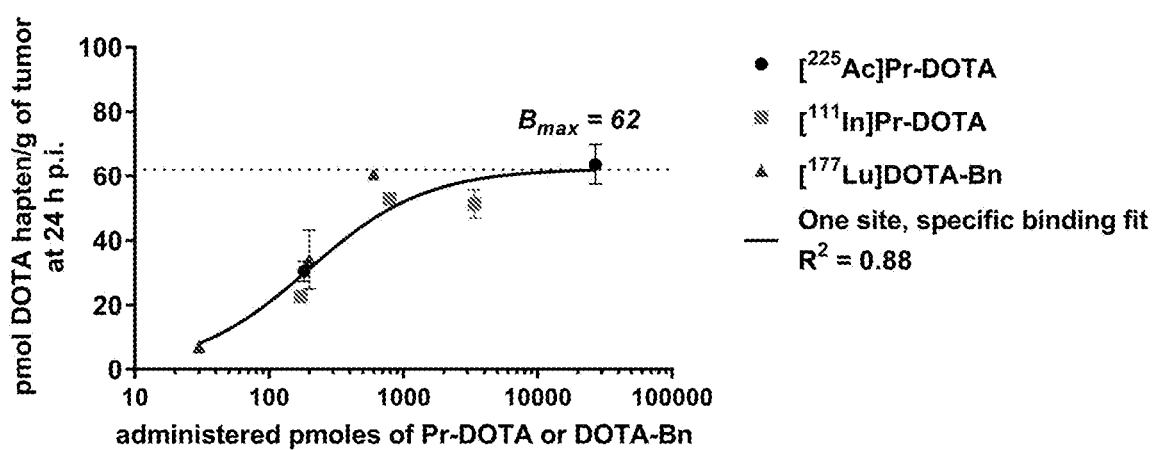
FIG. 5(B) shows the absolute tumor uptake of pretargeted radiolabeled DOTA haptens at 24 h p.i., plotted as a function of administered moles of tracer; n=1-7 for each data point.

As shown in FIG. 5(A), for those animals undergoing pretargeted radioimmunotherapy with [$^{225}$Ac]Proteus-DOTA, the blood, tumor, and kidney uptakes (as percent injected activity per gram of tissue; % IA/g) at 24 h p.i. were 0.94±0.26, 16.71±2.95, and 1.08±0.55, respectively, corresponding to tumor-to-organ activity ratios of about 18:1 and 16:1 for blood and kidney, respectively. For [$^{111}$In]Proteus-DOTA, the blood, tumor, and kidney uptakes at 24 h p.i. were 0.76±0.09, 13.18±0.97, and 1.02±0.06, respectively, corresponding to tumor-to-organ activity ratios of about 17:1 and 13:1 for blood and kidney, respectively. No significant differences were seen between the [$^{225}$Ac]Proteus-DOTA and [$^{111}$In]Proteus-DOTA with the exception of liver which was about 3 times higher for [$^{225}$Ac]Proteus-DOTA (1.40±0.47 versus 0.46±0.05 for [$^{225}$Ac]Proteus-DOTA or [$^{111}$In]Proteus-DOTA, respectively; P<0.05) and for bone, which was higher for [$^{111}$In]Proteus-DOTA (not detectable versus 0.15±0.01 for [$^{225}$Ac]Proteus-DOTA or [$^{111}$In]Proteus-DOTA, respectively; P<0.001). These tumor-to-organ activity ratios are similar to previous biodistribution studies carried out with anti-GPA33-DOTA-PRIT using tracer $^{177}$Lu-DOTA-Bn or $^{86}$Y-DOTA-Bn in the same animal model, where mean tumor uptakes for both DOTA-haptens were ~8% ID/g ((1.85-8.8 MBq; 10-50 pmol for either M-DOTA-Bn haptens) at 24 h p.i. (see Cheal, S. M. et al. Eur J Nucl Med Mol Imaging 43:925-937 (2016)), suggesting that the affinity of C825 for [$^{225}$Ac]Proteus-DOTA was similar. See FIG. 5(B).

Figure 7:
FIG. 7 shows SPECT/CT images approximately 24 h p.i. of pretargeted [$^{111}$In]Proteus-DOTA in a SW1222 human colorectal cancer (CRC) tumor-bearing athymic nude mice. The SW1222-xenograft can be clearly delineated in the flank. Image-based region-of-interest analysis of tumor, kidney (left), heart, and liver revealed activity concentrations (as average±1 SD; percent injected dose per gram) of 6.89±4.68, 0.46±0.47, 0.20±0.24, and 0.22±0.27, respectively.

FIG. 6(A) shows the tumor pretargeting results achieved in animals injected with 172 pmol/1.67 MBq [45 µCi] of [$^{111}$In]Proteus-DOTA (n=4) or 790 pmol/7.66 MBq [207 µCi] of [$^{111}$In]Proteus-DOTA (n=1). The tumor to normal tissue ratios were generally higher in the animal that received the higher dose of [$^{111}$In]Proteus-DOTA. See FIG. 6(A) and FIG. 7.

As shown in FIG. 6(B), the anti-GPA33-DOTA-PRIT results achieved with [$^{225}$Ac]Proteus-DOTA (used in combination with Dextran-CA) and [$^{111}$In]Proteus-DOTA (used in combination with CCA-16-DOTA-Y$^{3+}$) were comparable.

These results demonstrate that the clearing agents of the present technology are useful in methods for increasing tumor sensitivity to radiation therapy and/or treating cancer in a subject in need thereof.

Example 5: Use of N-Acetylgalactosamine Dendron-Clearing Agent for DOTA-Pretargeted Radioimmunotherapy The principal hypothesis that anti-GPA33 PRIT+$^{177}$Lu-aminobenzylDOTA ([$^{177}$Lu]LuDOTA-Bn) including dendron-CA CCA-16-DOTA-Y$^{3+}$ can be used to achieve the high therapeutic indices (TIs) in place of dextran-CA was tested. The therapeutic index is defined herein as estimated tumor/normal tissues absorbed dose ratio.

Absorbed dose estimates for PRIT+[$^{177}$Lu]LuDOTA-Bn including dendron-CA CCA-16-DOTA-Y$^{3+}$: In order to calculate absorbed doses for PRIT+[$^{177}$Lu]LuDOTA-Bn including dendron-CA (the clearing agent of the present technology), groups of nude mice bearing GPA33-expressing SW1222 xenografts (n=5/group) were injected i.v. with the BsAb huA33-C825 (250 µg; 1.19 nmol) 28 h prior and i.v. with dendron-clearing agent CCA-16-DOTA-Y$^{3+}$ (25 µg; 2.76 nmol) 4 h prior to administration of [$^{177}$Lu]LuDOTA-Bn (20 pmol, 3.7 MBq [100 µCi]). These mice were sacrificed at 1, 4, 24, or 48 h p.i. of [$^{177}$Lu]LuDOTA-Bn for biodistribution assay. For each tissue, the non-decay-corrected time-activity concentration data were fitted using Excel to a 1-component, 2-component, or more complex exponential function as appropriate, and analytically integrated to yield the cumulated activity concentration per unit administered activity (MBq-h/g per MBq). The $^{177}$Lu equilibrium dose constant for non-penetrating radiations (8.49 g-cGy/MBq-h) was used to estimate the tumor-to-tumor and select organ-to-organ self-absorbed doses, assuming complete local absorption of the $^{177}$Lu beta rays only, and ignoring the gamma ray and non-self dose contributions. Results obtained from these studies are shown in FIG. 9.

Figure 10:
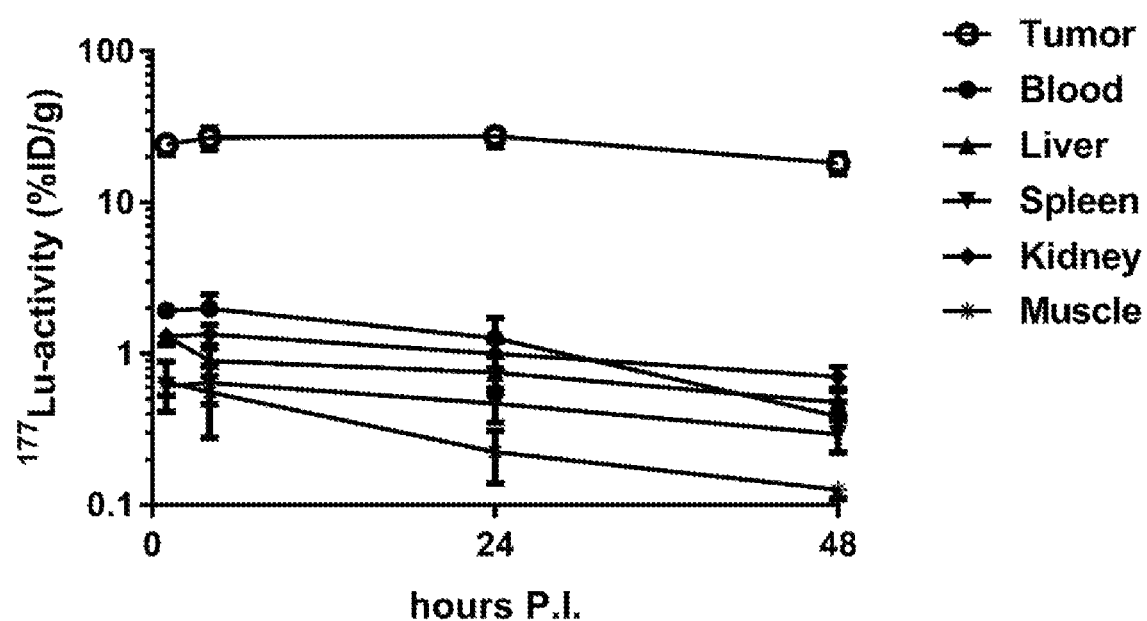
FIG. 10 shows the decay-corrected $^{177}$Lu activity biodistribution curves for SW1222 tumor as well as selected normal tissues from 1 to 48 hours after injection following huA33-C825 PRIT+[$^{177}$Lu]LuDOTA-Bn (3.7 MBq, 20 pmol) with dendron-clearing agent CCA-16-DOTA-Y3+ (25 µg; 2.76 nmol). Data is presented as % ID/g, average±1 SD.

The decay-corrected time-activity curved up to 48 h post injection of [$^{177}$Lu]LuDOTA-Bn for tumor, blood, liver, spleen, kidney, and muscle are shown in FIG. 10. FIG. 11 shows the absorbed doses (cGy/MBq), and therapeutic indices for various tissues. As shown in FIG. 11, the estimated absorbed doses of [$^{177}$Lu]LuDOTA-Bn for blood, tumor, liver, spleen, and kidneys were 11.7, 468.4, 9.97, 5.49, and 13.3 cGy/MBq, respectively. The ratio of absorbed dose estimates for tumor to those for selected normal tissues (i.e., TI) ranged from about 40 (e.g., for blood and kidney) to about 550 for muscle (FIG. 11).

For optimized PRIT+[$^{177}$Lu]LuDOTA-Bn including dextran-CA, estimated absorbed doses (cGy/MBq) to tumor, blood, liver, spleen, and kidney for single-cycle PRIT were 65.8, 0.9 (TI 73), 6.3 (TI 10), 6.6 (TI 10), and 5.3 (TI 12), respectively. See Cheal et al., *Eur J Nucl Med Mol Imaging* 43: 925 (2016). It was demonstrated that effective treatment with no major treatment-related toxicities observed (for e.g., 111.0 MBq delivered in a fractionated dose strategy produce CR with 100% frequency, including survival beyond 140 days in two of nine mice; absorbed doses of 7304, 100, and 588 cGy to tumor, blood, and kidney). Cheal et al., *Eur J Nucl Med Mol Imaging* 43: 925 (2016).

Based on human normal-tissue radiation dose tolerance estimates derived from clinical observations (Marks, et al., *Int J Radiat Oncol Biol Phys.* 76:S10-9 (2010)) the maximum tolerated doses (MTDs) are 250 cGy for bone marrow, 1,500 cGy for lung, 3,000 cGy for liver, and 2,000 cGy for kidney. Therefore, for optimized PRIT+[$^{177}$Lu]LuDOTA-Bn including dextran-CA the maximum tolerated pretargeted [$^{177}$Lu]LuDOTA-Bn activity is 278 MBq, with the bone marrow as the dose-limiting organ. At this activity, the estimated absorbed dose delivered to tumor would be 18,292 cGy (183 Gy), with 250 cGy to blood (marrow) and 1,473 cGy to kidney.

For the above example of PRIT+[$^{117}$Lu]LuDOTA-Bn including dendron-CA CCA-16-DOTA-Y$^{3+}$, the maximum tolerated pretargeted [$^{177}$Lu]LuDOTA-Bn activity was 21 MBq, with the bone marrow as the dose-limiting organ. At this activity, the estimated absorbed dose delivered to tumor would be 9836 cGy (98 Gy), with 246 cGy to blood (marrow) and 280 cGy to kidney. Therefore, effective and safe CRC therapy is predicted in xenografts in mice, on account of the tumor absorbed dose of ~73 Gy, which could be achieved with an administered activity of 15.6 MBq (with 183 cGy to blood (marrow) and 207 cGy to kidney).

Ultimately, these data demonstrate that dendron-CA can be used to achieve cures (for e.g., 70 Gy to tumor) in mouse models of human CRC with less administered $^{177}$Lu-activity compared to the dextran-CA, with differences in dosimetry to critical tissues (e.g., decrease dose to kidney).

These results demonstrate that the clearing agents of the present technology are useful in methods for increasing tumor sensitivity to radiation therapy and/or treating cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A compound that is

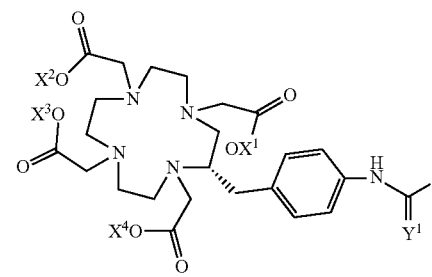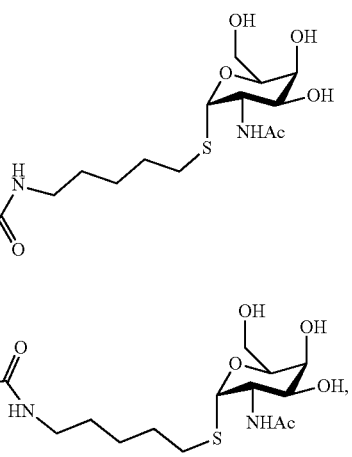

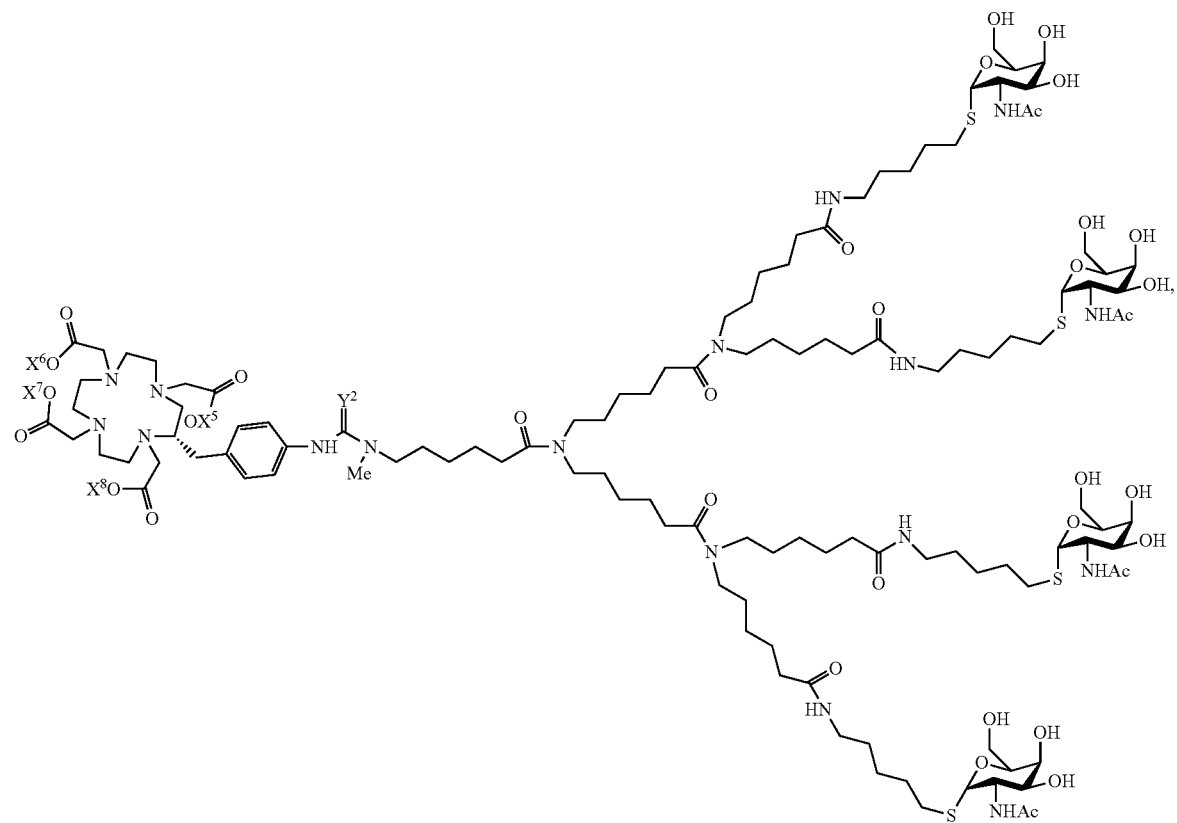

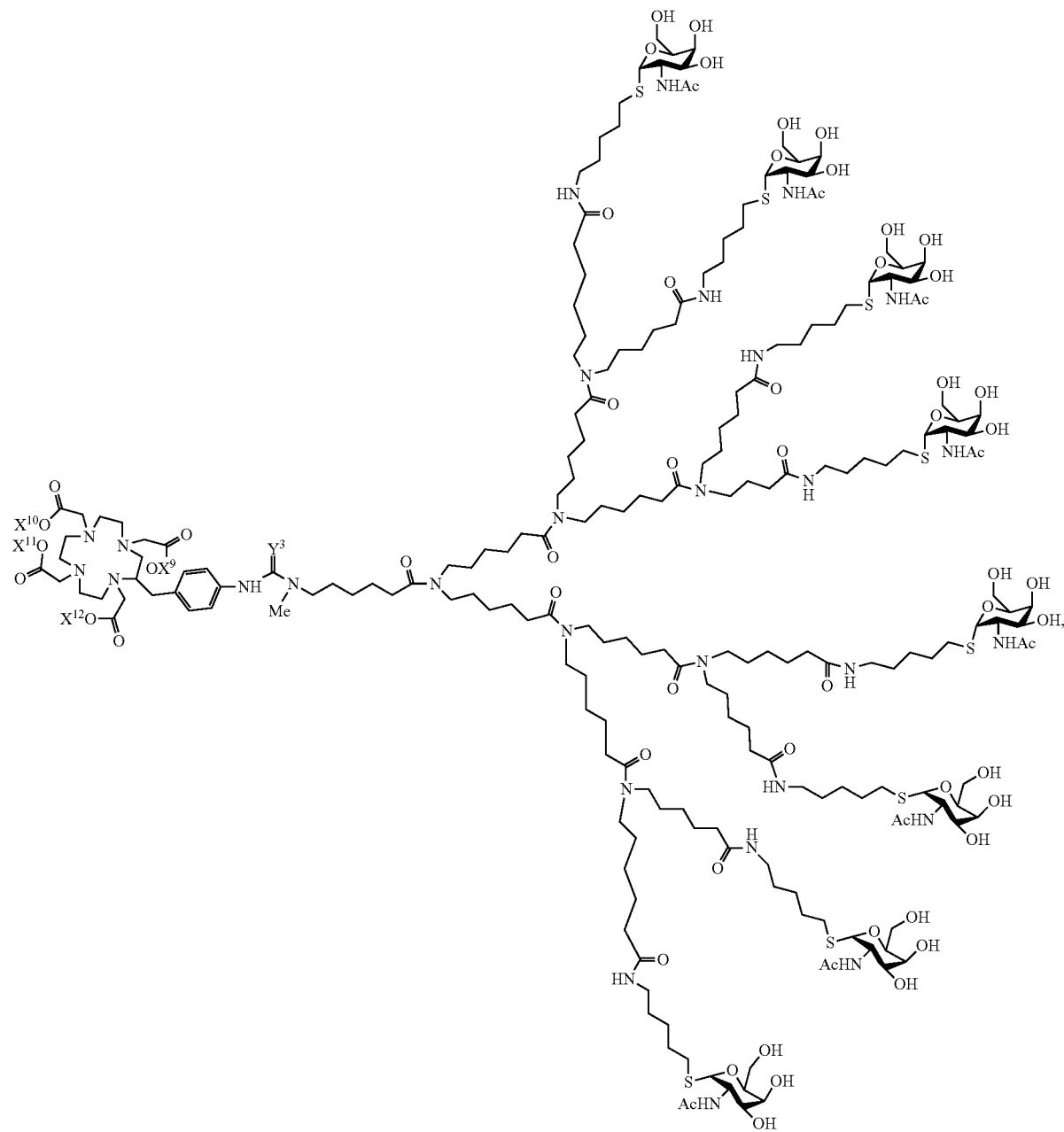

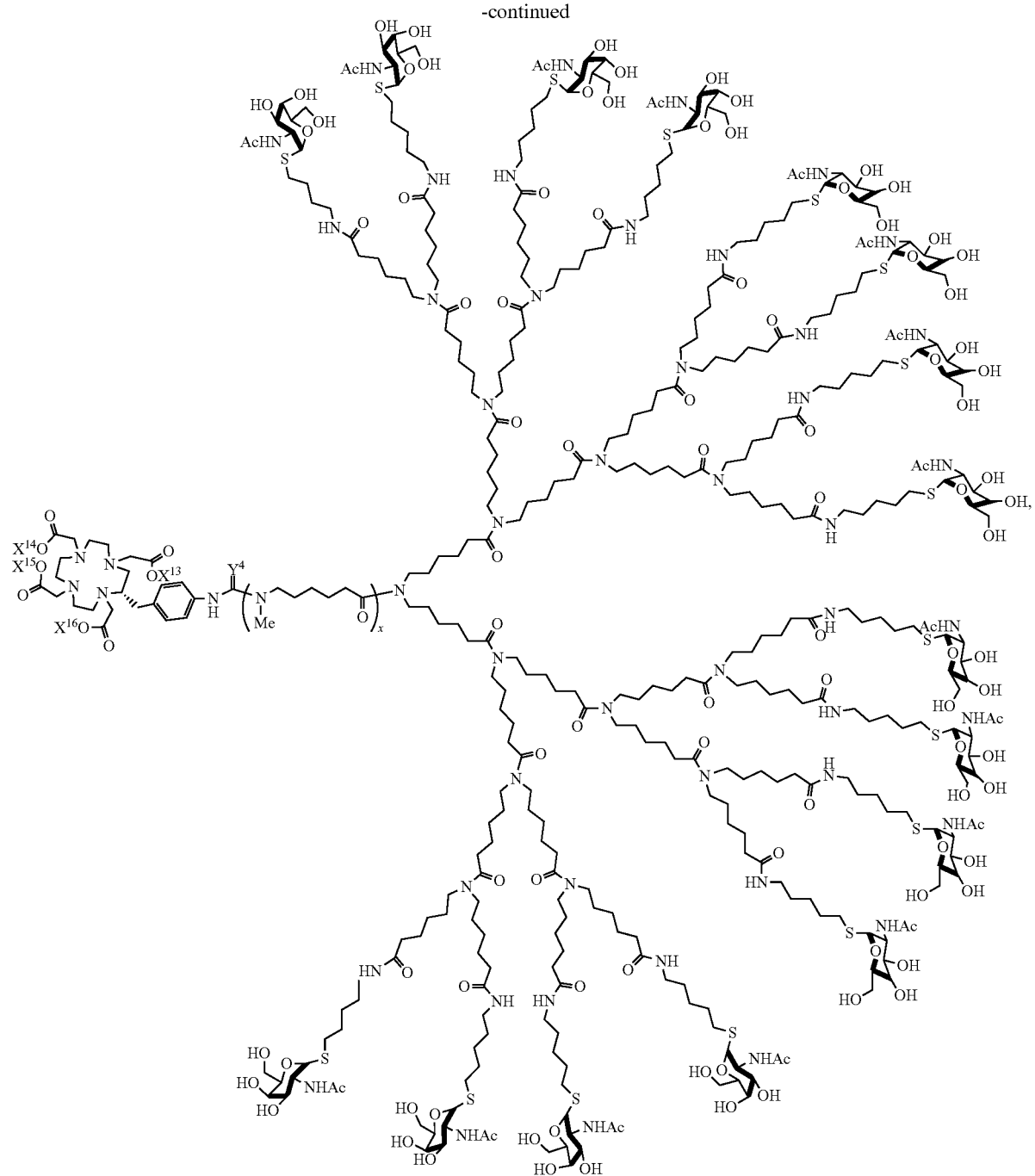

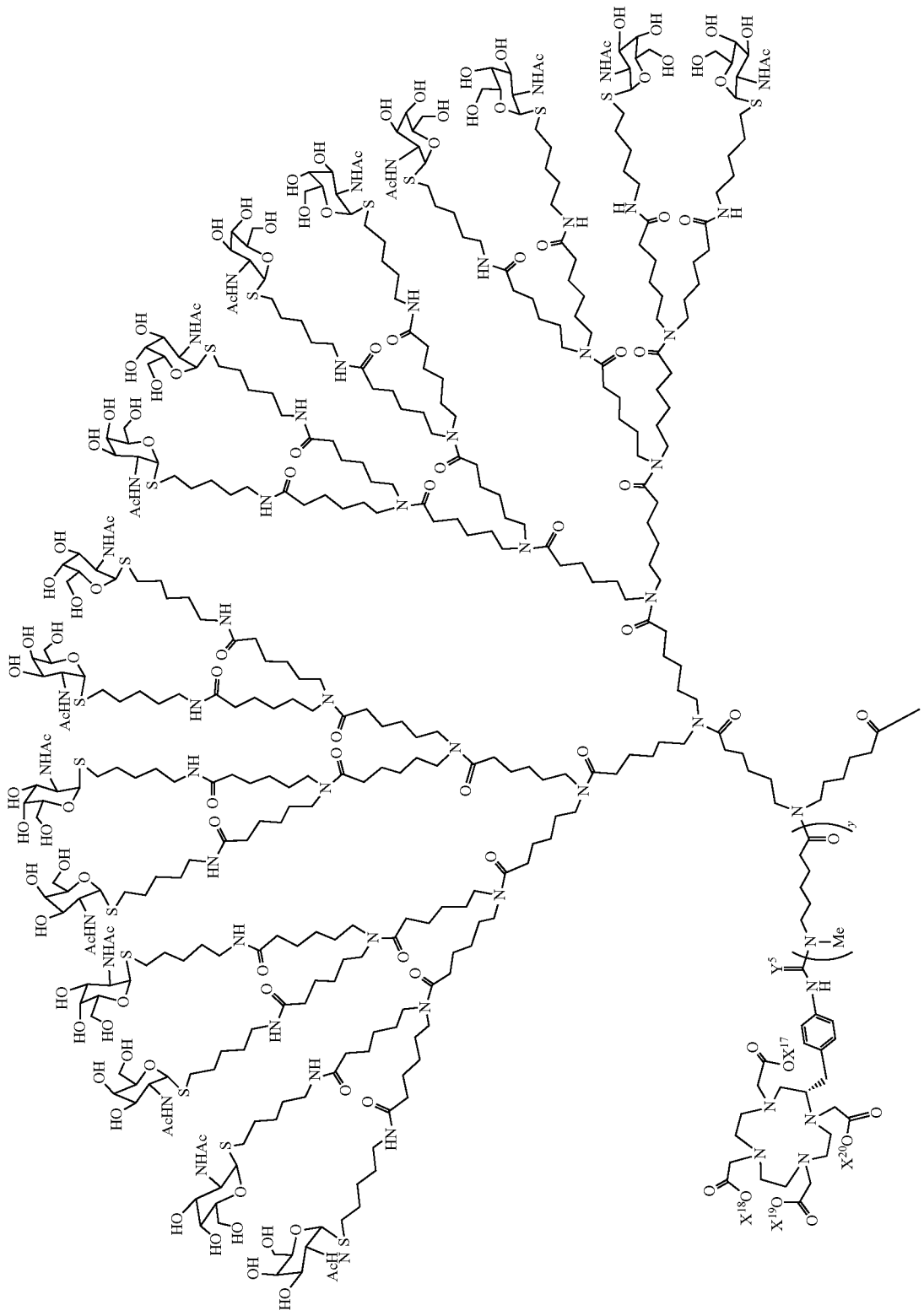

-continued
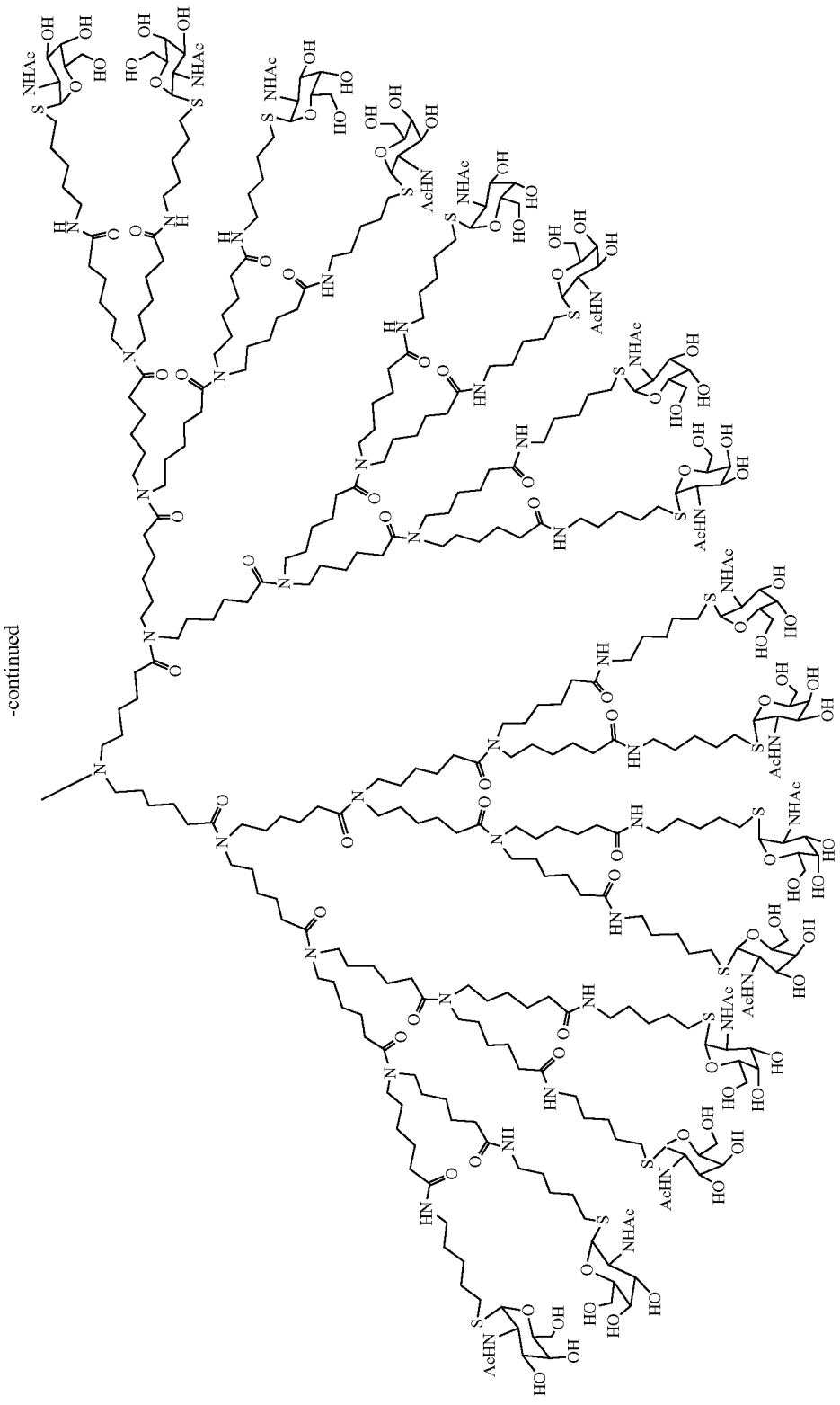

or a pharmaceutically acceptable salt and/or solvate thereof, wherein
$X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}$, and $X^{20}$ are each independently H or a lone pair of electrons providing an oxygen anion;
$Y^1, Y^2, Y^3, Y^4$ and $Y^5$ are each independently O or S;
x is 1, 2, or 3; and
y is 1, 2, 3, or 4.
2. The compound of claim 1, having a formula that is
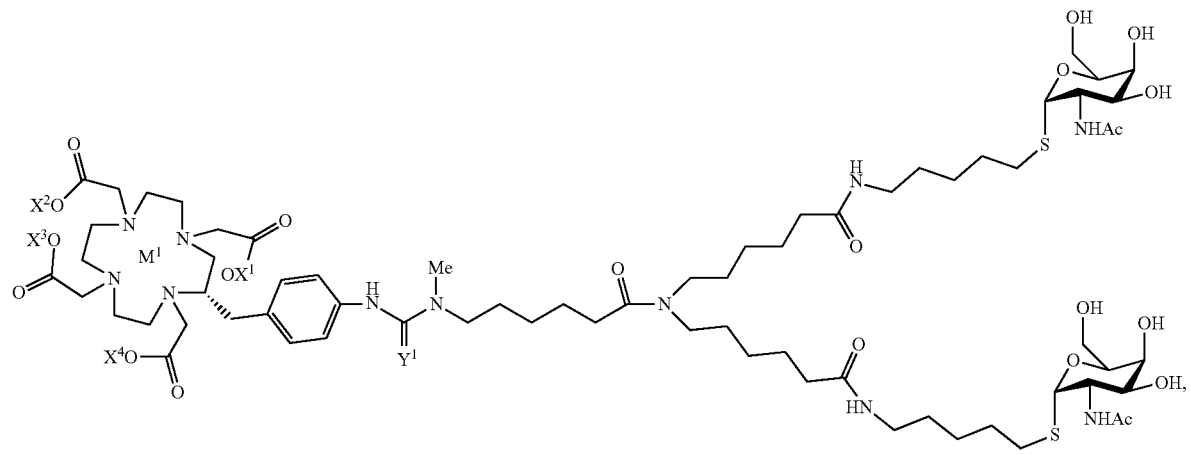
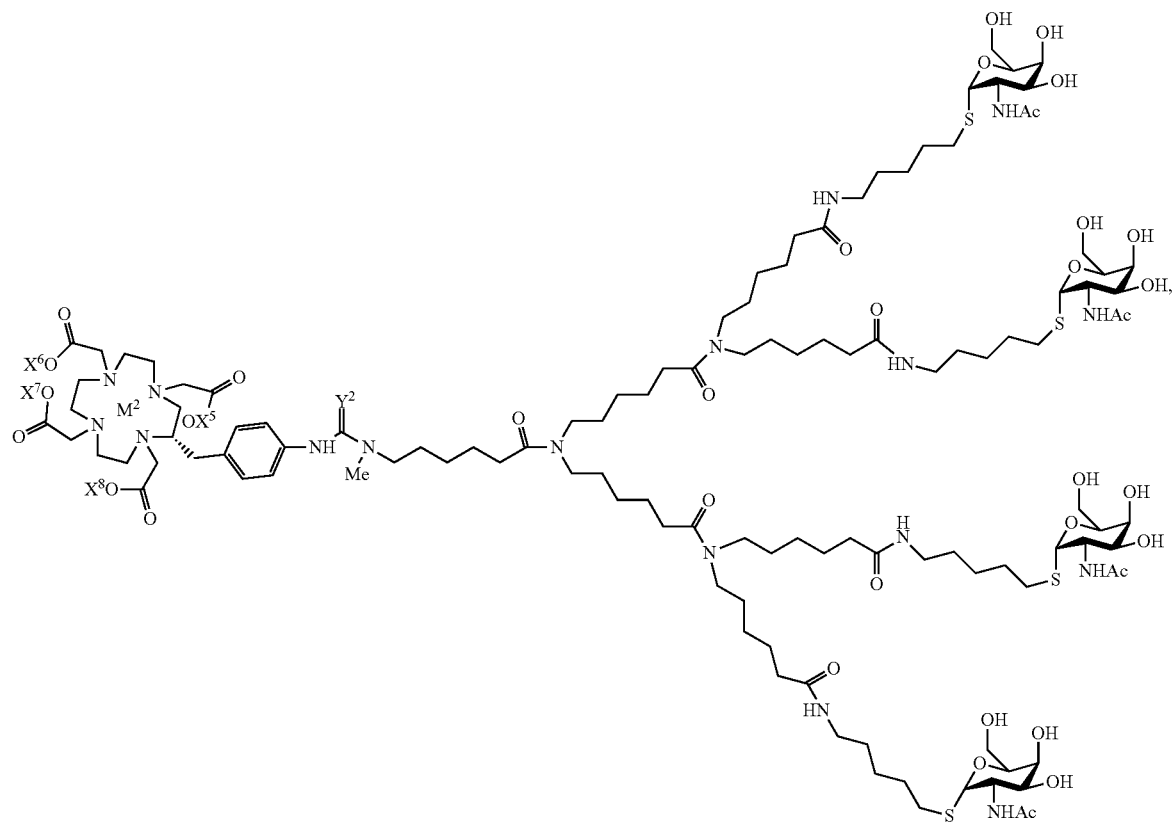

-continued
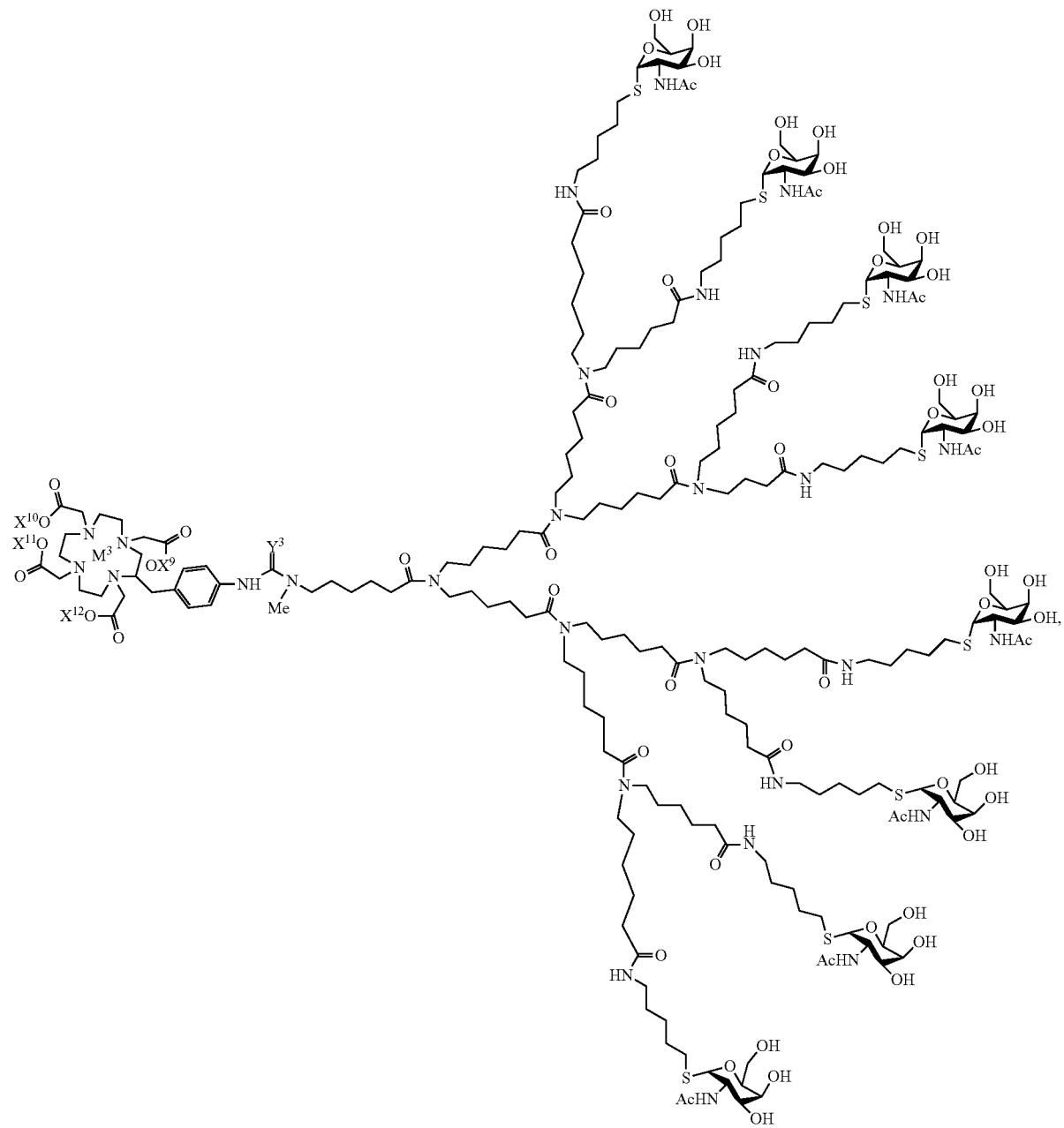

-continued
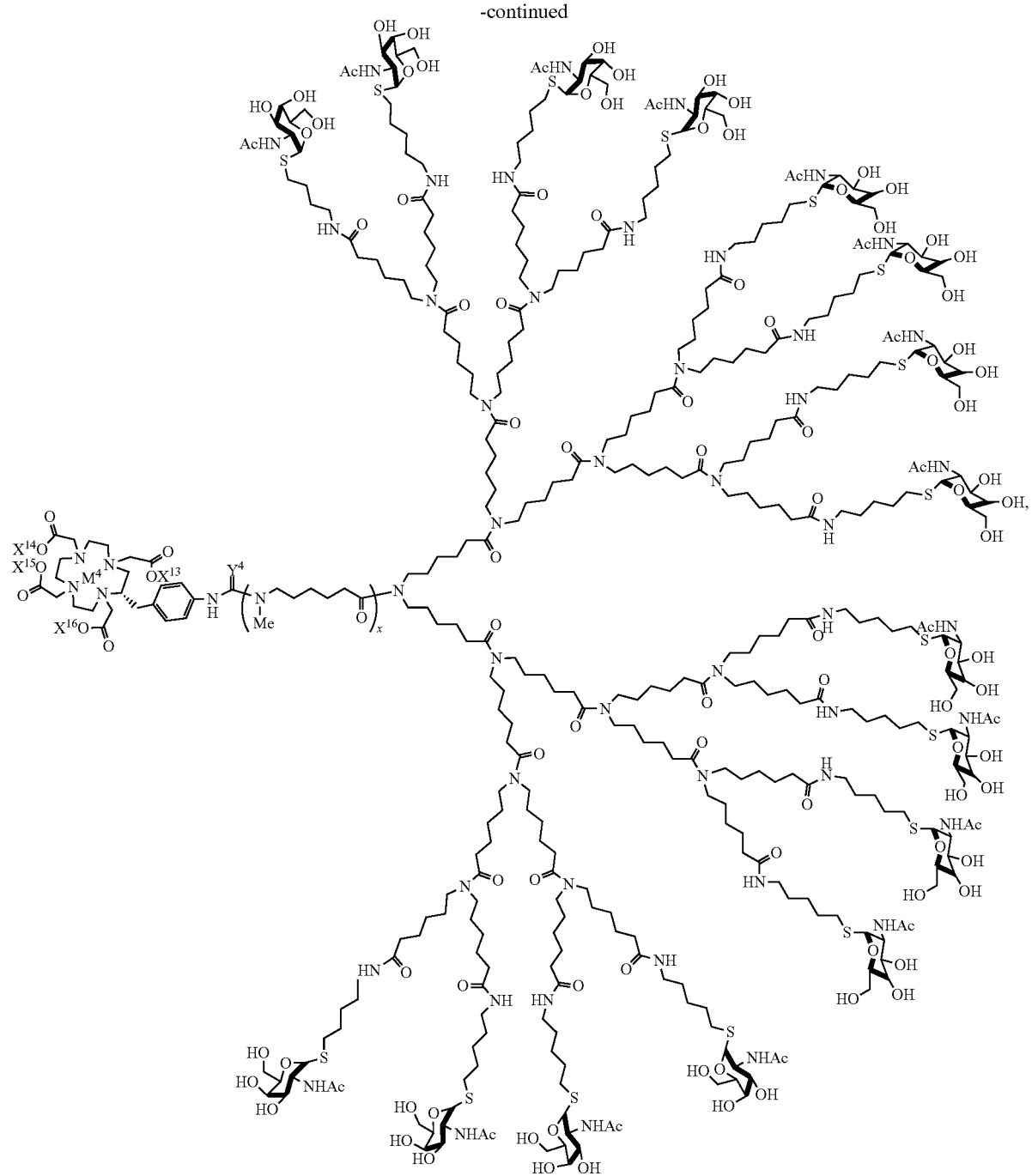

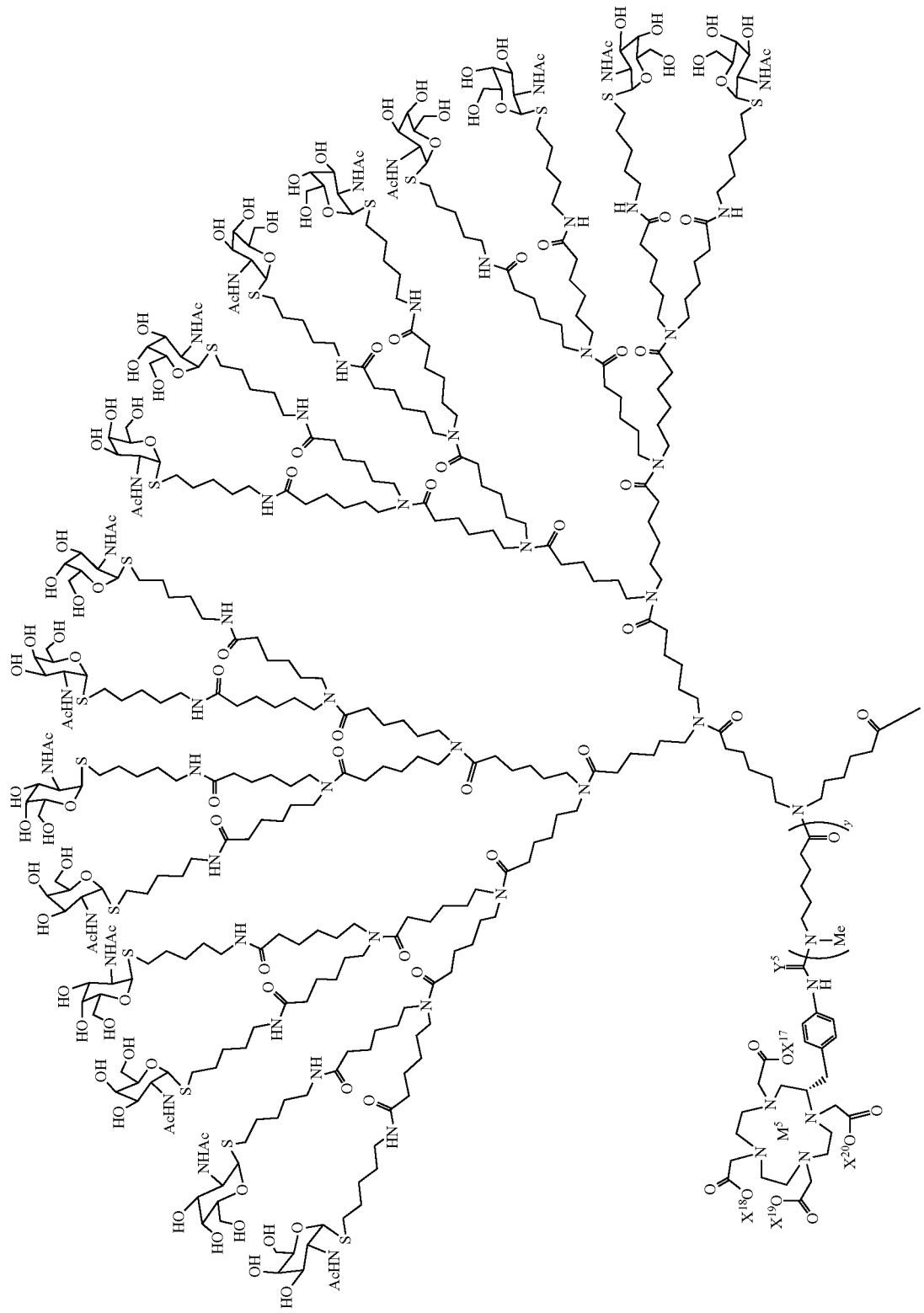

-continued
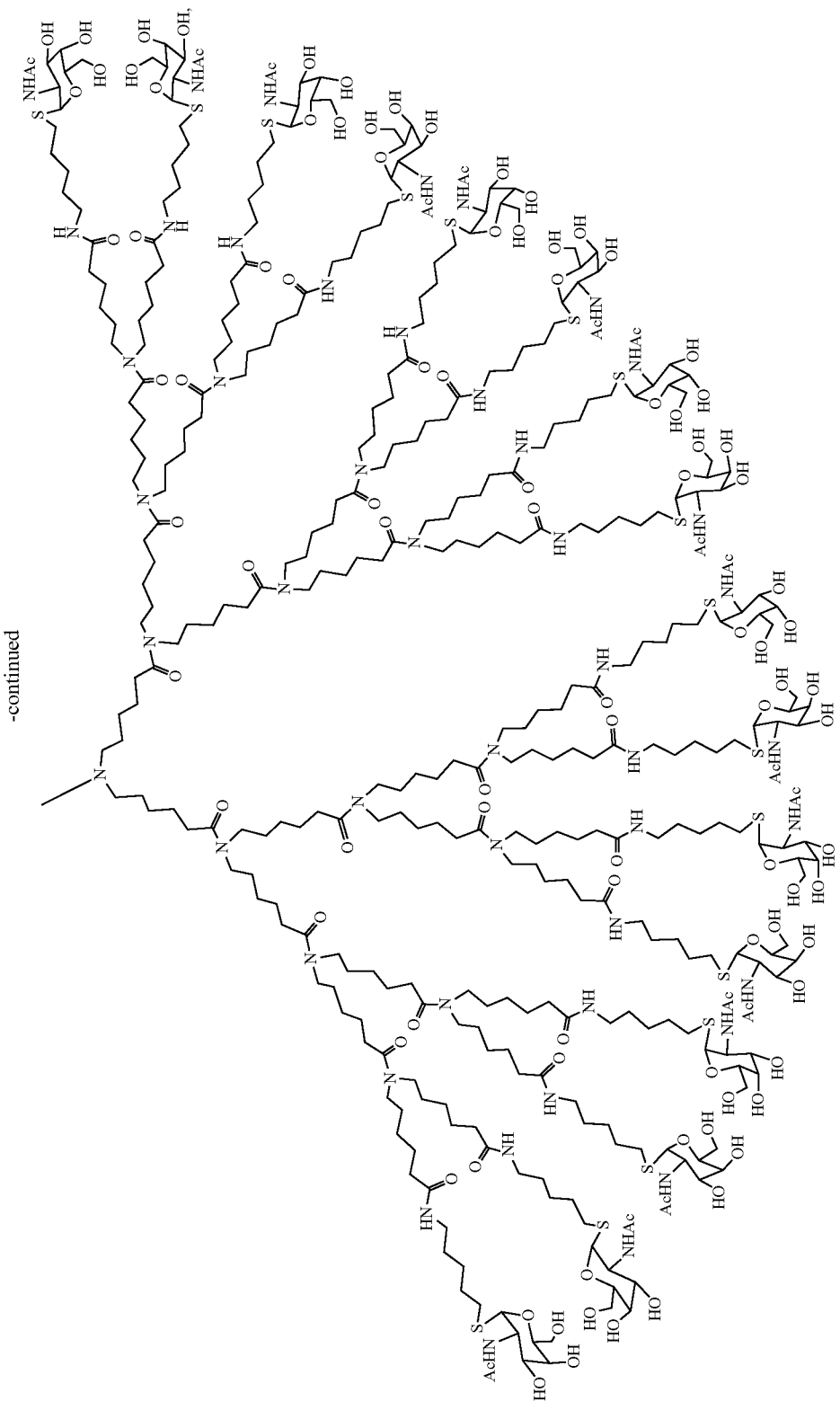

or a pharmaceutically acceptable salt and/or solvate thereof, wherein $M^1M^2$, $M^3$, $M^4$ and $M^5$ are each independently $Lu^{3+}$, $Sc^{3+}$, $Ga^{3+}$, $Y^{3+}$, $In^{3+}$, $La^{3+}$, $Ce^{3+}$, $Eu^{3+}$, $Tb^{3+}$, or $Gd^{3+}$;

$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, and $X^{20}$ are each independently H or a lone pair of electrons providing an oxygen anion;

$Y^1$, $Y^2$, $Y^3$, $Y^4$ and $Y^5$ are each independently O or S;

x is 1, 2, or 3; and y is 1, 2, 3, or 4.

3. The compound of claim 2, wherein $M^1$, $M^2$, $M^3$, $M^4$, and $M^5$ are each independently not a radionuclide, or wherein $Y^1$, $Y^2$, $Y^3$, $Y^4$, and $Y^5$ are each independently S.

4. The compound of claim 1, wherein x is 1 or 2 or wherein y is 2 or 3.

5. A composition comprising the compound of claim 1 and a pharmaceutically acceptable carrier.

6. A method for increasing tumor sensitivity to radiation therapy in a subject diagnosed with cancer, the method comprising
(a) administering an effective amount of an anti-DOTA bispecific antibody to the subject, wherein the anti-DOTA bispecific antibody is configured to localize to a tumor expressing a tumor antigen target;
(b) administering an effective amount of the compound of claim 1 to the subject; and
(c) administering an effective amount of a radiolabeled DOTA hapten to the subject, wherein the DOTA hapten is configured to form a complex with the anti-DOTA bispecific antibody.

7. A method for treating cancer in a subject in need thereof, the method comprising
(a) administering an effective amount of an anti-DOTA bispecific antibody to the subject, wherein the anti-DOTA bispecific antibody is configured to localize to a tumor expressing a tumor antigen target;
(b) administering an effective amount of the compound of claim 1 to the subject; and
(c) administering an effective amount of a radiolabeled DOTA hapten to the subject, wherein the DOTA hapten is configured to form a complex with the anti-DOTA bispecific antibody.

8. The method of claim 7, further comprising sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

9. The method of claim 7, wherein the tumor antigen target is selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, and EpCAM.

10. The method of claim 7, wherein the anti-DOTA bispecific antibody, the radiolabeled DOTA hapten, or the compound is administered intravenously, intramuscularly, intraarterially, intrathecally, intracapsularly, intraorbitally, intradermally, intraperitoneally, transtracheally, subcutaneously, intracerebroventricularly, orally or intranasally.

11. The method of claim 7, wherein the cancer is selected from the group consisting of breast cancer, colorectal cancer, cervical cancer, ovarian cancer, liver cancer, bladder cancer, hepatoma, hepatocellular carcinoma, brain cancer, lung cancer, gastric or stomach cancer, pancreatic cancer, thyroid cancer, kidney or renal cancer, prostate cancer, melanoma, sarcomas, carcinomas, Wilms tumor, endometrial cancer, glioblastoma, squamous cell cancer, astrocytomas, salivary gland carcinoma, vulvar cancer, penile carcinoma, and head-and-neck cancer, optionally wherein the brain cancer is a pituitary adenoma, a meningioma, a neuroblastoma, or a craniopharyngioma.

12. The method of claim 7, wherein the complex emits radioactive levels that are expressed as percentage injected dose per gram tissue (% ID/g).

13. The method of claim 7, wherein the subject exhibits a tumor to normal tissue uptake ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

14. The method of claim 7, wherein the radiolabeled DOTA hapten is labelled with a radionuclide selected from the group consisting of $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr $^{58}$CO, $^{99m}$TC, $^{103m}$Rh, $^{195m}$Pt, $^{119}$Sb, $^{161}$Ho $^{189m}$Os $^{192}$Ir, $^{201}$Tl, $^{203}$Pb, $^{68}$Ga, $^{227}$Th, and $^{64}$Cu.

15. The method of claim 14, wherein the radiolabeled DOTA hapten comprises one or more of Proteus-DOTA, S-2-(R-aminobenzyl)-1,4,7,10-tetraazacyclododecane tetraacetic acid (DOTA-Bn), DOTA-Bn-biotin, BAD (((S)-2-(4-(2-bromo)-acetamido)-benzyl)-DOTA), NBD ((S)-2-(4-nitrobenzyl)-DOTA), DOTA-RGD, DOTA-PEG-E(c (RGDyK))$_2$, DOTA-8-AOC-BBN, p-NO2-Bn-DOTA, DOTA-PESIN, DOTA-biotin-sarcosine (DOTA-biotin), 1,4,7,10-tetraazacyclododecane-1,4,7,10-tetraacetic acid mono (N-hydroxysuccinimide ester) (DOTA-NHS), or DOTATyr-LysDOTA.

16. A kit comprising a compound of claim 1, and instructions for use.

17. The kit of claim 16 further comprising at least one anti-DOTA BsAb.

18. The kit of claim 17, wherein the at least one anti-DOTA BsAb binds to a tumor antigen target selected from the group consisting of GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Leg) antigen, E-cadherin, V-cadherin, and EpCAM.

19. The kit of claim 16 further comprising a DOTA hapten that is optionally labeled with one or more radionuclides.

20. The kit of claim 19, wherein the one or more radionuclides are selected from the group consisting of $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr $^{58}$CO, $^{99m}$TC, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, and $^{64}$Cu.

* * * * *